United States Patent
Jeffers et al.

(10) Patent No.: US 7,056,885 B1
(45) Date of Patent: Jun. 6, 2006

(54) FIBROBLAST GROWTH FACTOR AND NUCLEIC ACIDS ENCODING SAME

(75) Inventors: Michael Jeffers, Branford, CT (US); Richard A. Shimkets, West Haven, CT (US); Sudhirdas K. Prayaga, East Haven, CT (US); Ferenc L. Boldog, North Haven, CT (US); Meijia Yang, East Lyme, CT (US); Catherine Burgess, Wethersfield, CT (US); Elma Fernandes, Branford, CT (US); John L. Herrmann, Gilford, CT (US); William J. LaRochelle, Madison, CT (US); Henri Lichenstein, Madison, CT (US)

(73) Assignee: CuraGen Corporation, Branford, CT (US)

( * ) Notice: Subject to any disclaimer, the term of this patent is extended or adjusted under 35 U.S.C. 154(b) by 910 days.

(21) Appl. No.: 09/609,543

(22) Filed: Jul. 3, 2000

Related U.S. Application Data

(63) Continuation-in-part of application No. 09/494,585, filed on Jan. 31, 2000, now abandoned.

(60) Provisional application No. 60/145,899, filed on Jul. 27, 1999.

(51) Int. Cl.
*A61K 38/18* (2006.01)
*C07K 14/50* (2006.01)

(52) U.S. Cl. .................. 514/12; 530/350; 530/399; 530/402

(58) Field of Classification Search .............. 514/2, 514/12; 530/399, 300, 350
See application file for complete search history.

(56) References Cited

U.S. PATENT DOCUMENTS

| 5,512,460 A | * | 4/1996 | Nauro et al. |
| 2002/0001825 A1 | | 1/2002 | Itoh |

FOREIGN PATENT DOCUMENTS

| WO | WO 00/54813 | 9/2000 |
| WO | WO 01/07595 | 2/2001 |
| WO | WO 01/31008 A2 | 5/2001 |
| WO | WO 01/68854 | 9/2001 |
| WO | WO 01/72957 A2 | 10/2001 |
| WO | WO 01/92522 | 12/2001 |
| WO | WO 02/02625 | 1/2002 |
| WO | WO 02/24234 | 3/2002 |

OTHER PUBLICATIONS

Galzie et al. Biochem. Cell Biol. 75: 669-685, 1997.*
U.S. Appl. No. 60/161,162, filed Oct. 22, 1999, Itoh et al.
U.S. Appl. No. 60/124,460, filed Mar. 15, 1999, Manning et al.
Pickering, et al. (1997). "Fibroblast Growth Factor-2 Potentiates Vascular Smooth Muscle Cell Migration to Platelet-Derived Growth Factor" and "Upregulation of $\alpha_2\beta_1$ Integrin and Disassembly of Actin Filaments" *Cir. Res.* 80:627-637.
Klein, et al. (1995). "Differential Modulation of Cell Phenotype by Different Molecular Weight Forms of Basic Fibroblast Growth Factor: Possible Intracellular Signaling by the High Molecular Weight Forms" *J. Cell Biol.* Apr; 129(1):233-43.
Basilico and Moscatelli (1992). "The FGF Family of Growth Factors and Ocogenes" *Advances in Cancer Research 59*: 115-165.
Kirikoshi, et al. (2000). "Molecular Cloning and Characterization of Human FGF-20 on Chromosome 8p21.3-p22" *Biochem. Biophys. Res. Commun. 274*: 337-343.
Bange et al. (2002). *Cancer Res 62*: 840-847.
Ohmachi et al. (2000). *Biochemical and Biophysical Res Comm 277*: 355-360.
Wong et al. (2001). *Am J of Medical Genetics 102*: 282-285.
International Search Report for PCT/US02/19400, mailed Jun. 4, 2003.
Bikfalvi, et al. (1997). Endocrine Reviews 18: 26-45.
Kirikoshi, et al. (2000). Biochem and Biophys Res Comm 274: 337-343.

* cited by examiner

*Primary Examiner*—Brenda Brumback
(74) *Attorney, Agent, or Firm*—Mintz, Levin, Cohn, Ferris, Glovsky and Popeo, P.C.; Ivor R. Elrifi, Esq.; Naomi S. Biswas, Esq.

(57) ABSTRACT

The present invention provides FGF-CX polypeptides and polynucleotides, and antibodies that immunospecifically bind to FGF-CX or any derivative, variant, mutant, or fragment of the FGF-CX polypeptide, polynucleotide or antibody. The invention additionally provides methods of use for the FGF-CX polypeptide, polynucleotide and antibody.

6 Claims, 22 Drawing Sheets

FIGURE 1

```
  1
    ATGGCTCCCTTAGCCGAAGTCGGGGGCTTTCTGGGCGGCCTGGAG
    MetAlaProLeuAlaGluValGlyGlyPheLeuGlyGlyLeuGlu
 46
    GGCTTGGGCCAGCAGGTGGGTTCGCATTTCCTGTTGCCTCCTGCC
    GlyLeuGlyGlnGlnValGlySerHisPheLeuLeuProProAla
 91
    GGGGAGCGGCCGCCGCTGCTGGGCGAGCGCAGGAGCGCGGCGGAG
    GlyGluArgProProLeuLeuGlyGluArgArgSerAlaAlaGlu
136
    CGGAGCGCGCGCGGCGGGCCGGGGCTGCGCAGCTGGCGCACCTG
    ArgSerAlaArgGlyGlyProGlyAlaAlaGlnLeuAlaHisLeu
181
    CACGGCATCCTGCGCCGCCGGCAGCTCTATTGCCGCACCGGCTTC
    HisGlyIleLeuArgArgArgGlnLeuTyrCysArgThrGlyPhe
226
    CACCTGCAGATCCTGCCCGACGGCAGCGTGCAGGGCACCCGGCAG
    HisLeuGlnIleLeuProAspGlySerValGlnGlyThrArgGln
271
    GACCACAGCCTCTTCGGTATCTTGGAATTCATCAGTGTGGCAGTG
    AspHisSerLeuPheGlyIleLeuGluPheIleSerValAlaVal
316
    GGACTGGTCAGTATTAGAGGTGTGGACAGTGGTCTCTATCTTGGA
    GlyLeuValSerIleArgGlyValAspSerGlyLeuTyrLeuGly
361
    ATGAATGACAAAGGAGAACTCTATGGATCAGAGAAACTTACTTCC
    MetAsnAspLysGlyGluLeuTyrGlySerGluLysLeuThrSer
406
    GAATGCATCTTTAGGGAGCAGTTTGAAGAGAACTGGTATAACACC
    GluCysIlePheArgGluGlnPheGluGluAsnTrpTyrAsnThr
451
    TATTCATCTAACATATATAAACATGGAGACACTGGCCGCAGGTAT
    TyrSerSerAsnIleTyrLysHisGlyAspThrGlyArgArgTyr
496
    TTTGTGGCACTTAACAAAGACGGAACTCCAAGAGATGGCGCCAGG
    PheValAlaLeuAsnLysAspGlyThrProArgAspGlyAlaArg
541
    TCCAAGAGGCATCAGAAATTTACACATTTCTTACCTAGACCAGTG
    SerLysArgHisGlnLysPheThrHisPheLeuProArgProVal
586
    GATCCAGAAAGAGTTCCAGAATTGTACAAGGACCTACTGATGTAC
    AspProGluArgValProGluLeuTyrLysAspLeuLeuMetTyr
631
    ACT
    Thr
```

FIGURE 2

```
Query:   170 TGGCGCACCTGCACGGCATCCTGCGCCGCCGGCAGCTCTATTGCCGCACCGGCTTCCACC 229
             ||| ||  | ||  | ||  | ||  | ||  |||||||  ||  ||| | ||  || |||
Sbjct:     2 TGGATCATTTAAAGGGGATTCTCAGGCGGAGGCAGCTATACTGCAGGACTGGATTTCACT  61

Query:   230 TGCAGATCCTGCCCGACGGCAGCGTGCAGGGCACCCGGCAGGACCACAGCCTCTTCGGTA 289
             |  | ||| |  |||  |  | |    | ||||| |||  | ||||||||||||  || |
Sbjct:    62 TAGAAATCTTCCCCAATGGTACTATCCAGGGAACCAGGAAAGACCACAGCCGATTTGGCA 121

Query:   290 TCTTGGAATTCATCAGTGTGGCAGTGGGACTGGTCAGTATTAGAGGTGTGGACAGTGGTC 349
             | ||||||||  |||||| || |||||| ||||||||||  ||  || |||||||||| |
Sbjct:   122 TTCTGGAATTTATCAGTATAGCAGTGGGCCTGGTCAGCATTCGAGGCGTGGACAGTGGAC 181

Query:   350 TCTATCTTGGAATGAATGACAAAGGAGAACTCTATGGATCAGAGAAACTTACTTCCGAAT 409
             |||| || || | |||||||| |||| | |||||||||||||| ||||  ||||  || |
Sbjct:   182 TCTACCTCGGGATGAATGAGAAGGGGGAGCTGTATGGATCAGAAAAACTAACCCAAGAGT 241

Query:   410 GCATCTTTAGGGAGCAGTTTGAAGAGAACTGGTATAACACCTATTCATCTAACATATATA 469
             |  | || || | ||||| |||| ||| |||||||||||| || |  | |  || |||||
Sbjct:   242 GTGTATTCAGAGAACAGTTCGAAGAAAACTGGTATAATACGTACTCGTCAAACCTATATA 301

Query:   470 AACATGGAGACACTGGCCGCAGGTATTTTGTGGCACTTAACAAAGACGGAACTCCAAGAG 529
             |  | |  |||| ||  |  | | || ||| || || || |  | || ||||| |||||
Sbjct:   302 AGCACGTGGACACTGGAAGGCGATACTATGTTGCATTAAATAAAGATGGGACCCCGAGAG 361

Query:   530 ATGGCGCCAGGTCCAAGAGGCATCAGAAATTTACACATTTCTTACCTAGACCAGTGGATC 589
             | || | |||| || |||| ||||||||||| ||||||||   ||||||||||||||| |
Sbjct:   362 AAGGGACTAGGACTAAACGGCACCAGAAATTCACACATTTTTTACCTAGACCAGTGGACC 421

Query:   590 CAGA 593
             | ||
Sbjct:   422 CCGA 425
```

FIGURE 3

>gb:GenBank accession number -ID:AB020858|acc:AB020858 Homo sapiens genomic DNA of p21.3-p22 anti-oncogene of hepatocellular colorectal and non-small cell lung cancer , segment 1/11 - Homo sapiens, 100000 bp.

Minus Strand HSPs:

A.
 Score = 1430 (214.6 bits), Expect = 1.6e-126, Sum P(3) = 1.6e-126
 Identities = 288/289 (99%), Positives = 288/289 (99%),
 Strand = Minus / Plus

```
Query:    289 TACCGAAGAGGCTGTGGTCCTGCCGGGTGCCCTGCACGCTGCCGTCGGGCAGGATCTGCA 230
              |||||||||| ||||||||||| |||||||||||| ||||||| ||||||||||||||||
Sbjct:  15927 TACCGAAGAGGCTGTGGTCCTGCCGGGTGCCCTGCACGCTGCCGTCGGGCAGGATCTGCA 15986

Query:    229 GGTGGAAGCCGGTGCGGCAATAGAGCTGCCGGCGGCGCAGGATGCCGTGCAGGTGCGCCA 170
              ||||||| |||||||||||||||||||||||||| | |||||||||||||||||| |||
Sbjct:  15987 GGTGGAAGCCGGTGCGGCAATAGAGCTGCCGGCG-CGCAGGATGCCGTGCAGGTGCGCCA 16045

Query:    169 GCTGCGCAGCCCCCGGCCCGCCGCGCGCGCTCCGCTCCGCCGCGCTCCTGCGCTCGCCCA 110
              .||||||| ||||||||||||||||||||| |||||||||||||| ||||||||||||||
Sbjct:  16046 GCTGCGCAGCCCCCGGCCCGCCGCGCGCGCGTCCGCTCCGCCGCGCTCCTGCGCTCGCCCA 16105

Query:    109 GCAGCGGCGGCCGCTCCCCGGCAGGAGGCAACAGGAAATGCGAACCCACCTGCTGGCCCA 50
              ||||   |||||||||||||||||||||||||||||||||||| |||||||||||||||
Sbjct:  16106 GCAGCGGCGGCCGCTCCCCGGCAGGAGGCAACAGGAAATGCGAACCCACCTGCTGGCCCA 16165

Query:     49 AGCCCTCCAGGCCGCCCAGAAAGCCCCCGACTTCGGCTAAGGGAGCCAT 1
              ||||  ||||||||||||||||||  |||  |||||||||||||||||
Sbjct:  16166 AGCCCTCCAGGCCGCCCAGAAAGCCCCCGACTTCGGCTAAGGGAGCCAT 16214
```

B.
 Score = 1224 (183.6 bits), Expect = 1.6e-126, Sum P(3) = 1.6e-126
 Identities = 250/255 (98%), Positives = 250/255 (98%),
 Strand = Minus / Plus

```
Query:    633 AGTGTACATCAGTAGGTCCTTGTACAATTCTGGAACTCTTTCTGGATCCACTGGTCTAGG 574
              ||||| |||||||||||||||||||||||| |||||||||||||||||||||||||||||
Sbjct:   7257 AGTGTACATCAGTAGGTCCTTGTACAATTCTGGAACTCTTTCTGGATCCACTGGTCTAGG 7316

Query:    573 TAAGAAATGTGTAAATTTCTGATGCCTCTTGGACCTGGCGCCATCTCTTGGAGTTCCGTC 514
              ||||||| ||||||||||||||||||| |||||||||||||||||||||||||||||||
Sbjct:   7317 TAAGAAATGTGTAAATTTCTGATGCCTCTTGGACCTGGCGCCATCTCTTGGAGTTCCGTC 7376

Query:    513 TTTGTTAAGTGCCACAAAATACCTGCGGCCAGTGTCTCCATGTTTATATATGTTAGATGA 454
              ||||||||||||||||||||||||||||| |||||||||||||||||||||||||||||
Sbjct:   7377 TTTGTTAAGTGCCACAAAATACCTGCGGCCAGTGTCTCCATGTTTATATATGTTAGATGA 7436

Query:    453 ATAGGTGTTATACCAGTTCTCTTCAAACTGCTCCCTAAAGATGCATTCGGAAGTAAGTTT 394
              |||||||||||||||||||||||||| ||||||||||||||||||||||  |||||||||
Sbjct:   7437 ATAGGTGTTATACCAGTTCTCTTCAAACTGCTCCCTAAAGATGCATTCGGAAGTAAGTTT 7496
```

FIGURE 3 (cont.)

```
Query:    393 CTC-TGATCCATAGA 380
              ||| |||   | |||
Sbjct:   7497 CTCCTGAAAGAGAGA 7511
```

C.

Score = 530 (79.5 bits), Expect = 1.6e-126, Sum P(3) = 1.6e-126
 Identities = 106/106 (100%), Positives = 106/106 (100%),
 Strand = Minus / Plus

```
Query:    391 CTGATCCATAGAGTTCTCCTTTGTCATTCATTCCAAGATAGAGACCACTGTCCACACCTC 332
              || ||||||||||||| ||| |||||||| |||||||||||||||||||||| |||||||
Sbjct:   9837 CTGATCCATAGAGTTCTCCTTTGTCATTCATTCCAAGATAGAGACCACTGTCCACACCTC 9896

Query:    331 TAATACTGACCAGTCCCACTGCCACACTGATGAATTCCAAGATACC 286
              ||| |||||||||||||| ||| |||||||||||||||||||||||
Sbjct:   9897 TAATACTGACCAGTCCCACTGCCACACTGATGAATTCCAAGATACC 9942
```

FIGURE 4

Sequences analyzed:

1. HUMAN FGF-9 (P31371_HUMAN FGF-9) [SEQ ID NO:9]
2. MOUSE FGF-9 (P54130_MOUSE FGF-9) [SEQ ID NO:10]
3. RAT FGF-9 (P36364_FGF9 RAT FGF-9) [SEQ ID NO:11]
4. XENOPUS XFGF-CX (EAA83474Xen; Xenopus laevis XFGF CX) [SEQ ID NO:12]
5. FGF-CX (cgAB020859) [SEQ ID NO:2]

Multiple Alignment:

```
HUMAN FGF-9      MAPLGEVGNYFGVQDAVP--FGNVPVLP--VDSPVLLSDHLGQSEAGGLPRGPAVTDLDH
RAT FGF-9        MAPLGEVGSYFGVQDAVP--FGNVPVLP--VDSPVLLSDHLGQSEAGGLPRGPAVTDLDH
MOUSE FGF-9      MAPLGEVGSYFGVQDAVP--FGNVPVLP--VDSPVLLSDHLGQSEAGGLPRGPAVTDLDH
XENOPUS XFGF-CX  MAPLADVGTFLGGYDALG-QVGSHFLLPPAKDSPLLFNDPLAQSERLSR-SAP--SDLSH
FGF-CX           MAPLAEVGGFLGGLEGLGQQVGSHFLLPPAGERPPLLGERRSAAERSAR-GGPGAAQLAH

HUMAN FGF-9      LKGILRRRQLYCRTGFHLEIFPNGTIQGTRKDHSRFGILEFISIAVGLVSIRGVDSGLYL
RAT FGF-9        LKGILRRRQLYCRTGFHLEIFPNGTIQGTRKDHSRFGILEFISIAVGLVSIRGVDSGLYL
MOUSE FGF-9      LKGILRRRQLYCRTGFHLEIFPNGTIQGTRKDHSRFGILEFISIAVGLVSIRGVDSGLYL
XENOPUS XFGF-CX  LQGILRRRQLYCRTGFHLQILPDGNVQGTRQDHSRFGILEFISVAIGLVSIRGVDTGLYL
FGF-CX           LHGILRRRQLYCRTGFHLQILPDGSVQGTRQDHSLFGILEFISVAVGLVSIRGVDSGLYL

HUMAN FGF-9      GMNEKGELYGSEKLTQECVFREQFEENWYNTYSSNLYKHVDTGRRRYYVALNKDGTPREGT
RAT FGF-9        GMNEKGELYGSEKLTQECVFREQFEENWYNTYSSNLYKHVDTGRRRYYVALNKDGTPREGT
MOUSE FGF-9      GMNEKGELYGSEKLTQECVFREQFEENWYNTYSSNLYKHVDTGRRRYYVALNKDGTPREGT
XENOPUS XFGF-CX  GMNDKGELFGSEKLTSECIFREQFEENWYNTYSSNLYKHGDSGRRYFVALNKDGTPRDGT
FGF-CX           GMNDKGELYGSEKLTSECIFREQFEENWYNTYSSNIYKHGDTGRRYFVALNKDGTPRDGA

HUMAN FGF-9      RTKRHQKFTHFLPRPVDPDKVPELYKDILSQS
RAT FGF-9        RTKRHQKFTHFLPRPVDPDKVPELYKDILSQS
MOUSE FGF-9      RTKRHQKFTHFLPRPVDPDKVPELYKDILSQS
XENOPUS XFGF-CX  RAKRHQKFTHFLPRPVDPEKVPELYKDLMGYS
FGF-CX           RSKRHQKFTHFLPRPVDPERVPELYKDLLMYT
```

FIGURE 5

```
FGF-CX      MAPLAEVGGFLEGLEGLGQQVSHFLLPPAGERPPLLGERRSAAERSAR-GGPGAAQLAH    59
XFGF-20     MAPLADVGTELGGYDALG-QVGSHFLLPPAKDSPLFNDPLAQSERLSR-SAP--SDLSH    56
FGF-9       MAPLGEVGNYFGVQDAVP--FENVPVLP---VDSPVLISDHLGQSEAGGLPRGSPAV-LDLDH    56
FGF-16      MAEVGGVFASLDWDLHGFSSLGNVPLADSPGFLNERLGQIEGKLQRGSP---LDFAH    55

FGF-CX      LHSILRRRQLYCRTGFHLQILPDGSWQGTRQDHSLFGILEFISVAVGLVSIRGVDSGLYL   119
XFGF-20     LQGILRRRQLYCRTGFHLQILPDGNWQGTRQDHSLFGILEFISVAAIGLVSIRGVDIGLYL   116
FGF-9       LKGILRRRQLYCRTGFHLEIFPNGTIQGTRKDHSRFGILEFISIAVGLVSIRGVDSGLYL   116
FGF-16      LKGILRRRQLYCRTGFHLEIFPNGTVHGTRHDHSRFGILEFISLAVGLISIRGVDSGLYL   115

FGF-CX      GMNDKGELYGSEKLTSECIFREQFEENWYNTYSSNIYKHGDTGRRYFVALNKDGTPRDGA   179
XFGF-20     GMNDKGELFGSEKLTSECIFREQFEENWYNTYSSNLYKHGDSGRRYFVALNKDGTPRDGT   176
FGF-9       GMNEKGELYGSEKLTQECVFRECVFREQFEENWYNTYASTLYKHSDSERQYFVALNKDGTPREGT   176
FGF-16      GMNERGELYGSKKLTRECVFREQFEENWYNTYASTLYKHSDSERQYYVALNKDGSPREGY   175

FGF-CX      RSKRHQKFTHFLPRPVDPERWPELYKDLMYT                                211
XFGF-20     RAKRHQKFTHFLPRPVDPEKWPELYKDLMGYS                               208
FGF-9       RTKRHQKFTHFLPRPVDPDKWPELYKDILSQS                               208
FGF-16      RTKRHQKFTHFLPRPVDPSKLPSMSRDLFHYR                               207
```

FIGURE 6 ptnr:SWISSPROT-ACC:P31371 GLIA-ACTIVATING FACTOR PRECURSOR (GAF) (FIBROBLAST GROWTH FACTOR-9)
(FGF-9) (HBGF-9) - HOMO SAPIENS (HUMAN), 208 aa. Identities = 147/208 (70%), Positives = 170/208
(81%)

```
Query:   1 MAPLAEVGGFLGGLEGLGQQVGSHFLLPPAGERPPLLGERRSAAERSARG-GPGAAQLAH  59
           ||| ||  +  + +   |+  +    +| | +||  ||+  +|   +|   | |   ||
Sbjct:   1 MAPLGEVGNYFGVQDAV--PFGNVPVLPV--DSPVLLSDHLGQSEAGGLPRGPAVTDLDH  56

Query:  60 LHGILRPRQLYCRTGFHLQILPDGSVQGTRQDHSLFGILEFISVAVGLVSIRGVDSGLYL 119
           | ||||| |||| ||||| + ||+||| || || |||| |||| ||||||| |||||||
Sbjct:  57 LKGILRRRQLYCRTGFHLEIFPNGTIQGTRKDHSRFGILEFISIAVGLVSIRGVDSGLYL 116

Query: 120 GMNDKGELYGSEKLTSECIFREQFEENWYNTYSSNIYKHGDTGRRYFVALNKDGTPRDGA 179
           |||+|||||||||||| ||||| |||||||||| ||+|||||||| ||||||||||+|
Sbjct: 117 GMNEKGELYGSEKLTQECVFREQFEENWYNTYSSNLYKHVDTGRRYYVALNKDGTPREGT 176

Query: 180 RSKRHQKFTHFLPRPVDPERVPELYKDLL 208
           |+|||||||||||||||| +|||||||+|
Sbjct: 177 RTKRHQKFTHFLPRPVDPDKVPELYKDIL 205
```

FIGURE 7

Length = 208

Plus Strand HSPs:

Score = 775 (272.8 bits), Expect = 3.4e-76, P = 3.4e-76
Identities = 147/208 (70%), Positives = 170/208 (81%), Frame = +1

```
Query:    1 MAPLAEVGGFLGGLEGLGQQVGSHFLLPPAGERPPLLGERRSAAERSARG-GPGAAQLAH  59
            ||||  ||| || |  |  |||| | ||      | ++  |+ ++  +|  ||  || |
Sbjct:    1 MAPLGEVGSYFGVGVQDAV--PFGNVPVLPV--DSPVLLNDHLGQSEAGGLPRGPAVTDLDH  56

Query:   60 LHGILRRRQLYCRTGFHLQILPDGSVQGTRQDHSLFGILEFISVAVGLVSIRGVDSGLYL 119
            | |||||||||||||||| |  ||| ||| |||| |||||| +|||||||||||||||
Sbjct:   57 LKGILRRRQLYCRTGFHLEIFPNGTIQGTRKDHSRFGILEFISIAVGLVSIRGVDSGLYL 116

Query:  120 GMNDKGELYGSEKLTSECIFREQFEENWYNTYSSNIYKHGDTGPRIFVALNKDGTPRDGA 179
            |||+|||||||||||| |+||||||||| ||||| | ||||||| +|||||||||| | 
Sbjct:  117 GMNEKGELYGSEKLTQECVFREQFEENWYNTYSSNLYKHVDTGRRYYVALNKDGTPREGT 176

Query:  180 RSKRHQKFTHFLPRPVDPERVPELYKDLL 208
            |+||||||||||||||||| +|||||| |
Sbjct:  177 RTKRHQKFTHFLPRPVDPDKVPELYKDIL 205
```

FIGURE 8

Length = 208

Plus Strand HSPs:

Score = 775 (272.8 bits), Expect = 3.4e-76, P = 3.4e-76
Identities = 147/208 (70%), Positives = 170/208 (81%), Frame = +1

```
Query:   1 MAPLAEVGGFLGGLEGLGQQVGSHFLLPPAGERPPLLGERRSAAERSARG-GPGAAQLAH  59
           |||| |||| || |  |||| |||| ||| + |+|||  |+     +|+  || |  ||
Sbjct:   1 MAPLGEVGSYFGVQDAV--PFGNVPVLPV--DSPVLLSDHLGQSEAGGLPRGPAVTDLDH  56

Query:  60 LHGILRPPQLYCRTGFHLQILPDGSVQGTRQDHSLFGILEFISVAVGLVSIRGVDSGLYL  119
           | |||||||||||||||| |||||  ||| +|| ||||||||| ||||||||||||||
Sbjct:  57 LKGILRPPQLYCRTGFHLEIFPNGTIQGTRKDHSRFGILEFISIAVGLVSIRGVDSGLYL  116

Query: 120 GMNDKGELYGSEKLTSECIFREQFEENWYNTYSSNIYKHGDTGRRYFVALNKDGTPRDGA  179
           |||+||||||||||| || |||||||||||||||| ||| |||| | | |||||||+| 
Sbjct: 117 GMNEKGELYGSEKLTQECVFREQFEENWYNTYSSNLYKHVDTGRRYYVALNKDGTPREGT  176

Query: 180 RSKPHQKFTHFLPPVDPERVPELYKDLL  208
           |+|||||||||||||||| ||||||+| 
Sbjct: 177 RTKRHQKFTHFLPRPVDPDKVPELYKDIL  205
```

FIGURE 9

FGF-CX Query Length = 211
XFGF-CX Sbjct Length = 208

Plus Strand HSPs:

Score = 906 (318.9 bits), Expect = 4.4e-90, P = 4.4e-90
Identities = 170/211 (80%), Positives = 189/211 (89%), Frame = +1

```
Query:    1 MAPLAEVGGFLGGLEGLGQQVGSHFLLPPAGEPPPLLGERRSAAERSAPGGPGAAQLAHL  60
            |||||+||||||+|||+||| |||||||||  + + +  ||||+   +  +   |+|||
Sbjct:    1 MAPLADVGTFLGGYDALGQ-VGSHFLLPPAKDSPLLFNDPLAQSERLSRSAP--SDLSHL  57

Query:   61 HGILPPRQLYCPTGFHLQILPDGSVQGTPQDHSLFGILEFISVAVGLVSIPGVDSGLYLG 120
            +|||||||||| |||||||||||+|||||||| ||||||||||||| |||||| ||||| 
Sbjct:   58 QGILRRRQLYCRTGFHLQILPDGNVQGTRQDHSRFGILEFISVAIGLVSIRGVDTGLYLG 117

Query:  121 MNDKGELIGSEKLTSECIFREQFEENWYNTYSSNIYKHGDTGRRYFVALNKDGTPRDGAR 180
            |||||||+||||||||||||||||||||||||||+|||||+|||||||||||||||| +
Sbjct:  118 MNDKGELFGSEKLTSECIFREQFEENWYNTYSSNLYKHGDSGRRYFVALNKDGTPRDGTR 177

Query:  181 SKRHQKFTHFLPRPVDPERVPELYKDLLMYT 211
             |||||||||||||||||+||||+||+|+|+
Sbjct:  178 AKRHQKFTHFLPRPVDPEKVPELYKDLMGYS 208
```

FIGURE 11
Panel A
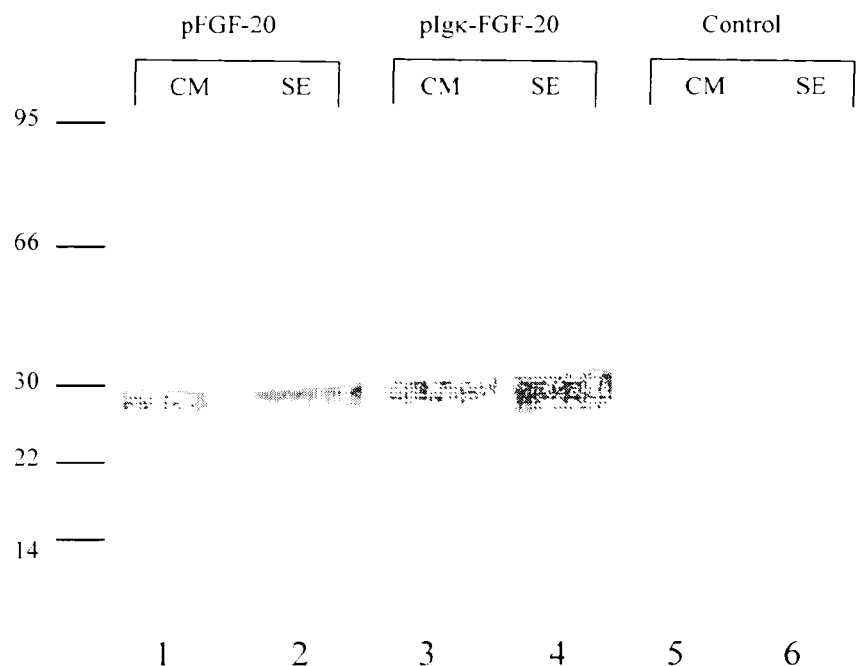
Panel B
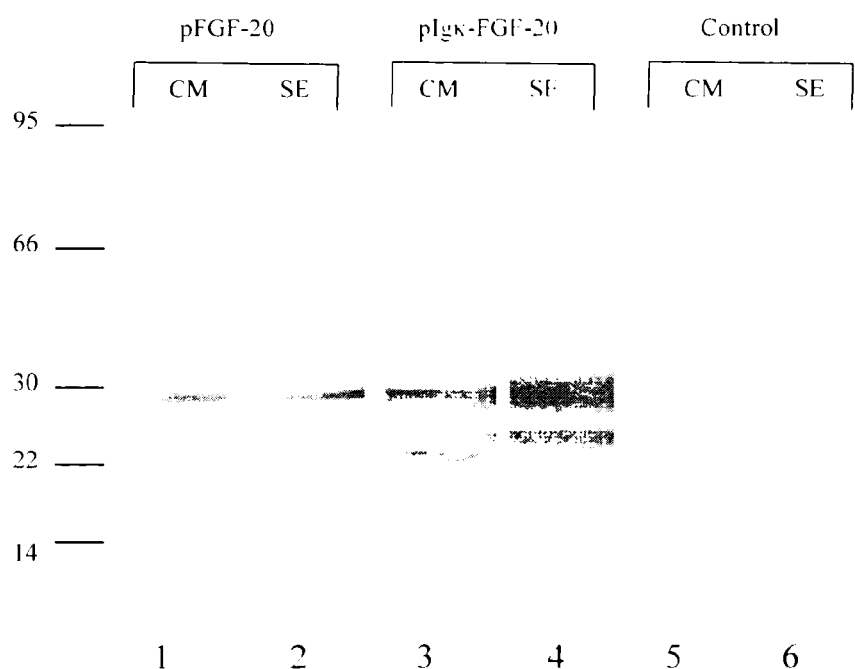

Exon 1

...AGACAGTGAGAGCTTCCCTGCCATTTCAGTGTCAAAGTCCCTCGGAGCGACTCAGAGAGTAACCGGGCCTTAACT
TTTGCGCTCGTTTGCTATAATTTTCTCTATCCACCTCCACCCCCACAACACTCTTTACTGGGGGGTCTTT
GTGTTCCGGATCTCCCCCCTCCATGGCTCCCTTAGCCGAAGTCGGGGGCTTTGTGGGGCGGCCTGGAGGGCTTGGGCCAGCA
                  M   A   P   L   A   E   V   G   G   F   L   G   G   L   E   G   L   G   Q   Q
1

GGTGGGTTCGCATTCCTCTGTGCCTCCTGCCGGGAGCGGCCGCGCCCGCTGGGCGAGCGCGAGCGCAGGAGCGCGGAGCGGA
V   G   S   H   F   L   P   P   A   G   E   R   P   P   L   L   G   E   R   R   S   A   A   E   R   S
21

GCGCGCGGCGGGCGGGGCGGGGGCTGCGCCAGCTGGCGCCACCTGCCACGGCATCCTGCGCCGCCAGCTCTATTGCCGCACC
A   R   G   G   P   G   A   A   Q   L   A   H   L   H   G   I   L   R   R   Q   L   Y   C   R   T
48                                                                          <-|-> Exon 2

GGCTTCCACCTGCAGATCCTGCCAGATGGGAGCGTGCAGGGCACCCGGCAGGACCACAGCCTCTTTGGTATCTTGGAATT
G   F   H   L   Q   I   L   P   D   G   S   V   Q   G   T   R   Q   D   H   S   L   F   G   I   L   E   F
74

CATCAGTGTGGCAGTGGGACTGGTCAGTATTAGAGGTGTGGACAGTGGTCTCTATCTTGGAATGAACAAGGAGAAC
I   S   V   A   V   G   L   V   S   I   R   G   V   D   S   G   L   Y   L   G   M   N   D   K   G   E   L
101                                                             <-|-> Exon 3

TCTATGGATCAGAGAAACTTACTTCCGAATGCATCTTTAGGGAGCAGTTTGAAGAGAACTGGTATAACACCTATTCATCT
Y   G   S   E   K   L   T   S   E   C   I   F   R   E   Q   F   E   E   N   W   Y   N   T   Y   S   S
128

AACATATATAAACATGGAGACACTGGCCGCAGGTATTTTGTGGCACTTAACAAGACGGAACTCCAAGAGATGGCGCCAG
N   I   Y   K   H   G   D   T   G   R   R   Y   F   V   A   L   N   K   D   G   T   P   R   D   G   A   R
154

GTCCAAGAGGCATCAGAAATTTACACATTCTTACCTAGACCAGTGGATCCAGAAAGAGTTCCAGAATTGTACAAGGACC
S   K   R   H   Q   K   F   T   H   F   L   P   R   P   V   D   P   E   R   V   P   E   L   Y   K   D   L
181

TACTGATGTACACTTGA...
L   M   Y   T
208

98—
64—

50—

36—
30—

16—

6 —

Figure 15, Panel A.
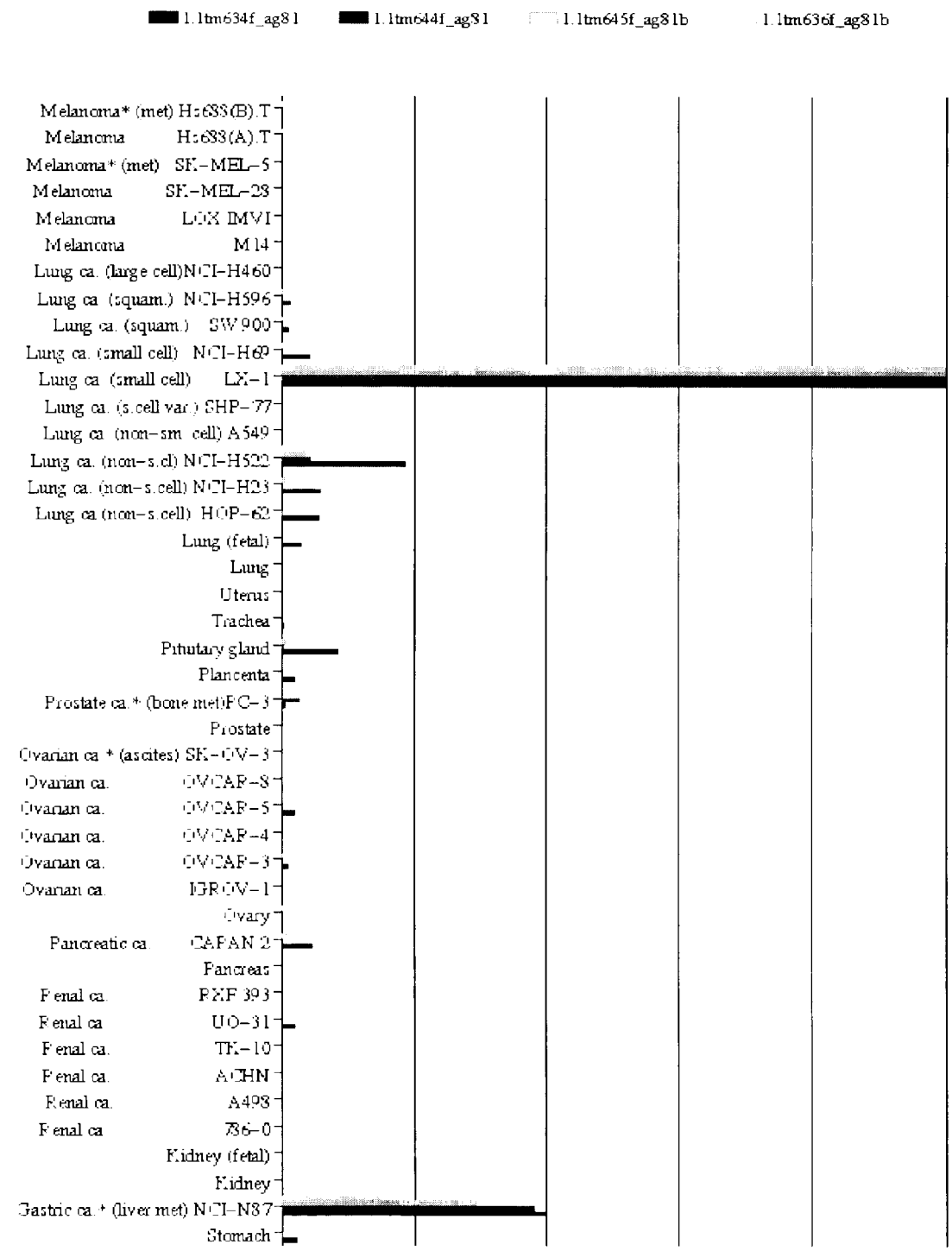

Figure 15, Panel B.
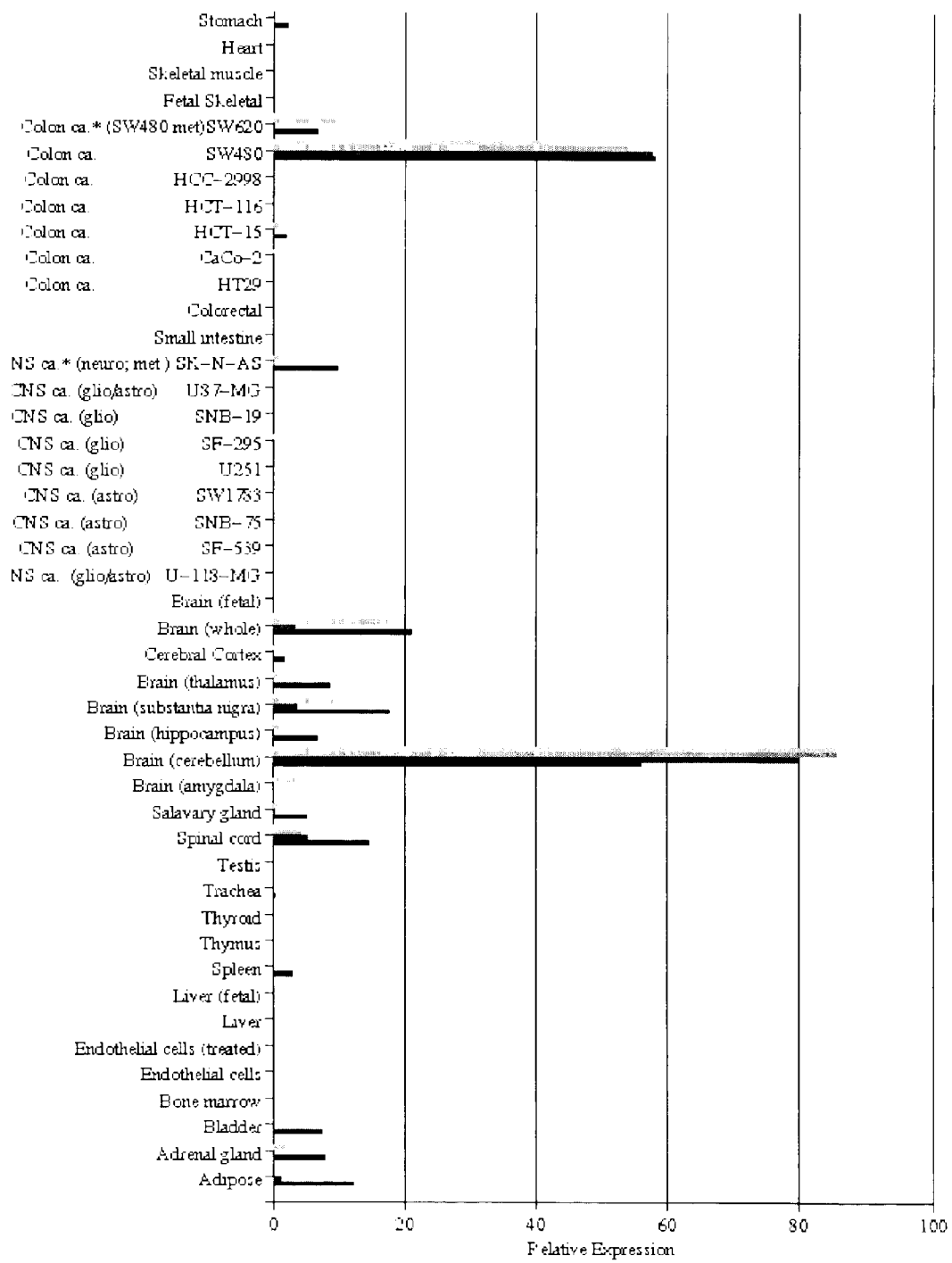

Figure 15, Panel C.

Figure 15, Panel D.
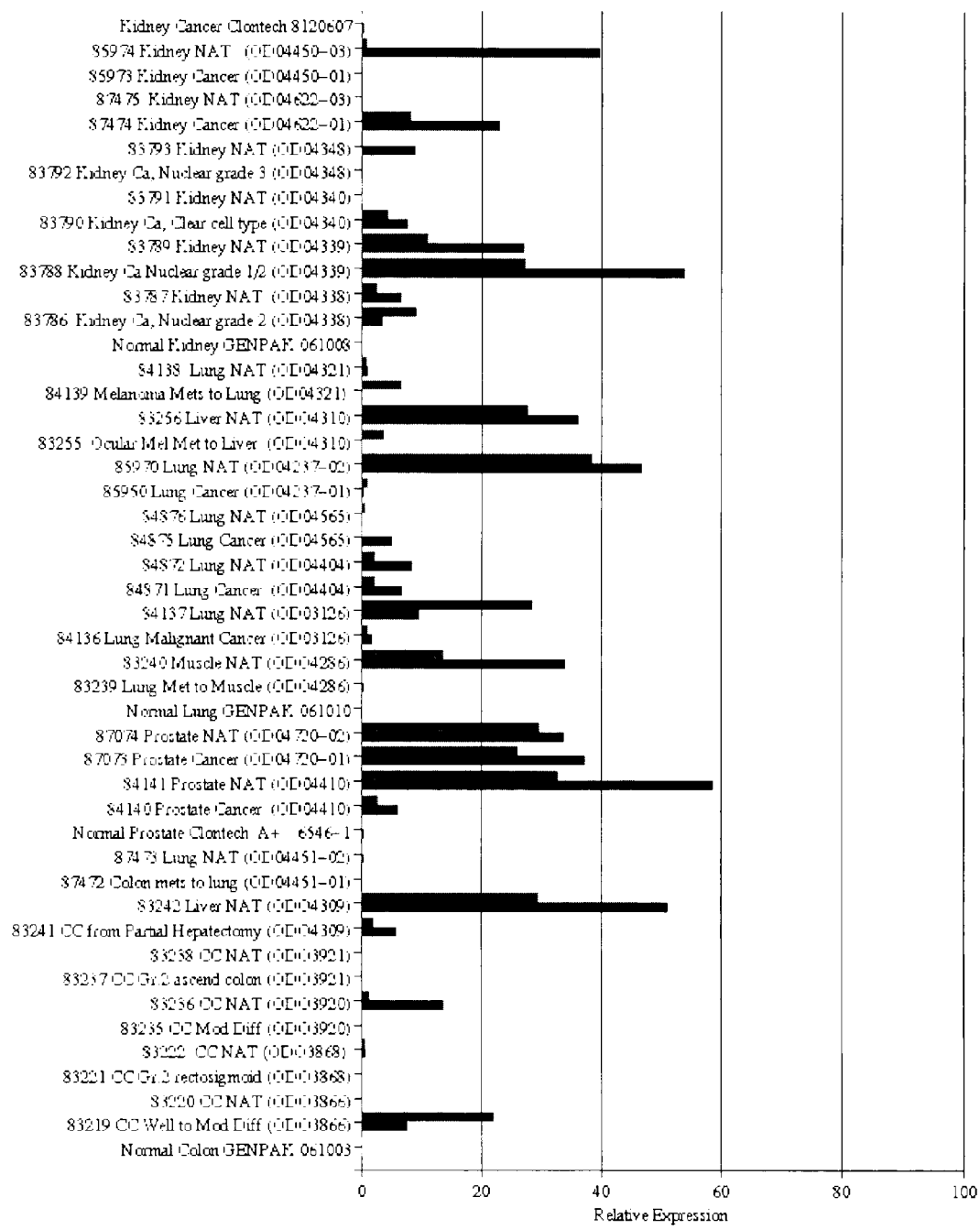

FIGURE 16.
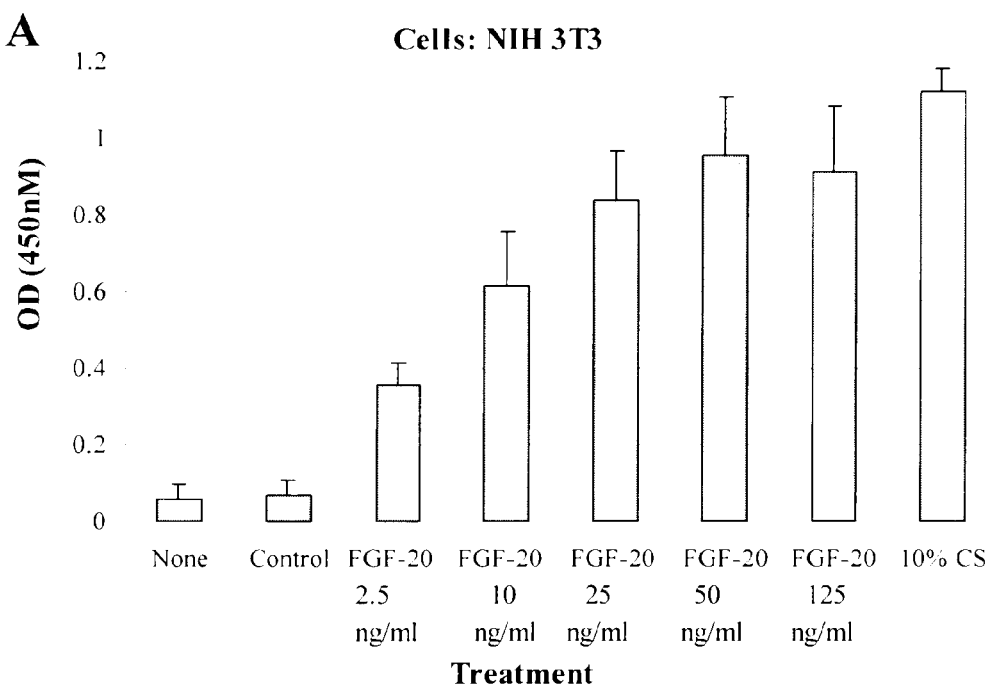
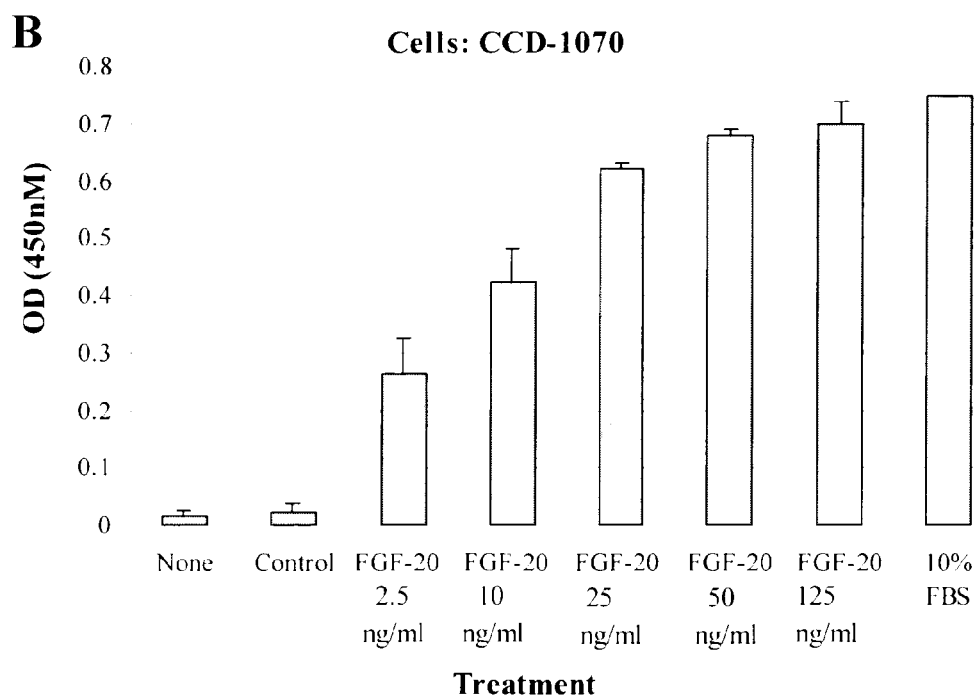

SEQUENCE LISTING

<160> NUMBER OF SEQ ID NOS: 25

<210> SEQ ID NO 1
<211> LENGTH: 633
<212> TYPE: DNA
<213> ORGANISM: Homo sapiens

<400> SEQUENCE: 1

```
atggctccct tagccgaagt cgggggcttt ctgggcggcc tggagggctt gggccagcag      60
gtgggttcgc atttcctgtt gcctcctgcc ggggagcggc cgccgctgct gggcgagcgc     120
aggagcgcgg cggagcggag cgcgcgcggc gggccggggg ctgcgcagct ggcgcacctg     180
cacggcatcc tgcgccgccg gcagctctat tgccgcaccg gcttccacct gcagatcctg     240
cccgacggca gcgtgcaggg cacccggcag gaccacagcc tcttcggtat cttggaattc     300
atcagtgtgg cagtgggact ggtcagtatt agaggtgtgg acagtggtct ctatcttgga     360
atgaatgaca aggagaact ctatggatca gagaaactta cttccgaatg catctttagg     420
gagcagtttg aagagaactg gtataacacc tattcatcta acatatataa acatggagac     480
actggccgca ggtattttgt ggcacttaac aaagacggaa ctccaagaga tggcgccagg     540
tccaagaggc atcagaaatt tacacatttc ttacctagac cagtggatcc agaaagagtt     600
ccagaattgt acaaggacct actgatgtac act                                  633
```

<210> SEQ ID NO 2
<211> LENGTH: 211
<212> TYPE: PRT
<213> ORGANISM: Homo sapiens

<400> SEQUENCE: 2

```
Met Ala Pro Leu Ala Glu Val Gly Gly Phe Leu Gly Gly Leu Glu Gly
  1               5                  10                  15
Leu Gly Gln Gln Val Gly Ser His Phe Leu Leu Pro Pro Ala Gly Glu
                 20                  25                  30
Arg Pro Pro Leu Leu Gly Glu Arg Arg Ser Ala Ala Glu Arg Ser Ala
             35                  40                  45
Arg Gly Gly Pro Gly Ala Ala Gln Leu Ala His Leu His Gly Ile Leu
         50                  55                  60
Arg Arg Arg Gln Leu Tyr Cys Arg Thr Gly Phe His Leu Gln Ile Leu
 65                  70                  75                  80
Pro Asp Gly Ser Val Gln Gly Thr Arg Gln Asp His Ser Leu Phe Gly
                 85                  90                  95
Ile Leu Glu Phe Ile Ser Val Ala Val Gly Leu Val Ser Ile Arg Gly
            100                 105                 110
Val Asp Ser Gly Leu Tyr Leu Gly Met Asn Asp Lys Gly Glu Leu Tyr
            115                 120                 125
Gly Ser Glu Lys Leu Thr Ser Glu Cys Ile Phe Arg Glu Gln Phe Glu
        130                 135                 140
Glu Asn Trp Tyr Asn Thr Tyr Ser Ser Asn Ile Tyr Lys His Gly Asp
145                 150                 155                 160
Thr Gly Arg Arg Tyr Phe Val Ala Leu Asn Lys Asp Gly Thr Pro Arg
                165                 170                 175
Asp Gly Ala Arg Ser Lys Arg His Gln Lys Phe Thr His Phe Leu Pro
            180                 185                 190
Arg Pro Val Asp Pro Glu Arg Val Pro Glu Leu Tyr Lys Asp Leu Leu
            195                 200                 205
Met Tyr Thr
    210
```

<210> SEQ ID NO 3
<211> LENGTH: 38
<212> TYPE: DNA
<213> ORGANISM: Artificial Sequence

```
<220> FEATURE:
<223> OTHER INFORMATION: Description of Artificial Sequence:FGF-CX
      Forward Primer

<400> SEQUENCE: 3
ctcgtcagat ctccaccatg gctcccttag ccgaagtc                              38

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence:FGF-CX
      Reverse Primer

<400> SEQUENCE: 4
ctcgtcctcg agagtgtaca tcagtaggtc cttg                                  34

<210> SEQ ID NO 5
<211> LENGTH: 424
<212> TYPE: DNA
<213> ORGANISM: Homo sapiens

<400> SEQUENCE: 5
tggatcattt aaaggggatt ctcaggcgga ggcagctata ctgcaggact ggatttcact       60
tagaaatctt ccccaatggt actatccagg gaaccaggaa agaccacagc cgatttggca     120
ttctggaatt tatcagtata gcagtgggcc tggtcagcat cgaggcgtg  acagtggac      180 tctacctcgg gatgaatgag aagggggagc tgtatggatc agaaaaacta acccaagagt    240
gtgtattcag agaacagttc gaagaaaact ggtataatac gtactcgtca aacctatata    300
agcacgtgga cactggaagg cgatactatg ttgcattaaa taaagatggg accccgagag    360
aagggactag gactaaacgg caccagaaat tcacacattt tttacctaga ccagtggacc    420
ccga                                                                 424

<210> SEQ ID NO 6
<211> LENGTH: 288
<212> TYPE: DNA
<213> ORGANISM: Homo sapiens

<400> SEQUENCE: 6
taccgaagag gctgtggtcc tgccgggtgc cctgcacgct gccgtcgggc aggatctgca      60
ggtggaagcc ggtgcggcaa tagagctgcc ggcgcgcagg atgccgtgca ggtgcgccag    120
ctgcgcagcc cccggcccgc cgcgcgcgct ccgctccgcc gcgctcctgc gctcgcccag    180
cagcggcggc cgctcccccgg caggaggcaa caggaaatgc gaacccacct gctggcccaa   240
gccctccagg ccgcccagaa agccccgac ttcggctaag ggagccat                  288

<210> SEQ ID NO 7
<211> LENGTH: 255
<212> TYPE: DNA
<213> ORGANISM: Homo sapiens

<400> SEQUENCE: 7
agtgtacatc agtaggtcct tgtacaattc tggaactctt tctggatcca ctggtctagg      60
taagaaatgt gtaaatttct gatgcctctt ggacctggcg ccatctcttg gagttccgtc    120
tttgttaagt gccacaaaat acctgcggcc agtgtctcca tgtttatata tgttagatga    180
```

-continued

```
ataggtgtta taccagttct cttcaaactg ctccctaaag atgcattcgg aagtaagttt      240
ctcctgaaag agaga                                                      255
```

<210> SEQ ID NO 8
<211> LENGTH: 106
<212> TYPE: DNA
<213> ORGANISM: Homo sapiens

<400> SEQUENCE: 8

```
ctgatccata gagttctcct ttgtcattca ttccaagata gagaccactg tccacacctc       60
taatactgac cagtcccact gccacactga tgaattccaa gatacc                    106
```

<210> SEQ ID NO 9
<211> LENGTH: 205
<212> TYPE: PRT
<213> ORGANISM: Homo sapiens

<400> SEQUENCE: 9

```
Met Ala Pro Leu Gly Glu Val Gly Asn Tyr Phe Gly Val Gln Asp Ala
  1               5                  10                  15

Val Pro Phe Gly Asn Val Pro Val Leu Pro Val Asp Ser Pro Val Leu
                 20                  25                  30

Leu Ser Asp His Leu Gly Gln Ser Glu Ala Gly Gly Leu Pro Arg Gly
             35                  40                  45

Pro Ala Val Thr Asp Leu Asp His Leu Lys Gly Ile Leu Arg Arg Arg
         50                  55                  60

Gln Leu Tyr Cys Arg Thr Gly Phe His Leu Glu Ile Phe Pro Asn Gly
 65                  70                  75                  80

Thr Ile Gln Gly Thr Arg Lys Asp His Ser Arg Phe Gly Ile Leu Glu
                 85                  90                  95

Phe Ile Ser Ile Ala Val Gly Leu Val Ser Ile Arg Gly Val Asp Ser
            100                 105                 110

Gly Leu Tyr Leu Gly Met Asn Glu Lys Gly Glu Leu Tyr Gly Ser Glu
            115                 120                 125

Lys Leu Thr Gln Glu Cys Val Phe Arg Glu Gln Phe Glu Glu Asn Trp
130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
            180                 185                 190

Asp Pro Asp Lys Val Pro Glu Leu Tyr Lys Asp Ile Leu
            195                 200                 205
```

<210> SEQ ID NO 10
<211> LENGTH: 205
<212> TYPE: PRT
<213> ORGANISM: Mus musculus

<400> SEQUENCE: 10

```
Met Ala Pro Leu Gly Glu Val Gly Ser Tyr Phe Gly Val Gln Asp Ala
  1               5                  10                  15

Val Pro Phe Gly Asn Val Pro Val Leu Pro Val Asp Ser Pro Val Leu
                 20                  25                  30

Leu Asn Asp His Leu Gly Gln Ser Glu Ala Gly Gly Leu Pro Arg Gly
             35                  40                  45
```

```
Pro Ala Val Thr Asp Leu Asp His Leu Lys Gly Ile Leu Arg Arg Arg
 50                  55                  60

Gln Leu Tyr Cys Arg Thr Gly Phe His Leu Glu Ile Phe Pro Asn Gly
 65                  70                  75                  80

Thr Ile Gln Gly Thr Arg Lys Asp His Ser Arg Phe Gly Ile Leu Glu
                 85                  90                  95

Phe Ile Ser Ile Ala Val Gly Leu Val Ser Ile Arg Gly Val Asp Ser
                100                 105                 110

Gly Leu Tyr Leu Gly Met Asn Glu Lys Gly Glu Leu Tyr Gly Ser Glu
                115                 120                 125

Lys Leu Thr Gln Glu Cys Val Phe Arg Glu Gln Phe Glu Glu Asn Trp
130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
                180                 185                 190

Asp Pro Asp Lys Val Pro Glu Leu Tyr Lys Asp Ile Leu
                195                 200                 205

<210> SEQ ID NO 11
<211> LENGTH: 205
<212> TYPE: PRT
<213> ORGANISM: Rattus norvegicus

<400> SEQUENCE: 11

Met Ala Pro Leu Gly Glu Val Gly Ser Tyr Phe Gly Val Gln Asp Ala
 1                   5                  10                  15

Val Pro Phe Gly Asn Val Pro Val Leu Pro Val Asp Ser Pro Val Leu
                 20                  25                  30

Leu Ser Asp His Leu Gly Gln Ser Glu Ala Gly Gly Leu Pro Arg Gly
                 35                  40                  45

Pro Ala Val Thr Asp Leu Asp His Leu Lys Gly Ile Leu Arg Arg Arg
 50                  55                  60

Gln Leu Tyr Cys Arg Thr Gly Phe His Leu Glu Ile Phe Pro Asn Gly
 65                  70                  75                  80

Thr Ile Gln Gly Thr Arg Lys Asp His Ser Arg Phe Gly Ile Leu Glu
                 85                  90                  95

Phe Ile Ser Ile Ala Val Gly Leu Val Ser Ile Arg Gly Val Asp Ser
                100                 105                 110

Gly Leu Tyr Leu Gly Met Asn Glu Lys Gly Glu Leu Tyr Gly Ser Glu
                115                 120                 125

Lys Leu Thr Gln Glu Cys Val Phe Arg Glu Gln Phe Glu Glu Asn Trp
130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
                180                 185                 190

Asp Pro Asp Lys Val Pro Glu Leu Tyr Lys Asp Ile Leu
                195                 200                 205
```

```
<210> SEQ ID NO 12
<211> LENGTH: 208
<212> TYPE: PRT
<213> ORGANISM: Xenopus laevis

<400> SEQUENCE: 12

Met Ala Pro Leu Ala Asp Val Gly Thr Phe Leu Gly Tyr Asp Ala
 1               5                  10                  15

Leu Gly Gln Val Gly Ser His Phe Leu Pro Pro Ala Lys Asp Ser
             20                  25                  30

Pro Leu Leu Phe Asn Asp Pro Leu Ala Gln Ser Glu Arg Leu Ser Arg
         35                  40                  45

Ser Ala Pro Ser Asp Leu Ser His Leu Gln Gly Ile Leu Arg Arg Arg
     50                  55                  60

Gln Leu Tyr Cys Arg Thr Gly Phe His Leu Gln Ile Leu Pro Asp Gly
 65                  70                  75                  80

Asn Val Gln Gly Thr Arg Gln Asp His Ser Arg Phe Gly Ile Leu Glu
                 85                  90                  95

Phe Ile Ser Val Ala Ile Gly Leu Val Ser Ile Arg Gly Val Asp Thr
                100                 105                 110

Gly Leu Tyr Leu Gly Met Asn Asp Lys Gly Glu Leu Phe Gly Ser Glu
            115                 120                 125

Lys Leu Thr Ser Glu Cys Ile Phe Arg Glu Gln Phe Glu Glu Asn Trp
        130                 135                 140

Tyr Asn Thr Tyr Ser Ser Asn Leu Tyr Lys His Gly Asp Ser Gly Arg
145                 150                 155                 160

Arg Tyr Phe Val Ala Leu Asn Lys Asp Gly Thr Pro Arg Asp Gly Thr
                165                 170                 175

Arg Ala Lys Arg His Gln Lys Phe Thr His Phe Leu Pro Arg Pro Val
            180                 185                 190

Asp Pro Glu Lys Val Pro Glu Leu Tyr Lys Asp Leu Met Gly Tyr Ser
        195                 200                 205

<210> SEQ ID NO 13
<211> LENGTH: 26
<212> TYPE: PRT
<213> ORGANISM: Homo sapiens

<400> SEQUENCE: 13

Gln Asp His Ser Leu Phe Gly Ile Leu Glu Phe Ile Ser Val Ala Val
 1               5                  10                  15

Gly Leu Val Ser Ile Arg Gly Val Asp Ser
             20                  25

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence:pSec-V5-His
      Forward Primer

<400> SEQUENCE: 14
ctcgtcctcg agggtaagcc tatccctaac                                       30

<210> SEQ ID NO 15
<211> LENGTH: 31
<212> TYPE: DNA
<213> ORGANISM: Artificial Sequence
```

```
<220> FEATURE:
<223> OTHER INFORMATION: Description of Artificial Sequence:pSec-V5-His
      Reverse Primer

<400> SEQUENCE: 15
ctcgtcgggc ccctgatcag cgggtttaaa c                              31

<210> SEQ ID NO 16
<211> LENGTH: 14
<212> TYPE: DNA
<213> ORGANISM: Artificial Sequence
<220> FEATURE:
<223> OTHER INFORMATION: Description of Artificial Sequence:
      Oligonucleotide linker

<400> SEQUENCE: 16
catggtcagc ctac                                                 14

<210> SEQ ID NO 17
<211> LENGTH: 14
<212> TYPE: DNA
<213> ORGANISM: Artificial Sequence
<220> FEATURE:
<223> OTHER INFORMATION: Description of Artificial Sequence:
      Oligonucleotide linker

<400> SEQUENCE: 17
tcgagtaggc tgac                                                 14

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:Ag81b
      Forward Primer

<400> SEQUENCE: 18
ggaccacagc ctcttcggta                                           20

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence:Ag81b
      Reverse Primer

<400> SEQUENCE: 19
tgtccacacc tctaatactg accag                                     25

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence:Ag81b Probe
      Primer

<400> SEQUENCE: 20
cccactgcca cactgatgaa ttccaa                                    26

<210> SEQ ID NO 21
<211> LENGTH: 21
<212> TYPE: DNA
<213> ORGANISM: Artificial Sequence
```

```
<220> FEATURE:
<223> OTHER INFORMATION: Description of Artificial Sequence:Ag81 Forward
      Primer

<400> SEQUENCE: 21
aggcagaagc gggagataga t                                               21

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence:Ag81 Reverse
      Primer

<400> SEQUENCE: 22
agcagcttta cctcattcac aatg                                            24

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence:Ag81 Probe
      Primer

<400> SEQUENCE: 23
ccatctacat ccaccaccag ttgcagaa                                        28

<210> SEQ ID NO 24
<211> LENGTH: 207
<212> TYPE: PRT
<213> ORGANISM: Homo sapiens

<400> SEQUENCE: 24
```

Met Ala Glu Val Gly Gly Val Phe Ala Ser Leu Asp Trp Asp Leu His
 1               5                  10                  15

Gly Phe Ser Ser Ser Leu Gly Asn Val Pro Leu Ala Asp Ser Pro Gly
                20                  25                  30

Phe Leu Asn Glu Arg Leu Gly Gln Ile Glu Gly Lys Leu Gln Arg Gly
            35                  40                  45

Ser Pro Thr Asp Phe Ala His Leu Lys Gly Ile Leu Arg Arg Arg Gln
        50                  55                  60

Leu Tyr Cys Arg Thr Gly Phe His Leu Glu Ile Phe Pro Asn Gly Thr
65                  70                  75                  80

Val His Gly Thr Arg His Asp His Ser Arg Phe Gly Ile Leu Glu Phe
                85                  90                  95

Ile Ser Leu Ala Val Gly Leu Ile Ser Ile Arg Gly Val Asp Ser Gly
            100                 105                 110

Leu Tyr Leu Gly Met Asn Glu Arg Gly Glu Leu Tyr Gly Ser Lys Lys
        115                 120                 125

Leu Thr Arg Glu Cys Val Phe Arg Glu Gln Phe Glu Glu Asn Trp Tyr
    130                 135                 140

Asn Thr Tyr Ala Ser Thr Leu Tyr Lys His Ser Asp Ser Glu Arg Gln
145                 150                 155                 160

Tyr Tyr Val Ala Leu Asn Lys Asp Gly Ser Pro Arg Glu Gly Tyr Arg
                165                 170                 175

```
Thr Lys Arg His Gln Lys Phe Thr His Phe Leu Pro Arg Pro Val Asp
            180                 185                 190

Pro Ser Lys Leu Pro Ser Met Ser Arg Asp Leu Phe His Tyr Arg
            195                 200                 205

<210> SEQ ID NO 25
<211> LENGTH: 814
<212> TYPE: DNA
<213> ORGANISM: Homo sapiens

<400> SEQUENCE: 25
agacagtgag agcttccctg ccatttcagt gcaaagtccc tccggagcga cctcagagga      60
gtaaccgggc cttaactttt tgcgctcgtt ttgctataat ttttctctat ccacctccat     120
cccaccccca caacactctt tactgggggg gtcttttgtg ttccggatct cccctccat     180 ggctccctta gccgaagtcg ggggctttct gggcggcctg gagggcttgg gccagcaggt     240
gggttcgcat ttcctgttgc ctcctgccgg ggagcggccg ccgctgctgg gcgagcgcag     300
gagcgcggcg gagcggagcg cgcgcggcgg gccgggggct gcgcagctgg cgcacctgca     360
cggcatcctg cgccgccggc agctctattg ccgcaccggc ttccacctgc agatcctgcc     420
cgacggcagc gtgcagggca cccggcagga ccacagcctc ttcggtatct tggaattcat     480
cagtgtggca gtgggactgg tcagtattag aggtgtggac agtggtctct atcttggaat     540
gaatgacaaa ggagaactct atggatcaga gaaacttact tccgaatgca tctttaggga     600
gcagtttgaa gagaactggt ataacaccta ttcatctaac atatataaac atggagacac     660
tggccgcagg tattttgtgg cacttaacaa agacggaact ccaagagatg gcgccaggtc     720
caagaggcat cagaaattta cacatttctt acctagacca gtggatccag aaagagttcc     780
agaattgtac aaggacctac tgatgtacac ttga                                 814
```

FIBROBLAST GROWTH FACTOR AND NUCLEIC ACIDS ENCODING SAME

RELATED APPLICATIONS

This application is a continuation-in-part application of U.S. Ser. No. 09/494,585, filed Jan. 31, 2000 now abandoned, which in turn claims priority to U.S. Ser. No. 60/145,899, filed Jul. 27, 1999. The contents of each of these applications are incorporated herein by reference in their entireties.

FIELD OF THE INVENTION

The present invention generally relates to nucleic acids and polypeptides. The invention relates more particularly to nucleic acids encoding polypeptides related to a member of the fibroblast growth factor family.

BACKGROUND OF THE INVENTION

The fibroblast growth factor (FGF) group of cytokines includes at least 21 members that regulate diverse cellular functions such as growth, survival, apoptosis, motility and differentiation. These molecules transduce signals via high affinity interactions with cell surface tyrosine kinase FGF receptors (FGFRs). These FGF receptors are expressed on most types of cells in tissue culture. Dimerization of FGF receptor monomers upon ligand binding has been reported to be a requisite for activation of the kinase domains, leading to receptor trans phosphorylation. FGF receptor-1 (FGFR-1), which shows the broadest expression pattern of the four FGF receptors, contains at least seven tyrosine phosphorylation sites. A number of signal transduction molecules are affected by binding with different affinities to these phosphorylation sites.

In addition to participating in normal growth and development, known FGFs have also been implicated in the generation of pathological states, including cancer. FGFs may contribute to malignancy by directly enhancing the growth of tumor cells. For example, autocrine growth stimulation through the co-expression of FGF and FGFR in the same cell has been reported to lead to cellular transformation.

SUMMARY OF THE INVENTION

The present invention is based, in part, upon the discovery of a nucleic acid encoding a novel polypeptide having homology to members of the Fibroblast Growth Factor (FGF) family of proteins. Included in the invention are polynucleotide sequences, which are named Fibroblast Grown Factor-CX (FGF-CX), and the FGF-CX polypeptides encoded by these nucleic acid sequences, and fragments, homologs, analogs, and derivatives thereof, are claimed in the invention. An example of an FGF-CX nucleic acid is SEQ ID NO:1, and an example of an FGF-CX polypeptide is a polypeptide including the amino acid sequence of SEQ ID NO:2. This amino acid sequence is encoded by the nucleic acid sequence of SEQ ID NO:1.

In one aspect, the invention includes an isolated FGF-CX polypeptide. In some embodiments, the isolated polypeptide includes the amino acid sequence of SEQ ID NO:2. In other embodiments, the invention includes a variant of SEQ ID NO:2, in which some amino acids residues, e.g., no more than 1%, 2%, 3%, 5%, 10% or 15% of the amino acid sequences of SEQ ID NO;2 are changed. In some embodiments, the isolated FGF-CX polypeptide includes the amino acid sequence of a mature form of an amino acid sequence given by SEQ ID NO:2, or a variant of a mature form of an amino acid sequence given by SEQ ID NO:2. Preferably, no more than 1%, 2%, 3%, 5%, 10% or 15% of the amino acid sequences of SEQ ID NO;2 are changed in the variant of the mature form of the amino acid sequence.

Also include in the invention is a fragment of an FGF-CX polypeptide, including fragments of variant FGF-CX polypeptides, mature FGF-CX polypeptides and variants of mature FGF-CX polypeptides, as well as FGF-CX polypeptides encoded by allelic variants and single nucleotide polymorphisms of FGF-CX nucleic acids.

In another aspect, the invention includes an isolated FGF-CX nucleic acid molecule. The FGF-CX nucleic acid molecule can include a sequence encoding any of the FGF-CX polypeptides, variants, or fragments disclosed above, or a complement to any such nucleic acid sequence. In one embodiment, the sequences include those disclosed in SEQ ID NO:1. In other embodiments, the FGF-CX nucleic acids include a sequence wherein nucleotides different from those given in SEQ ID NO:1 may be incorporated. Preferably, no more than 1%, 2%, 3%, 5%, 10%, 15%, or 20% of the nucleotides are so changed. In other embodiments, the invention includes fragments or complements of these nucleic acid sequences. Vectors and cells incorporating FGF-CX nucleic are also included in the invention.

The invention also includes antibodies that bind immunospecifically to any of the FGF-CX polypeptides described herein. The FGF-CX antibodies in various embodiments include, e.g. polyclonal antibodies, monoclonal antibodies, humanized antibodies and/or human antibodies.

The invention additionally provides pharmaceutical compositions that include a FGF-CX polypeptide, a FGF-CX nucleic acid or an FGF-CX antibody of the invention. Also included in the invention are kits that include, e.g., a FGF-CX polypeptide, a FGF-CX nucleic acid or a FGF-CX antibody.

Several methods are included in the invention. For example, a method is disclosed for determining the presence or amount of a FGF-CX polypeptide of the invention in a sample. The method includes contacting the sample with a FGF-CX antibody that binds immunospecifically to the polypeptide; and determining the presence or amount of antibody bound to said polypeptide, such that the antibody indicates the presence or amount of polypeptide in the sample.

Similarly, the invention discloses a method for determining the presence or amount of a FGF-CX nucleic acid molecule in a sample. The method includes contacting the sample with a probe that binds to the nucleic acid molecule; and determining the presence or amount of the probe bound to the nucleic acid molecule, such that the probe indicates the presence or amount of the FGF-CX nucleic acid molecule in the sample.

Also provided by the invention is a method for identifying an agent that binds to a FGF-CX polypeptide. The method includes determining whether a candidate substance binds to a FGF-CX polypeptide. Binding of a candidate substance indicates the agent is an FGF-CX polypeptide binding agent.

The invention also includes a method for identifying a potential therapeutic agent for use in treatment of a pathology. The pathology is, e.g., related to aberrant expression, aberrant processing, or aberrant physiological interactions of a FGF-CX polypeptide of the invention. This method includes providing a cell which expresses the FGF-CX polypeptide and has a property or function ascribable to the polypeptide; contacting the provided cell with a composition comprising a candidate substance; and determining whether the substance alters the property or function ascribable to the polypeptide, in comparison to a control cell. Any such substance is identified as a potential therapeutic agent. Furthermore, therapeutic agents may be identified by subjecting any potential therapeutic agent identified in this way to additional tests to identify a therapeutic agent for use in treating the pathology.

In some embodiments, the property or function relates to cell growth or cell proliferation, and the substance binds to the polypeptide, thereby modulating an activity of the polypeptide. In some embodiments, the candidate substance has a molecular weight not more than about 1500 Da. In some embodiments, the candidate substance is an antibody. The invention additionally provides any therapeutic agent identified using a method such as those described herein.

Additional important aspects of the invention relate to methods of treating or preventing a disorder associated with a FGF-CX polypeptide. The disorder may be characterized by insufficient or ineffective growth of a cell or a tissue, or by hyperplasia or neoplasia of a cell or a tissue. The method includes administering to a subject a FGF-CX polypeptide of the invention, or a FGF-CX nucleic acid of the invention, or any other Therapeutic of the invention, in an amount and for a duration sufficient to treat or prevent the disorder in said subject. In significant embodiments, the subject is a human.

The invention also includes a method for screening for a modulator of latency or predisposition to a disorder associated with aberrant expression, aberrant processing, or aberrant physiological interactions of a FGF-CX polypeptide. The method includes providing a test animal that recombinantly expresses the FGF-CX polypeptide of the invention and is at increased risk for the disorder; administering a test compound to the test animal; measuring an activity of the polypeptide in the test animal after administering the compound; and comparing the activity of the FGF-CX polypeptide in the test animal with the activity of the FGF-CX polypeptide in a control animal not administered the compound. If there is a change in the activity of the polypeptide in the test animal relative to the control animal, the test compound is a modulator of latency of or predisposition to the disorder.

The invention also provides a method for determining the presence of or predisposition to a disease associated with altered levels of a FGF-CX polypeptide or of a FGF-CX nucleic acid of the invention in a first mammalian subject. The method includes measuring the level of expression of the polypeptide or the amount of the nucleic acid in a sample from the first mammalian subject; and comparing its amount in the sample to its amount present in a control sample from a second mammalian subject known not to have, or not to be predisposed to, the disease. An alteration in the expression level of the polypeptide or the amount of the nucleic acid in the first subject as compared to the control sample indicates the presence of or predisposition to the disease.

Also provided by the invention is a method of treating a pathological state in a mammal, wherein the pathology is related to aberrant expression, aberrant processing, or aberrant physiological interactions of a FGF-CX polypeptide of the invention. The method includes administering to the mammal a polypeptide of the invention in an amount that is sufficient to alleviate the pathological state, wherein the FGF-CX polypeptide is a polypeptide having an amino acid sequence at least 85%, 90%, 95%, 96%, 97%, 98%, or even 99% identical to a polypeptide comprising an amino acid sequence of SEQ ID NO:2, or a biologically active fragment thereof. In another related method, an antibody of the invention is administered to the mammal.

In another aspect, the invention, the invention includes a method of promoting growth of cells in a subject. The method includes administering to the subject a FGF-CX polypeptide of the invention in an amount and for a duration that are effective to promote cell growth. In some embodiments, the subject is a human, and the cells whose growth is to be promoted may be chosen from among cells in the vicinity of a wound, cells in the vascular system, cells involved in hematopoiesis, cells involved in erythropoiesis, cells in the lining of the gastrointestinal tract, and cells in hair follicles.

In a further aspect, the invention provides a method of inhibiting growth of cells in a subject, wherein the growth is related to expression of a FGF-CX polypeptide of the invention. This method includes administering to the subject a composition that inhibits growth of the cells. In a highly important embodiment, the composition includes an antibody or another therapeutic agent of the invention. Significantly, the subject is a human, and the cells whose growth is to be inhibited are chosen from among transformed cells, hyperplastic cells, tumor cells, and neoplastic cells.

In a still further aspect, the invention provides method of treating or preventing or delaying a tissue proliferation-associated disorder. The method includes administering to a subject in which such treatment or prevention or delay is desired a FGF-CX nucleic acid, a FGF-CX polypeptide, or a FGF-CX antibody in an amount sufficient to treat, prevent, or delay a tissue proliferation-associated disorder in the subject.

The tissue proliferation-associated disorders diagnosed, treated, prevented or delayed using the FGF-CX nucleic acid molecules, polypeptides or antibodies can involve epithelial cells, e.g., fibroblasts and keratinocytes in the anterior eye after surgery. Other tissue proliferation-associated disorder include, e.g., tumors, restenosis, psoriasis, Dupuytren's contracture, diabetic complications, Kaposi sarcoma, and rheumatoid arthritis.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 1 is a representation of the nucleotide sequence (SEQ ID NO:1) and translated amino acid sequence (SEQ ID NO:2) of a novel FGF-CX polynucleotide and protein of the invention.

FIG. 2 is a BLASTN alignment of the nucleic acid sequence of SEQ ID NO:1 with a FGF-9-like Glia-Activating factor (GAF) sequence (SEQ ID NO:5).

FIG. 3 is a BLASTN alignment of the complementary strand of the nucleic acid sequence of SEQ ID NO:1 with three discontinuous segments (SEQ ID NOs:6–8 in panels A–C, respectively) of an extended genomic fragment of human chromosome 8 (GenBank Accession Number AB020858).

FIG. 4 is a ClustalW alignment of four vertebrate FGF-like proteins (SEQ ID NO:9–12) with the FGF-CX protein (SEQ ID NO:2) of the present invention. Black, gray and white represent identical, conserved and nonconserved residues in the alignment, respectively.

FIG. 5 is a ClustalW alignment of FGF-CX with three other FGF family members. FGF-CX (SEQ ID NO:2) was aligned with human FGF-9 (SEQ ID NO:12), human FGF-16 (SEQ ID NO:9) and Xenopus FGF-CX (SEQ ID NO:24) (Accession Numbers D14838, AB009391 and AB012615, respectively).

FIG. 6 is a BLASTP alignment of the FGF-CX polypeptide sequence (SEQ ID NO:2) with a human FGF-9 (SEQ ID NO:9) indicating identical ("l") and positive ("+") residues.

FIG. 7 is a BLASTX alignment of the FGF-CX polypeptide sequence (SEQ ID NO:2) with murine FGF-9 (SEQ ID NO:10) indicating identical ("l") and positive ("+") residues.

FIG. 8 is a BLASTX alignment of the FGF-CX polypeptide sequence (SEQ ID NO:2) with rat FGF-9 (SEQ ID NO:11) indicating identical ("l") and positive ("+") residues.

FIG. 9 is a BLASTX alignment of the FGF-CX polypeptide sequence (SEQ ID NO:2) with Xenopus XFGF-CX (SEQ ID NO:12) indicating identical ("l") and positive ("+") residues.

FIG. 11 shows a Western analysis of FGF-CX. Samples from 293 cells (Panel A) or NIH 3T3 cells (Panel B) transiently transfected with the indicated construct were examined by Western analysis using anti-V5 antibody. CM=conditioned media, SE=suramin-extracted conditioned media. Molecular mass markers are indicated on the left.

FIG. 13 presents an analysis of the FGF-CX gene (SEQ ID NO:25), including the nucleotide and deduced amino acid sequence (SEQ ID NO:2) of FGF-CX. The initiation and stop codons are in bold, and an in frame stop codon residing in the 5' UTR is underlined.

FIG. 15 present an analysis of the expression of FGF-CX obtained by real-time quantitative PCR using FGF-CX-specific TaqMan reagents. Results for normalized RNA derived from normal human tissue samples are shown in Panel A, and from tumor cell lines in Panel B. Results obtained using tumor tissues obtained directly during surgery are shown in Panels C and D.

DETAILED DESCRIPTION OF THE INVENTION

Figure 10:
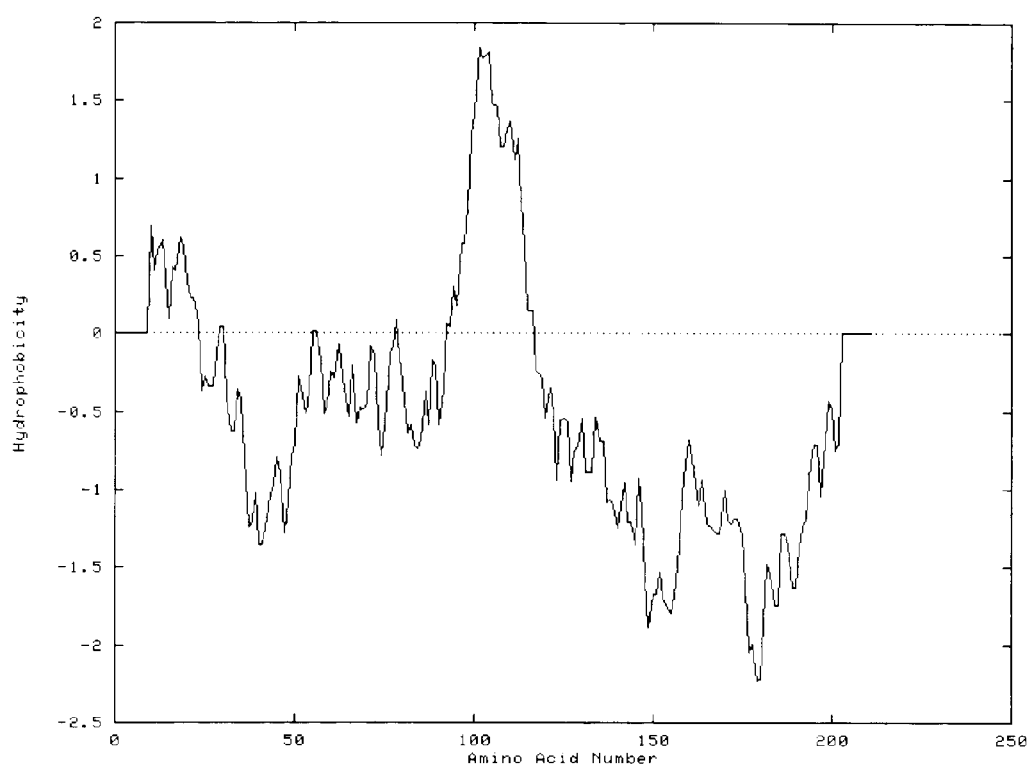
FIG. 10 is a representation of a hydropathy plot of the FGF-CX polypeptide of SEQ ID NO:2, generated with a nineteen residue window.

This invention is based in part on the discovery of novel FGF-CX nucleic acid sequences, which encode polypeptides that are members of the fibroblast growth factor (FGF) family. As used herein the designation "FGF-CX" relates to nucleic acids, polynucleotides, proteins, polypeptides, and variants, derivatives and fragments of any of them, as well as to antibodies that bind immunospecifically to any of these classes of compounds.

Previously described members of the FGF family regulate diverse cellular functions such as growth, survival, apoptosis, motility and differentiation (Szebenyi, G. & Fallon, J. F. (1999) *Int. Rev. Cytol.* 185, 45–106). These molecules transduce signals intracellularly via high affinity interactions with cell surface tyrosine kinase FGF receptors (FGFRs), four of which have been identified to date (Xu, X., Weinstein, M., Li. C. & Deng, C. (1999) *Cell Tissue Res.* 296, 33–43; Klint, P. & Claesson-Welsh, L. (1999) *Front. Biosci.* 4, 165–177). These FGF receptors are expressed on most types of cells in tissue culture. Dimerization of FGF receptor monomers upon ligand binding has been reported to be a requisite for activation of the kinase domains, leading to receptor trans phosphorylation. FGF receptor-1 (FGFR-1), which shows the broadest expression pattern of the four FGF receptors, contains at least seven tyrosine phosphorylation sites. A number of signal transduction molecules are affected by binding with different affinities to these phosphorylation sites.

FGFs also bind, albeit with low affinity, to heparin sulfate proteoglycans (HSPGs) present on most cell surfaces and extracellular matrices (ECM). Interactions between FGFs and HSPGs serve to stabilize FGF/FGFR interactions, and to sequester FGFs and protect them from degradation (Szebenyi, G. & Fallon. J. F. (1999)). Due to its growth-promoting capabilities, one member of the FGF family, FGF-7, is currently in clinical trials for the treatment of chemotherapy-induced mucositis (Danilenko, D. M. (1999) *Toxicol. Pathol.* 27, 64–71).

In addition to participating in normal growth and development, known FGFs have also been implicated in the generation of pathological states, including cancer (Basilico, C & Moscatelli, D. (1992) *Adv. Cancer Res.* 59, 115–165). FGFs may contribute to malignancy by directly enhancing the growth of tumor cells. For example, autocrine growth stimulation through the co-expression of FGF and FGFR in the same cell leads to cellular transformation (Matsumoto-Yoshitomi, S., Habashita. J. Nomura, C. Kuroshima, K. & Kurokawa, T. (1997) *Int. J. Cancer* 71, 442–450). Likewise, the constitutive activation of FGFR via mutation or rearrangement leads to uncontrolled proliferation (Lorenzi, M., Horii, Y., Yamanaka, R., Sakaguchi, K. & Miki. T. (1996) *Proc. Natl. Acad. Sci. USA.* 93, 8956–8961; Li, Y., Mangasarian, K., Mansukhani, A. & Basilico, C. (1997) *Oncogene* 14, 1397–1406). Furthermore, some FGFs are angiogenic (Gerwins, P., Skoldenberg, E. & Claesson-Welsh, L.

(2000) *Crit. Rev. Oncol. Hematol.* 34, 185–194). Such FGFs may contribute to the tumorigenic process by facilitating the development of the blood supply needed to sustain tumor growth. Not surprisingly, at least one FGF is currently under investigation as a potential target for cancer therapy (Gasparini. G. (1999) *Drugs* 58, 17–38).

Expression of FGFs and their receptors in the brains of perinatal and adult mice has been examined. Messenger RNA all FGF genes, with the exception of FGF-4, is detected in these tissues. FGF-3, FGF-6, FGF-7 and FGF-8 genes demonstrate higher expression in the late embryonic stages than in postnatal stages, suggesting that these members are involved in the late stages of brain development. In contrast, expression of FGF-1 and FGF-5 increased after birth. In particular, FGF-6 expression in perinatal mice has been reported to be restricted to the central nervous system and skeletal muscles, with intense signals in the developing cerebrum in embryos but in cerebellum in 5-day-old neonates. FGF-receptor (FGFR)-4, a cognate receptor for FGF-6, demonstrate similar spatiotemporal expression, suggesting that FGF-6 and FGFR-4 plays significant roles in the maturation of nervous system as a ligand-receptor system. According to Ozawa et al., these results strongly suggest that the various FGFs and their receptors are involved in the regulation of a variety of developmental processes of brain, such as proliferation and migration of neuronal progenitor cells, neuronal and glial differentiation, neurite extensions, and synapse formation.

Glia-activating factor (GAF.), another FGF family member, is a heparin-binding growth factor that was purified from the culture supernatant of a human glioma cell line. See, Miyamoto et al., 1993, *Mol Cell Biol* 13(7): 4251–4259. GAF shows a spectrum of activity slightly different from those of other known growth factors, and is designated as FGF-9. The human FGF-9 cDNA encodes a polypeptide of 208 amino acids. Sequence similarity to other members of the FGF family was estimated to be around 30%. Two cysteine residues and other consensus sequences found in other family members were also well conserved in the FGF-9 sequence. FGF-9 was found to have no typical signal sequence in its N terminus like those in acidic FGF and basic FGF.

Acidic FGF and basic FGF are known not to be secreted from cells in a conventional manner. However, FGF-9 was found to be secreted efficiently from cDNA-transfected COS cells despite its lack of a typical signal sequence. It could be detected exclusively in the culture medium of cells. The secreted protein lacked no amino acid residues at the N terminus with respect to those predicted by the cDNA sequence, except the initiation methionine. The rat FGF-9 cDNA was also cloned, and the structural analysis indicated that the FGF-9 gene is highly conserved.

The present invention provides a novel human FGF as well as its corresponding cDNA. The protein product of this gene has been shown to exhibit growth stimulatory and oncogenic properties. Furthermore, overexpression of the FGF mRNA was noted in certain specific cancer cell lines. These observations suggest that the novel FGF may be of use by serving as an excellent target in the treatment of human malignancy.

The invention also includes mature FGF-CX polypeptides, variants of mature FGF-CX polypeptides, fragments of mature and mature variant FGF-CX polypeptides, and nucleic acids encoding these polypeptides and fragments. As used herein, a "mature" form of a FGF-CX polypeptide or protein disclosed in the present invention is the product of a naturally occurring polypeptide or precursor form or proprotein. The naturally occurring polypeptide, precursor or proprotein includes, by way of nonlimiting example, the full length gene product, encoded by the corresponding gene. In some embodiments, the mature form include an FGF-CX polypeptide, precursor or proprotein encoded by an open reading frame described herein. The product "mature" form can arise, e.g., as a result of one or more naturally occurring processing steps as they may take place within the cell, or host cell, in which the gene product arises.

Examples of such processing steps leading to a "mature" form of a polypeptide or protein include the cleavage of the N-terminal methionine residue encoded by the initiation codon of an open reading frame, or the proteolytic cleavage of a signal peptide or leader sequence. Thus a mature form arising from an FGF-CX precursor polypeptide or protein that has residues 2 to N, where residue 1 is the N-terminal methionine, would have residues 2 through N remaining after removal of the N-terminal methionine. Alternatively, a mature form arising from a precursor polypeptide or protein having residues 1 to N, in which an N-terminal signal sequence from residue 1 to residue M is cleaved, would have the residues from residue M+1 to residue N remaining. Additionally, a "mature" protein or fragment may arise from a cleavage event other than removal of an initiating methionine or removal of a signal peptide. Further as used herein, a "mature" form of an FGF-CX polypeptide or protein may arise from a step of post-translational modification other than a proteolytic cleavage event. Such additional processes include, by way of non-limiting example, glycosylation, myristoylation or phosphorylation. In general, a mature polypeptide or protein may result from the operation of only one of these processes, or a combination of any of them.

As used herein, "identical" residues correspond to those residues in a comparison between two sequences where the equivalent nucleotide base or amino acid residue in an alignment of two sequences is the same residue. Residues are alternatively described as "similar" or "positive" when the comparisons between two sequences in an alignment show that residues in an equivalent position in a comparison are either the same amino acid or a conserved amino acid as defined below.

Included within the invention are FGF-CX nucleic acids, isolated nucleic acids that encode FGF-CX polypeptide or a portion thereof, FGF-CX polypeptides, vectors containing these nucleic acids, host cells transformed with the FGF-CX nucleic acids, anti-FGF-CX antibodies, and pharmaceutical compositions. Also disclosed are methods of making FGF-CX polypeptides, as well as methods of screening, diagnosing, treating conditions using these compounds, and methods of screening compounds that modulate FGF-CX polypeptide activity. Table 1 below delineates the sequence descriptors that are used throughout the invention.

The FGF-CX nucleic acids and polypeptides, as well as FGF-CX antibodies, therapeutic agents and pharmaceutical compositions discussed herein, are useful, inter alia, in treating tissue proliferation-associated disorders. These tissue proliferation-associated disorders can include disorders affecting

TABLE 1

| SEQ ID NO | SEQUENCE DESCRIPTOR |
|---|---|
| 1 | Human FGF-CX nucleotide sequence |
| 2 | Human FGF-CX polypeptide sequence |
| 3 | FGF-CX Forward primer |
| 4 | FGF-CX Reverse primer |

TABLE 1-continued

| SEQ ID NO | SEQUENCE DESCRIPTOR |
|---|---|
| 5 | Glia Activating Factor (GAF) |
| 6 | Human genomic fragment-bp 15927–16214 |
| 7 | Human genomic fragment-bp 7257–7511 |
| 8 | Human genomic fragment-bp 9837–9942 |
| 9 | Human FGF-9 |
| 10 | Mouse FGF-9 |
| 11 | Rat FGF-9 |
| 12 | Xenopus FGF-CX |
| 13 | Human FGF-CX hydrophobic domain (aa 90–115) |
| 14 | PSec-V5-His Forward |
| 15 | PSec-V5-His Reverse |
| 16 | PSETA linker |
| 17 | PSETA linker |
| 18 | TaqMan expression analysis forward primer |
| 19 | TaqMan expression analysis reverse primer |
| 20 | TaqMan expression analysis probe | epithelial cells, e.g., fibroblasts and keratinocytes in the anterior eye after surgery. Other tissue proliferation-associated disorder include, e.g., tumors, restenosis, psoriasis, Dupuytren's contracture, diabetic complications, Kaposi sarcoma, and rheumatoid arthritis.

Included in the invention is a nucleotide sequence (SEQ ID NO:1) encoding a novel fibroblast growth factor designated fibroblast growth factor-20X (FGF-CX) (see FIG. 1; SEQ ID NO:1). This coding sequence was identified in human genomic DNA sequences. The disclosed DNA sequence has 633 bases that encode a polypeptide predicted to have 211 amino acid residues (SEQ ID NO:2). The predicted molecular weight of FGF-CX, based on the sequence shown in FIG. 1 and SEQ ID NO:2, is 23498.4 Da.

The FGF-CX nucleic acid sequence was used as a query nucleotide sequence in a BLASTN search to identify related nucleic acid sequences. The FGF-CX nucleotide sequence has a high similarity to murine fibroblast growth factor 9 (FGF-9) (392 of 543 bases identical, or 72%; GenBank Accession Number S82023) and to human DNA encoding glia activating factor (GAP) (385 of 554 bases identical, or 69%; GenBank Accession Number E05822, also termed FGF-9). In addition, FGF-CX was found to have a comparable degree of identity (311 of 424 bases identical, or 73%) to a GAF sequence (SEQ ID NO:5) disclosed by Naruo et al. in Japanese Patent: JP 1993301893 entitled "Glia-Activating Factor And Its Production" (see FIG. 2).

To verify that the open reading frame (ORF) identified by genomic mining was correct, PCR amplification was used to obtain a cDNA corresponding to the predicted genomic clone. The nucleotide sequence of the obtained product precisely matches that of the predicted gene (see Example 1).

The protein encoded by the cDNA is most closely related to Xenopus FGF-20X (designated XFGF-CX or XFGF-20X herein), as well as to human FGF-9 and human FGF-16 (80%, 70% and 64% amino acid identity, respectively; see FIGS. 4 and 5). Based on the strong homology with XFGF-CX, the gene identified in the present disclosure is believed to represent its human ortholog, and is named FGF-CX herein.

A BLASTP alignment of the first 208 amino acids of the FGF-CX polypeptide sequence (SEQ ID NO:2) with a human FGF-9 (SEQ ID NO:9) is shown in FIG. 6. See, SWISSPROT Accession Number P31371 for Glia-Activating Factor Precursor (GAF) (Fibroblast Growth Factor-9); Miyamoto et al. 1993 Mol. Cell. Biol. 13:4251–4259; and Naruo et al. 1993 J. Biol. Chem. 268:2857–2864. BLASTX alignments of the first 208 amino acids of the FGF-CX polypeptide (SEQ ID NO:2, translated from SEQ ID NO:1) with the mouse FGF-9 (SEQ ID NO:10) and rat FGF-9) (SEQ ID NO:11) sequences are shown in FIGS. 7 and 8, respectively. See, SWISSPROT Accession Number P54130 for Glia-Activating Factor Precursor (GAF) (Fibroblast Growth Factor-9), Santos-Ocampo et al., 1996 J. Biol. Chem. 271:1726–1731, for mouse FGF-9; and SWISSPROT Accession Number P36364 Glia-Activating Factor Precursor (GAF) (Fibroblast Growth Factor-9) (FGF-9), Miyamoto, 1993 Mol. Cell. Biol. 13:4251–4259, for rat FGF-9. As indicated by the bars ("|") in FIGS. 5–7, FGF-9 sequences of all three species have 147 of 208 residues identical with FGF-CX (SEQ ID NO:2), for an overall sequence identity of 70%. In addition, 170 of 208 residues are positive to the sequence of FGF-CX (SEQ ID NO:2), for an overall percentage of positive residues of 81%. Positive residues include those residues that are either identical ("|") or have a conservative amino acid substitution ("+") in the same relative position of the compared sequences when aligned, see below.

The full length FGF-CX polypeptide (SEQ ID NO:2) was also aligned by BLASTX with Xenopus XFGF-CX (SEQ ID NO:12). As shown in FIG. 9. FGF-CX has 170 of 211 (80%) identical residues, and 189 of 211 (89%) positive residues compared with Xenopus XFGF-CX. Xenopus XFGF-CX was obtained recently from a cDNA library prepared at the tailbud stage using the product of degenerate PCR performed with primers based on mammalian FGF-9s as a probe. See, Koga et al., 1999 Biochem Biophys Res Commun. 261(3):756–765. The deduced 208 amino acid sequence of the XFGF-CX open reading frame contains a motif characteristic of the FGF family. XFGF-CX has a 73.1% overall similarity to XFGF-9 but differs from XFGF-9 in its amino-terminal region (33.3% similarity). This resembles the similarity seen for the presently disclosed SEQ ID NO:2 with respect to various mammalian FGF-9 and FGF-16 sequences, including human (see above). See, FIGS. 4, 5 and 7–9.

The polypeptide sequence in FIG. 1 (SEQ ID NO:2) is predicted by the program PSORT to have high probabilities for sorting through the membrane of the endoplasmic reticulum and of the microbody (peroxisome). In addition, although it does not have a predicted cleavable signal sequence at its N-terminus, the hydropathy plot in FIG. 10 shows that FGF-CX has a prominent hydrophobic segment at amino acid positions about 90 to about 115 (SEQ ID NO:13). This single hydrophobic region is known to be a sorting signal in other members of the FGF family. Accordingly, a polypeptide that includes the amino acids of SEQ ID NO:13 is useful as a sorting signal, allowing secretion through various cellular membranes, such as the endoplasmic reticulum, the Golgi membrane or the plasma membrane.

Figure 12:
FIG. 12 shows a Western analysis of FGF-CX protein secreted by 293 cells.

FGF-CX lacks a classical amino-terminal signal sequence as predicted by PSORT (Nakai, K & Kanehisa, M. (1992) Genomics 14, 897–911) and SIGNALP (Nielsen, H., Engelbrecht, J., Brunak, S. & von Heijne, G. (1997) Protein Eng. 10, 1–6) computer algorithms, just as found for some of its closest human family members (e.g. FGF-9 and FGF-16). Nonetheless, both FGF-9 and FGF-16 are secreted (Matsumoto-Yoshitomi, S., Habashita, J., Nomura, C., Kuroshima, K. & Kurokawa, T. (1997) Int. J. Cancer 71, 442–450; Miyake, A., Konishi, M. Martin, F. H., Hernday, N. A., Ozaki, K., Yamamoto, S., Mikami, T., Arakawa, T. & Itoh, N. (1998) Biochem. Biophys. Res. Comm. 243, 148–152;

Miyakawa, K., Hatsuzawa, K., Kurokawa. T. Asada, M., Kuroiwa, T. & Inamura, T. (1999) *J. Biol. Chem.* 274, 29352–29357; Revest, J.-M. DeMoerlooze, L & Dickson, C. (2000) *J Biol. Chem.* 275, 8083–8090). To determine whether FGF-CX is also secreted, the cDNA encoding the full length FGF-CX protein was subcloned into a mammalian expression vector designated pFGF-CX. The protein expressed when human embryonic kidney 293 cells are transfected with this vector is found in the conditioned medium, and exhibits a band detected by an antibody to a C-terminal V5 epitope, with an apparent molecular weight in a Western blot of ~27 kDa (FIG. 11, Example 7). An additional portion of the expressed protein is released from sequestration on the 293 cells by treatment with a substance that inhibits interaction with heparin sulfate proteoglycan (HSPG). The protein released in this way also exhibits a similar Western blot pattern (FIG. 11). Similarly when the protein is expressed in HEK293 cells from a recombinant plasmid incorporating an Ig Kappa signal sequence, a band is detected by Western blot with an apparent molecular weight of approximately 34 kDa (FIG. 12, Example 5).

ClustalW multiple protein alignments (Thompson, J. D., Higgins. D. G. & Gibson, T. J. (1994) *Nucleic Acids Res.* 22, 4673–4680) for several vertebrate FGF-like proteins, including the FGF-CX of the present invention, are shown in FIGS. 4 and 5. The three mammalian proteins (SEQ ID NOs:9–11) resemble each other very closely but differ considerably from the FGF-CX protein of the present invention (SEQ ID NO:2). Also, the *Xenopus* XFGF-CX (SEQ ID NO:12) and the sequence of SEQ ID NO:2 resemble each other more closely than those of FGF-9. The internal hydrophobic domain involved in FGF-9 secretion (Miyakawa, K., Hatsuzawa, K., Kurokawa, T., Asada, M., Kuroiwa, T. & Inamura, T. (1999) *J. Biol Chem.* 274, 29352–29357) spans residues 95–120 of the FGF-9 sequence. (See FIG. 10 for a hydropathy plot of FGF-CX.)

The expression of XFGF-20 and of *Xenopus* FGF-9 are distinct from each other. XFGF-20 mRNA is expressed in diploid cells, in embryos at and after the blastula stage, and specifically in the stomach and testis of adults, whereas XFGF-9 mRNA is expressed maternally in eggs and in many adult tissues. Koga et al., above. Correct expression of XFGF-20 during gastrulation appears to be required for the formation of normal head structures in *Xenopus laevis*. When XFGF-20 mRNA was overexpressed in early embryos, gastrulation was abnormal and development of anterior structures was suppressed. See, Koga et al., above. In such embryos, expression of the Xbra transcript, among those tested, was suppressed during gastrulation, indicating that expression of the Xbra gene mediates XFGF-CX effects. See, Koga et al., above.

The expression patterns of the related XFGF-9 polypeptide in proliferating tissues, (including, e.g. ova, testis, stomach, and multiple tissues in the maternal frog), suggests a role for XFGF-20 in the maintenance of tissues that normally undergo regeneration in a functioning organism.

It is shown in Example 8 that FGF-CX mRNA is expressed in normal cerebellum, as well as in several human tumor cell lines including carcinomas of the lung, stomach and colon but not in the corresponding normal tissues. The lack of FGF-CX expression in normal lung, stomach and colon, and its presence in tumor lines from these tissues, indicates that these cancer cell lines apparently overexpress FGF-CX in an inappropriate fashion. The chromosomal region to which FGF-CX maps is commonly altered in colorectal, lung and gastric carcinomas (Emi. M. Fujiwara, Y., Nakajima, T. Tsuchiya, E., Tsuda. H., Hirohashi. S., Maeda, Y., Tsuruta, K., Miyaki, M. & Nakamura, Y. (1992) *Cancer Res.* 52, 5368–5372; Baffa, R. Santoro, R., Bullrich, F., Mandes, B., Ishii, H. & Croce, C. M. (2000) *Clin. Cancer Res.* 6, 1372–1377). It is possible that the establishment of an FGF-CX-driven autocrine growth loop in these cells contributes to their initial tumorigenic conversion and/or to their subsequent expansion. This scenario is supported by the finding that the generation of an FGF-CX-driven autocrine loop in NIH 3T3 cells activates their tumorigenic potential (see Example 11). It is also possible that FGF-CX secretion by tumor cells stimulates their in vivo growth via paracrine effects on stromal cells.

Figure 19:
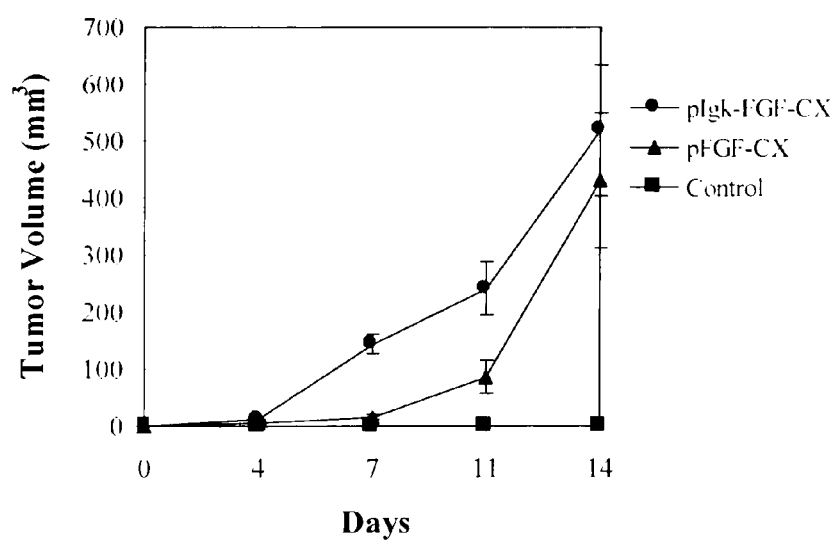
FIG. 19 presents a graph representing the tumorigenic activity of FGF-CX. NIH 3T3 cells stably transfected with the indicated constructs were injected into the subcutis of athymic nude mice and examined for tumor formation over a two week period. A minimum of 4 animals was used for each data point.

Expression of heterologous FGF-CX in NIH 3T3 cells is found to induce their transformation and tumorigenicity (see Example 11). These effects are mediated by both native FGF-CX (construct pFGF-CX) and FGF-CX expressed with a heterologous Igκ signal sequence at its amino-terminus (construct pIgκ-FGF-CX). However, it should be noted that pIgκ-FGF-CX is more oncogenically active than pFGF-CX, as evidenced by its greater in vitro transforming ability (data not shown) and in vivo tumorigenicity (FIG. 19). The superior oncogenicity of pIgκ-FGF-CX relative to pFGF-CX is likely due to the fact that pIgκ-FGF-CX produces significantly more secreted FGF-CX protein than does pFGF-CX in NIH 3T3 cells (FIG. 11B).

Like FGF-CX, other FGFs have been shown to transform cells following ectopic expression, and in some cases the blockade of FGF signaling has been shown to suppress cell transformation (Matsumoto-Yoshitomi, S. Habashita, J., Nomura, C., Kuroshima, K. & Kurokawa, T. (1997) *Int. J. Cancer* 71, 442–450; Li, Y., Basilico, C. & Mansukhani, A. (1994) *Mol. Cell. Biol.* 14, 7660–7669).

Based on the properties of FGF-CX described herein, as well as on the similarities with the effects found for related FGF proteins, it is believed that FGF-CX plays an important role in human malignancy. For these reasons, the FGF-CX polypeptides, nucleic acids and antibodies disclosed herein are useful in methods of diagnosing the presence or amounts of these compositions, in screening for and identifying therapeutic agents related to FGF-CX-associated pathologies, and in methods of treatment of various kinds of malignancy.

FGF-CX Nucleic Acids

The nucleic acids of the invention include those that encode a FGF-CX or FGF-CX-like protein. Among these nucleic acids is the nucleic acid whose sequence is provided in FIG. 1 and SEQ ID NO:1, or a fragment thereof. The FGF-CX nucleic acid can have the nucleotide sequence of a genomic FGF-CX nucleic acid, or of a cDNA. Additionally, the invention includes mutant or variant nucleic acids of SEQ ID NO:1, or a fragment thereof, any of whose bases may be changed from the corresponding base shown in FIG. 1 while still encoding a protein that maintains its FGF-CX-like activities and physiological functions. The invention further includes the complement of the nucleic acid sequence of SEQ ID NO:1, including fragments, derivatives, analogs and homolog thereof. Examples of the complementary strand of portions of FGF-CX are shown in FIG. 3. The invention additionally includes nucleic acids or nucleic acid fragments, or complements thereto, whose structures include chemical modifications.

One aspect of the invention pertains to isolated nucleic acid molecules that encode FGF-CX proteins or biologically active portions thereof. Also included are nucleic acid fragments sufficient for use as hybridization probes to identify FGF-CX-encoding nucleic acids (e.g., FGF-CX mRNA) and fragments for use as polymerase chain reaction (PCR)

primers for the amplification or mutation of FGF-CX nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but preferably is double-stranded DNA.

"Probes" refer to nucleic acid sequences of variable length, preferably between at least about 10 nucleotides (nt), 100 nt, or as many as about, e.g., 6,000 nt, depending on use. Probes are used in the detection of identical, similar, or complementary nucleic acid sequences. Longer length probes are usually obtained from a natural or recombinant source, are highly specific and much slower to hybridize than oligomers. Probes may be single- or double-stranded and designed to have specificity in PCR, membrane-based hybridization technologies, or ELISA-like technologies.

An "isolated" nucleic acid molecule is one that is separated from other nucleic acid molecules that are present in the natural source of the nucleic acid. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated FGF-CX nucleic acid molecule can contain less than about 50 kb, 25 kb, 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid molecule of the present invention, e.g. a nucleic acid molecule having the nucleotide sequence of SEQ ID NO:1, or a complement of any of this nucleotide sequence, can be isolated using standard molecular biology techniques and the sequence information provided herein. Using all or a portion of the nucleic acid sequence of SEQ ID NO:1 as a hybridization probe, FGF-CX nucleic acid sequences can be isolated using standard hybridization and cloning techniques (e.g., as described in Sambrook et al., eds., MOLECULAR CLONINGµ: A LABORATORY MANUAL $2^{nd}$ Ed., Cold Spring Harbor Laboratory Press, Cold Spring Harbor, N.Y., 1989; and Ausubel, et al., eds., CURRENT PROTOCOLS IN MOLECULAR BIOLOGY, John Wiley & Sons, New York, N.Y. 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to FGF-CX nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, preferably about 15 nt to 30 nt in length. In one embodiment, an oligonucleotide comprising a nucleic acid molecule less than 100 nt in length would further comprise at lease 6 contiguous nucleotides of SEQ ID NO:1, or a complement thereof. Oligonucleotides may be chemically synthesized and may be used as probes.

In another embodiment, an isolated nucleic acid molecule of the invention comprises a nucleic acid molecule that is a complement of the nucleotide sequence shown in SEQ ID NO:1. In another embodiment, an isolated nucleic acid molecule of the invention comprises a nucleic acid molecule that is a complement of the nucleotide sequence shown in SEQ ID NO:1, or a portion of this nucleotide sequence. A nucleic acid molecule that is complementary to the nucleotide sequence shown in SEQ ID NO:1 is one that is sufficiently complementary to the nucleotide sequence shown in SEQ ID NO:1 that it can hydrogen bond with little or no mismatches to the nucleotide sequence shown in SEQ ID NO:1, thereby forming a stable duplex.

As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, van der Waals, hydrophobic interactions, etc. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Moreover, the nucleic acid molecule of the invention can comprise only a portion of the nucleic acid sequence of SEQ ID NO:1, e.g. a fragment that can be used as a probe or primer, or a fragment encoding a biologically active portion of FGF-CX. Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 70%, 80%, 85%, 90%, 95%, 98, or even 99% identity (with a preferred identity of 80–99%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, et al., CURRENT PROTOCOLS IN MOLECULAR BIOLOGY, John Wiley & Sons, New York, N.Y., 1993, and below. An exemplary program is the Gap program (Wisconsin Sequence Analysis Package, Version 8 for UNIX. Genetics Computer Group, University Research Park, Madison, Wis.) using the default settings, which uses the algorithm of Smith and Waterman (Adv. Appl. Math., 1981, 2: 482–489, which is incorporated herein by reference in its entirety).

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of FGF-CX polypeptide. Isoforms can be expressed in different tissues of the same organism as a result of, for example, alternative splicing of RNA. Alternatively, isoforms can be encoded by different genes. In the present invention, homologous nucleotide sequences include nucleotide sequences encoding for a FGF-CX polypeptide of species other than humans, including, but not limited to, mammals, and thus can include, e.g., mouse, rat, rabbit, dog, cat cow, horse, and other organisms. Homologous nucleotide sequences also include, but are not limited to, naturally occurring allelic variations and mutations of the nucleotide sequences set forth herein. A homologous nucleotide sequence does not, however, include the nucleotide sequence encoding human FGF-CX protein. Homologous nucleic acid sequences include those nucleic acid sequences that encode conservative amino acid substitutions (see below) in SEQ ID NO:2, as well as a polypeptide having FGF-CX activity. Biological activities of the FGF-CX proteins are described below. A homologous amino acid sequence does not encode the amino acid sequence of a human FGF-CX polypeptide.

The nucleotide sequence determined from the cloning of the human FGF-CX gene allows for the generation of probes and primers designed for use in identifying and/or cloning FGF-CX homologues in other cell types, e.g., from other tissues, as well as FGF-CX homologues from other mammals. The probe/primer typically comprises a substantially purified oligonucleotide. The oligonucleotide typically comprises a region of nucleotide sequence that hybridizes under stringent conditions to at least about 12, 25, 50, 100, 150, 200, 250, 300, 350 or 400 or more consecutive sense strand nucleotide sequence of SEQ ID NO:1; or an anti-sense strand nucleotide sequence of SEQ ID NO:1; or of a naturally occurring mutant of SEQ ID NO:1.

Probes based on the human FGF-CX nucleotide sequence can be used to detect transcripts or genomic sequences encoding the same or homologous proteins. In various embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a FGF-CX protein, such as by measuring a level of a FGF-CX-encoding nucleic acid in a sample of cells from a subject e.g., detecting FGF-CX mRNA levels or determining whether a genomic FGF-CX gene has been mutated or deleted.

"A polypeptide having a biologically active portion of FGF-CX" refers to polypeptides exhibiting activity similar, but not necessarily identical to, an activity of a polypeptide of the present invention, including mature forms, as measured in a particular biological assay, with or without dose dependency. A nucleic acid fragment encoding a "biologically active portion of FGF-CX" can be prepared by isolating a portion of SEQ ID NO:1, that encodes a polypeptide having a FGF-CX biological activity (biological activities of the FGF-CX proteins are described below), expressing the encoded portion of FGF-CX protein (e.g., by recombinant expression in vitro) and assessing the activity of the encoded portion of FGF-CX. For example, a nucleic acid fragment encoding a biologically active portion of FGF-CX can optionally include an ATP-binding domain. In another embodiment, a nucleic acid fragment encoding a biologically active portion of FGF-CX includes one or more regions.

FGF-CX Variants

The invention further encompasses nucleic acid molecules that differ from the nucleotide sequences shown in FIG. 1 due to degeneracy of the genetic code. These nucleic acids thus encode the same FGF-CX protein as that encoded by the nucleotide sequence shown in SEQ ID NO:1. In another embodiment, an isolated nucleic acid molecule of the invention has a nucleotide sequence encoding a protein having an amino acid sequence shown in SEQ ID NO:2.

In addition to the human FGF-CX nucleotide sequence shown in SEQ ID NO:1, it will be appreciated by those skilled in the art that DNA sequence polymorphisms that lead to changes in the amino acid sequences of FGF-CX may exist within a population (e.g., the human population). Such genetic polymorphism in the FGF-CX gene may exist among individuals within a population due to natural allelic variation. As used herein, the terms "gene" and "recombinant gene" refer to nucleic acid molecules comprising an open reading frame encoding a FGF-CX protein, preferably a mammalian FGF-CX protein. Such natural allelic variations can typically result in 1–5% variance in the nucleotide sequence of the FGF-CX gene. Any and all such nucleotide variations and resulting amino acid polymorphisms in FGF-CX that are the result of natural allelic variation and that do not alter the functional activity of FGF-CX are intended to be within the scope of the invention.

Moreover, nucleic acid molecules encoding FGF-CX proteins from other species, and thus that have a nucleotide sequence that differs from the human sequence of SEQ ID NO:1, are intended to be within the scope of the invention. Nucleic acid molecules corresponding to natural allelic variants and homologues of the FGF-CX cDNAs of the invention can be isolated based on their homology to the human FGF-CX nucleic acids disclosed herein using the human cDNAs, or a portion thereof, as a hybridization probe according to standard hybridization techniques under stringent hybridization conditions. For example, a soluble human FGF-CX cDNA can be isolated based on its homology to human membrane-bound FGF-CX. Likewise, a membrane-bound human FGF-CX cDNA can be isolated based on its homology to soluble human FGF-CX.

Accordingly, in another embodiment, an isolated nucleic acid molecule of the invention is at least 6 nucleotides in length and hybridizes under stringent conditions to the nucleic acid molecule comprising the nucleotide sequence of SEQ ID NO:1. In another embodiment, the nucleic acid is at least 10, 25, 50, 100, 250, 500 or 750 nucleotides in length. In another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding FGF-CX proteins derived from species other than human) or other related sequences (e.g., paralogs) can be obtained by low, moderate or high stringency hybridization with all or a portion of the particular human sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions such as described above are known to those skilled in the art and can be found in CURRENT PROTOCOLS IN MOLECULAR BIOLOGY, John Wiley & Sons, N.Y. (1989). 6.3.1–6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions is hybridization in a high salt buffer comprising 6×SSC, 50 mM Tris-HCl (pH 7.5), 1 mM EDTA, 0.02% PVP, 0.020% Ficoll, 0.02% BSA, and 500 mg/ml denatured salmon sperm DNA at 65° C. This hybridization is followed by one or more washes in 0.2×SSC, 0.010% 0 BSA at 50° C. An isolated nucleic acid molecule of the invention that hybridizes under stringent conditions to the sequence of SEQ ID NO:1 corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein).

Homologs (i.e., nucleic acids encoding FGF-CX proteins derived from species other than human) or other related sequences (e.g. paralogs) can be obtained by low, moderate or high stringency hybridization with all or a portion of the particular human sequence as a probe using methods well known in the art for nucleic acid hybridization and cloning.

In a second embodiment, a nucleic acid sequence that is hybridizable to the nucleic acid molecule comprising the nucleotide sequence of SEQ ID NO:1, or fragments, analogs or derivatives thereof, under conditions of moderate stringency is provided. A non-limiting example of moderate stringency hybridization conditions are hybridization in 6×SSC, 5× Denhardt's solution. 0.5% SDS and 100 mg/ml denatured salmon sperm DNA at 55° C., followed by one or more washes in 1×SSC, 0.1% SDS at 37° C. Other conditions of moderate stringency that may be used are well known in the art. See, e.g., Ausubel et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY.

In a third embodiment, a nucleic acid that is hybridizable to the nucleic acid molecule comprising the nucleotide sequence of SEQ ID NO:1, or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY; Shilo and Weinberg, 1981, Proc Natl Acad Sci USA 78: 6789–6792.

Conservative Mutations

In addition to naturally-occurring allelic variants of the FGF-CX sequence that may exist in the population, the skilled artisan will further appreciate that changes can be introduced by mutation into the nucleotide sequence of SEQ ID NO:1, thereby leading to changes in the amino acid sequence of the encoded FGF-CX protein, without altering the functional ability of the FGF-CX protein. For example, nucleotide substitutions leading to amino acid substitutions at "non-essential" amino acid residues can be made in the sequence of SEQ ID NO:1. A "non-essential" amino acid residue is a residue that can be altered from the wild-type sequence of FGF-CX without altering the biological activity, whereas an "essential" amino acid residue is required for biological activity. For example, amino acid residues that are conserved among the FGF-CX proteins of the present invention, are predicted to be particularly unamenable to alteration.

In addition, amino acid residues that are conserved among FGF family members, as indicated by the alignment presented as FIG. 4, are predicted to be less amenable to alteration. For example, FGF-CX proteins of the present invention can contain at least one domain that is a typically conserved region in FGF family members, i.e., FGF-9 and XFGF-CX proteins, and FGF-CX homologs. As such, these conserved domains are not likely to be amenable to mutation. Other amino acid residues, however, (e.g., those that are not conserved or only semi-conserved among members of the FGF proteins) may not be as essential for activity and thus are more likely to be amenable to alteration.

Another aspect of the invention pertains to nucleic acid molecules encoding FGF-CX proteins that contain changes in amino acid residues that are not essential for activity. Such FGF-CX proteins differ in amino acid sequence from SEQ ID NO:2, yet retain biological activity. In one embodiment, the isolated nucleic acid molecule comprises a nucleotide sequence encoding a protein, wherein the protein comprises an amino acid sequence at least about 75% homologous to the amino acid sequence of SEQ ID NO:2. Preferably, the protein encoded by the nucleic acid is at least about 80% homologous to SEQ ID NO:2, more preferably at least about 90%, 95%, 98%, and most preferably at least about 99% homologous to SEQ ID NO:2.

An isolated nucleic acid molecule encoding a FGF-CX protein homologous to the protein of SEQ ID NO:2 can be created by introducing one or more nucleotide substitutions, additions or deletions into the nucleotide sequence of SEQ ID NO:1, such that one or more amino acid substitutions, additions or deletions are introduced into the encoded protein.

Mutations can be introduced into SEQ ID NO:1 by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain. Families of amino acid residues having similar side chains have been defined in the art. Certain amino acids have side chains with more than one classifiable characteristic. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, tryptophan, cysteine), nonpolar side chains (e.g. alanine, valine, leucine, isoleucine, proline, phenylalanine, methionine, tyrosine, tryptophan), beta-branched side chains (e.g., threonine, valine, isoleucine) and aromatic side chains (e.g. tyrosine, phenylalanine, tryptophan, histidine). Thus, a predicted nonessential amino acid residue in a growth factor is replaced with another amino acid residue from the same side chain family. Alternatively, in another embodiment, mutations can be introduced randomly along all or part of a growth factor coding sequence, such as by saturation mutagenesis, and the resultant mutants can be screened for growth factor biological activity to identify mutants that retain activity. Following mutagenesis of SEQ ID NOS:1 and 3 the encoded protein can be expressed by any recombinant technology known in the art and the activity of the protein can be determined.

In an important embodiment, a mutant FGF-CX protein can be assayed for (1) the ability to form protein:protein interactions with other FGF-CX proteins, other cell-surface proteins, or biologically active portions thereof, (2) complex formation between a mutant FGF-CX protein and a FGF-CX receptor, (3) the ability of a mutant FGF-CX protein to bind to an intracellular target protein or biologically active portion thereof, (e.g., avidin proteins), or (4) the ability to specifically bind an anti-FGF-CX protein antibody.

Antisense

Another aspect of the invention pertains to isolated antisense nucleic acid molecules that are hybridizable to or complementary to the nucleic acid molecule comprising the nucleotide sequence of SEQ ID NO:1, or fragments, analogs or derivatives thereof. An "antisense" nucleic acid comprises a nucleotide sequence that is complementary to a "sense" nucleic acid encoding a protein, e.g. complementary to the coding strand of a double-stranded cDNA molecule or complementary to an mRNA sequence. In specific aspects, antisense nucleic acid molecules are provided that comprise a sequence complementary to at least about 10, 25, 50, 100, 250 or 500 nucleotides or an entire FGF-CX coding strand, or to only a portion thereof. Nucleic acid molecules encoding fragments, homologs, derivatives and analogs of a FGF-CX protein of SEQ ID NO:2 or antisense nucleic acids complementary to a FGF-CX nucleic acid sequence of SEQ ID NO:1 are additionally provided.

In one embodiment, an antisense nucleic acid molecule is antisense to a "coding region" of the coding strand of a nucleotide sequence encoding FGF-CX. The term "coding region" refers to the region of the nucleotide sequence comprising codons which are translated into amino acid residues (e.g., the protein coding region of human FGF-CX corresponds to SEQ ID NO:2). In another embodiment, the antisense nucleic acid molecule is antisense to a "noncoding region" of the coding strand of a nucleotide sequence encoding FGF-CX. The term "noncoding region" refers to 5' and 3' sequences which flank the coding region that are not translated into amino acids (i.e., also referred to as 5' and 3' untranslated regions).

Given the coding strand sequences encoding FGF-CX disclosed herein (e.g., SEQ ID NO:1), antisense nucleic acids of the invention can be designed according to the rules of Watson and Crick or Hoogsteen base pairing. The antisense nucleic acid molecule can be complementary to the entire coding region of FGF-CX mRNA, but more preferably is an oligonucleotide that is antisense to only a portion of the coding or noncoding region of FGF-CX mRNA. For example, the antisense oligonucleotide can be complementary to the region surrounding the translation start site of FGF-CX mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g. an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g. phosphorothioate derivatives and acridine substituted nucleotides can be used.

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a FGF-CX protein to thereby inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids Res 15: 6625–6641). The antisense nucleic acid molecule can also comprise a 2'-o-methylribonucleotide (Inoue et al. (1987) Nucleic Acids Res 15: 6131–6148) or a chimeric RNA-DNA analogue (Inoue et al. (1987) FEBS Lett 215: 327–330).

Ribozymes and PNA Moieties

Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject.

In still another embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach (1988) Nature 334:585–591)) can be used to catalytically cleave FGF-CX mRNA transcripts to thereby inhibit translation of FGF-CX mRNA. A ribozyme having specificity for a FGF-CX-encoding nucleic acid can be designed based upon the nucleotide sequence of a FGF-CX DNA disclosed herein (i.e., SEQ ID NO:1). For example, a derivative of a Tetrahymena L-19 IVS RNA can be constructed in which the nucleotide sequence of the active site is complementary to the nucleotide sequence to be cleaved in a FGF-CX-encoding mRNA. See, e.g., Cech et al. U.S. Pat. No. 4,987,071, and Cech et al. U.S. Pat. No. 5,116,742. Alternatively, FGF-CX mRNA can be used to select a catalytic RNA having a specific ribonuclease activity from a pool of RNA molecules. See, e.g., Bartel et al., (1993) Science 261:1411–1418.

Alternatively, FGF-CX gene expression can be inhibited by targeting nucleotide sequences complementary to the regulatory region of the FGF-CX (e.g. the FGF-CX promoter and/or enhancers) to form triple helical structures that prevent transcription of the FGF-CX gene in target cells. See generally, Helene. (1991) Anticancer Drug Des. 6: 569–84: Helene, et al. (1992) Ann. N.Y. Acad. Sci. 660:27–36; and Maher (1992) Bioassays 14: 807–15.

In various embodiments, the nucleic acids of FGF-CX can be modified at the base moiety, sugar moiety or phosphate backbone to improve, e.g., the stability, hybridizations or solubility of the molecule. For example, the deoxyribose phosphate backbone of the nucleic acids can be modified to generate peptide nucleic acids (see Hyrup et al. (1996) Bioorg Med Chem 4: 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) above; Perry-O'Keefe et al. (1996) PNAS 93: 14670–675.

PNAs of FGF-CX can be used in therapeutic and diagnostic applications. For example, PNAs can be used as antisense or antigene agents for sequence-specific modulation of gene expression by, e.g. inducing transcription or translation arrest or inhibiting replication. PNAs of FGF-CX can also be used, e.g., in the analysis of single base pair mutations in a gene by, e.g., PNA directed PCR clamping; as artificial restriction enzymes when used in combination with other enzymes. e.g., S1 nucleases (Hyrup B. (1996) above); or as probes or primers for DNA sequence and hybridization (Hyrup et al. (1996) above; Perry-O'Keefe (1996), above).

In another embodiment, PNAs of FGF-CX can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of FGF-CX can be generated that may combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) above). The synthesis of PNA-DNA chimeras can be performed as described in Hyrup (1996) above and Finn et al. (1996) Nucl Acids Res 24: 3357–63. For example, a DNA chain can be synthesized on a solid support using standard phosphoramidite coupling chemistry, and modified nucleoside analogs. e.g. 5'-(4-methoxytrityl)amino-5'-deoxy-thymidine phosphoramidite, can be used between the PNA and the 5' end of DNA (Mag et al. (1989) Nucl Acid Res 17: 5973–88). PNA monomers are then coupled in a stepwise manner to produce a chimeric molecule with a 5' PNA segment and a 3' DNA segment (Finn et al. (1996) above). Alternatively, chimeric molecules can be synthesized with a 5' DNA segment and a 3' PNA segment. See, Petersen et al. (1975) Bioorg Med Chem Lett 5: 1119–11124.

In other embodiments, the oligonucleotide may include other appended groups such as peptides (e.g. for targeting host cell receptors in vivo), or agents facilitating transport across the cell membrane (see, e.g., Letsinger et al., 1989, Proc. Natl. Acad. Sci. U.S.A. 86:6553–6556; Lemaitre et al. 1987, Proc. Natl. Acad. Sci. 84:648–652: PCT Publication No. WO88/09810) or the blood-brain barrier (see, e.g. PCT Publication No. WO89/10134). In addition, oligonucleotides can be modified with hybridization triggered cleavage agents (See, e.g., Krol et al., 1988, BioTechniques 6:958–976) or intercalating agents. (See, e.g., Zon. 1988, Pharm. Res. 5: 539–549). To this end, the oligonucleotide may be conjugated to another molecule, e.g. a peptide, a hybridization triggered cross-linking agent, a transport agent, a hybridization-triggered cleavage agent, etc.

FGF-CX Polypeptides

The novel protein of the invention includes the FGF-CX-like protein whose sequence is provided in FIG. 1 (SEQ ID NO:2). The invention also includes a mutant or variant protein any of whose residues may be changed from the corresponding residue shown in FIG. 1 while still encoding a protein that maintains its FGF-CX-like activities and physiological functions, or a functional fragment thereof. In the mutant or variant protein, up to 20% or more of the residues may be so changed.

In general, an FGF-CX-like variant that preserves FGF-CX-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above. Furthermore, without limiting the scope of the invention, the following positions in Table 2 (using the numbering provided in SEQ ID NO:2) may be substituted as indicated, such that a mutant or variant protein may include one or more than one of the substitutions indicated. The suggested substitutions do not limit the range of possible substitutions that may be made at a given position.

TABLE 2

| Position | Possible Substitution |
|---|---|
| 6: | Glu to Asp |
| 9: | Gly to Ser, Thr, or Asn |
| 10: | Phe to Tyr |
| 11: | Leu to Phe or Ile |
| 15: | Glu to Asp |
| 16: | Gly to Ala |
| 17: | Leu to Ile or Val |
| 19: | Gln may be deleted |
| 21: | Val to Phe or Ile |
| 31: | Gly to Lys, Arg, Ser, or Ala |
| 33: | Arg to Lys or Ser |
| 35: | Pro to Leu or Val |
| 38: | Gly to Asn or Ser |
| 39: | Glu to Asp |
| 40: | Arg to Lys, His, or Pro |
| 42: | Ser to Thr, Ala, or Gly |
| 43: | Ala to Gln, Asn, or Ser |
| 48: | Ala to Ser or Gly |
| 51: | Gly to Ala |
| 53: | Gly to Ala or deleted |
| 54: | Ala to Gly, Val, or deleted |
| 55: | Ala to Ser or Thr |
| 56: | Gln to Asp, Glu, or Asn |
| 58: | Ala to Ser, Thr, Asn, Gln, Asp, or Glu |
| 61: | His to Gln, Asn, Lys, or Arg |
| 78: | Gln to Asn, Glu, or Asp |
| 80: | Leu to Phe or Ile |
| 82: | Asp to Glu, Asn, or Gln |
| 84: | Ser to Asn, Thr, or Gln |
| 85: | Val to Ile |
| 90: | Gln to Asn or Lys |
| 103: | Val to Ile |
| 115: | Ser to Thr |
| 123: | Asp to Glu |
| 128: | Tyr to Phe |
| 135: | Ser to Thr, Gln, or Asn |
| 138: | Ile to Val or Leu |
| 155: | Ile to Leu |
| 159: | Gly to Val or Ala |
| 161: | Thr to Ser |
| 166: | Phe to Tyr |
| 177: | Asp to Glu |
| 181: | Ser to Ala or Thr |

TABLE 2-continued

| Position | Possible Substitution |
|---|---|
| 198: | Glu to Asp |
| 199: | Arg to Lys |
| 207: | Leu to Ile or Val |
| 209: | Met to any residue |
| 211: | Thr to Ser |

One aspect of the invention pertains to isolated FGF-CX proteins, and biologically active portions thereof, or derivatives, fragments, analogs or homologs thereof. Also provided are polypeptide fragments suitable for use as immunogens to raise anti-FGF-CX antibodies. In one embodiment, native FGF-CX proteins can be isolated from cells or tissue sources by an appropriate purification scheme using standard protein purification techniques. In another embodiment, FGF-CX proteins are produced by recombinant DNA techniques. Alternative to recombinant expression, a FGF-CX protein or polypeptide can be synthesized chemically using standard peptide synthesis techniques.

An "isolated" or "purified" protein or biologically active portion thereof is substantially free of cellular material or other contaminating proteins from the cell or tissue source from which the FGF-CX protein is derived, or substantially free from chemical precursors or other chemicals when chemically synthesized. The language "substantially free of cellular material" includes preparations of FGF-CX protein in which the protein is separated from cellular components of the cells from which it is isolated or recombinantly produced. In one embodiment, the language "substantially free of cellular material" includes preparations of FGF-CX protein having less than about 30% (by dry weight) of non-FGF-CX protein (also referred to herein as a "contaminating protein"), more preferably less than about 20% of non-FGF-CX protein, still more preferably less than about 10% of non-FGF-CX protein, and most preferably less than about 5% non-FGF-CX protein. When the FGF-CX protein or biologically active portion thereof is recombinantly produced, it is also preferably substantially free of culture medium, i.e., culture medium represents less than about 20%, more preferably less than about 1%, and most preferably less than about 5% of the volume of the protein preparation.

The language "substantially free of chemical precursors or other chemicals" includes preparations of FGF-CX protein in which the protein is separated from chemical precursors or other chemicals that are involved in the synthesis of the protein. In one embodiment, the language "substantially free of chemical precursors or other chemicals" includes preparations of FGF-CX protein having less than about 30% (by dry weight) of chemical precursors or non-FGF-CX chemicals, more preferably less than about 20% chemical precursors or non-FGF-CX chemicals, still more preferably less than about 10% chemical precursors or non-FGF-CX chemicals, and most preferably less than about 5% chemical precursors or non-FGF-CX chemicals.

Biologically active portions of a FGF-CX protein include peptides comprising amino acid sequences sufficiently homologous to or derived from the amino acid sequence of the FGF-CX protein, e.g., the amino acid sequence shown in SEQ ID NO:2 that include fewer amino acids than the full length FGF-CX proteins, and exhibit at least one activity of a FGF-CX protein. Typically, biologically active portions comprise a domain or motif with at least one activity of the FGF-CX protein. A biologically active portion of a FGF-CX protein can be a polypeptide which is, for example, 10, 25, 50, 100 or more amino acids in length.

A biologically active portion of a FGF-CX protein of the present invention may contain at least one of the above-identified domains substantially conserved between the FGF family of proteins. Moreover, other biologically active portions, in which other regions of the protein are deleted, can be prepared by recombinant techniques and evaluated for one or more of the functional activities of a native FGF-CX protein.

In an embodiment, the FGF-CX protein has an amino acid sequence shown in SEQ ID NO:2 In other embodiments, the FGF-CX protein is substantially homologous to SEQ ID NO:2 and retains the functional activity of the protein of SEQ ID NO:2, yet differs in amino acid sequence due to natural allelic variation or mutagenesis, as described in detail below. Accordingly, in another embodiment, the FGF-CX protein is a protein that comprises an amino acid sequence at least about 45% homologous to the amino acid sequence of SEQ ID NO:2 and retains the functional activity of the FGF-CX proteins of SEQ ID NO:2. In another embodiment, the FGF-CX is a protein that contains an amino acid sequence at least about 45% homologous, and more preferably about 55, 65, 70, 75, 80, 85, 90, 95, 98 or even 99% homologous to the amino acid sequence of SEQ ID NO:2 and retains the functional activity of the FGF-CX proteins of the corresponding polypeptide having the sequence of SEQ ID NO:2.

Determining Homology Between Two or More Sequences

To determine the percent homology of two amino acid sequences or of two nucleic acids, the sequences are aligned for optimal comparison purposes (e.g. gaps can be introduced in either of the sequences being compared for optimal alignment between the sequences). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See, Needleman and Wunsch 1970 *J Mol Biol* 48: 443–453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA sequence shown in SEQ ID NO: 1.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region. The term "percentage of positive residues" is calculated by comparing two optimally aligned sequences over that region of comparison, determining the number of positions at which the identical and conservative amino acid substitutions, as defined above, occur in both sequences to yield the number of matched positions, dividing the number of matched positions by the total number of positions in the region of comparison (i.e., the window size), and multiplying the result by 100 to yield the percentage of positive residues.

Chimeric and Fusion Proteins

The invention also provides FGF-CX chimeric or fusion proteins. As used herein, a FGF-CX "chimeric protein" or "fusion protein" comprises a FGF-CX polypeptide operatively linked to a non-FGF-CX polypeptide. A "FGF-CX polypeptide" refers to a polypeptide having an amino acid sequence corresponding to FGF-CX, whereas a "non-FGF-CX polypeptide" refers to a polypeptide having an amino acid sequence corresponding to a protein that is not substantially homologous to the FGF-CX protein, e.g., a protein that is different from the FGF-CX protein and that is derived from the same or a different organism. Within a FGF-CX fusion protein the FGF-CX polypeptide can correspond to all or a portion of a FGF-CX protein. In one embodiment, a FGF-CX fusion protein comprises at least one biologically active portion of a FGF-CX protein. In another embodiment, a FGF-CX fusion protein comprises at least two biologically active portions of a FGF-CX protein. Within the fusion protein, the term "operatively linked" is intended to indicate that the FGF-CX polypeptide and the non-FGF-CX polypeptide are fused in-frame to each other. The non-FGF-CX polypeptide can be fused to the N-terminus or C-terminus of the FGF-CX polypeptide.

For example, in one embodiment a FGF-CX fusion protein comprises a FGF-CX polypeptide operably linked to the extracellular domain of a second protein. Such fusion proteins can be further utilized in screening assays for compounds that modulate FGF-CX activity (such assays are described in detail below).

In another embodiment, the fusion protein is a GST-FGF-CX fusion protein in which the FGF-CX sequences are fused to the C-terminus of the GST (i.e., glutathione S-transferase) sequences. Such fusion proteins can facilitate the purification of recombinant FGF-CX.

In yet another embodiment, the fusion protein is a FGF-CX protein containing a heterologous signal sequence at its N-terminus. For example, the native FGF-CX signal sequence (i.e. amino acids 1 to 20 of SEQ ID NO:2) can be removed and replaced with a signal sequence from another protein. In certain host cells (e.g., mammalian host cells), expression and/or secretion of FGF-CX can be increased through use of a heterologous signal sequence.

In another embodiment, the fusion protein is a FGF-CX-immunoglobulin fusion protein in which the FGF-CX sequences comprising one or more domains are fused to sequences derived from a member of the immunoglobulin protein family. The FGF-CX-immunoglobulin fusion proteins of the invention can be incorporated into pharmaceutical compositions and administered to a subject to inhibit an interaction between a FGF-CX ligand and a FGF-CX protein on the surface of a cell, to thereby suppress FGF-CX-mediated signal transduction in vivo. In one nonlimiting example, a contemplated FGF-CX ligand of the invention is the FGF-CX receptor. The FGF-CX-immunoglobulin fusion proteins can be used to affect the bioavailability of a FGF-CX cognate ligand. Inhibition of the FGF-CX ligand/FGF-CX interaction may be useful therapeutically for both the treatment of proliferative and differentiative disorders, as well as modulating (e.g., promoting or inhibiting) cell survival. Moreover, the FGF-CX-immunoglobulin fusion proteins of the invention can be used as immunogens to produce anti-FGF-CX antibodies in a subject, to purify FGF-CX ligands, and in screening assays to identify molecules that inhibit the interaction of FGF-CX with a FGF-CX ligand.

A FGF-CX chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively. PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). A FGF-CX-encoding nucleic acid can be cloned into such an expression vector such that the fusion moiety is linked in-frame to the FGF-CX protein.

FGF-CX Agonists and Antagonists

The present invention also pertains to variants of the FGF-CX proteins that function as either FGF-CX agonists (mimetics) or as FGF-CX antagonists. Variants of the FGF-CX protein can be generated by mutagenesis, e.g., discrete point mutation or truncation of the FGF-CX protein. An agonist of the FGF-CX protein can retain substantially the same, or a subset of, the biological activities of the naturally occurring form of the FGF-CX protein. An antagonist of the FGF-CX protein can inhibit one or more of the activities of the naturally occurring form of the FGF-CX protein by, for example, competitively binding to a downstream or upstream member of a cellular signaling cascade which includes the FGF-CX protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the FGF-CX proteins.

Variants of the FGF-CX protein that function as either FGF-CX agonists (mimetics) or as FGF-CX antagonists can be identified by screening combinatorial libraries of mutants, e.g., truncation mutants, of the FGF-CX protein for FGF-CX protein agonist or antagonist activity. In one embodiment, a variegated library of FGF-CX variants is generated by combinatorial mutagenesis at the nucleic acid level and is encoded by a variegated gene library. A variegated library of FGF-CX variants can be produced by, for example, enzymatically ligating a mixture of synthetic oligonucleotides into gene sequences such that a degenerate set of potential FGF-CX sequences is expressible as individual polypeptides, or alternatively, as a set of larger fusion proteins (e.g., for phage display) containing the set of FGF-CX sequences therein. There are a variety of methods which can be used to produce libraries of potential FGF-CX variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential FGF-CX sequences. Methods for synthesizing degenerate oligonucleotides are known in the art (see, e.g., Narang (1983) *Tetrahedron* 39:3; Itakura et al. (1984) *Annu Rev Biochem* 53:323; Itakura et al. (1984) *Science* 198:1056; Ike et al. (1983) *Nucl Acid Res* 11:477.

Polypeptide Libraries

In addition, libraries of fragments of the FGF-CX protein coding sequence can be used to generate a variegated population of FGF-CX fragments for screening and subsequent selection of variants of a FGF-CX protein. In one embodiment, a library of coding sequence fragments can be generated by treating a double stranded PCR fragment of a FGF-CX coding sequence with a nuclease under conditions wherein nicking occurs only about once per molecule, denaturing the double stranded DNA, renaturing the DNA to form double stranded DNA that can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the FGF-CX protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of FGF-CX proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique that enhances the frequency of functional mutants in the libraries, can be used in combination with the screening assays to identify FGF-CX variants (Arkin and Yourvan (1992) PNAS 89:7811–7815; Delgrave et al. (1993) Protein Engineering 6:327–331).

Anti-FGF-CX Antibodies

The term “antibody” as used herein refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, Fab, Fab' and F(ab')2 fragments, and an Fab expression library. In general, antibody molecules obtained from humans relates to any of the classes IgG, IgM, IgA, IgE and IgD, which differ from one another by the nature of the heavy chain present in the molecule. Certain classes have subclasses as well, such as IgG1, IgG2, and others. Furthermore, in humans, the light chain may be a kappa chain or a lambda chain. Reference herein to antibodies includes a reference to all such classes, subclasses and types of human antibody species.

An isolated protein of the invention intended to serve as an antigen, or a portion or fragment thereof, can be used as an immunogen to generate antibodies that immunospecifically bind the antigen, using standard techniques for polyclonal and monoclonal antibody preparation. The full-length protein can be used or, alternatively, the invention provides antigenic peptide fragments of the antigen for use as immunogens. An antigenic peptide fragment comprises at least 6 amino acid residues of the amino acid sequence of the full length protein, such as an amino acid sequence shown in SEQ ID NO:2, and encompasses an epitope thereof such that an antibody raised against the peptide forms a specific immune complex with the full length protein or with any fragment that contains the epitope. Preferably, the antigenic peptide comprises at least 10 amino acid residues, or at least 15 amino acid residues, or at least 20 amino acid residues, or at least 30 amino acid residues. Preferred epitopes encompassed by the antigenic peptide are regions of the protein that are located on its surface, commonly these are hydrophilic regions.

In certain embodiments of the invention, at least one epitope encompassed by the antigenic peptide is a region of the FGF-CX that is located on the surface of the protein, e.g., a hydrophilic region. A hydrophobicity analysis of the human FGF-CX protein sequence will indicate which regions of a FGF-CX polypeptide are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, Proc. Nat. Acad. Sci. USA 78: 3824–3828; Kyte and Doolittle 1982, J. Mol. Biol. 157: 105–142, each incorporated herein by reference in their entirety. Antibodies that are specific for one or more domains within an antigenic protein, or derivatives, fragments, analogs or homologs thereof, are also provided herein.

A protein of the invention, or a derivative, fragment, analog, homolog or ortholog thereof, may be utilized as an immunogen in the generation of antibodies that immunospecifically bind these protein components.

Various procedures known within the art may be used for the production of polyclonal or monoclonal antibodies directed against a protein of the invention, or against derivatives, fragments, analogs homologs or orthologs thereof (see, for example, Antibodies: A Laboratory Manual, Harlow E. and Lane D, 1988. Cold Spring Harbor Laboratory Press. Cold Spring Harbor, N.Y. incorporated herein by reference). Some of these antibodies are discussed below.

1. Polyclonal Antibodies

For the production of polyclonal antibodies, various suitable host animals (e.g. rabbit, goat, mouse or other mammal) may be immunized by one or more injections with the FGF-CX native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the FGF-CX protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), adjuvants usable in humans such as Bacille Calmette-Guerin and *Corynebacterium parvum*, or similar immunostimulatory agents. Additional examples of adjuvants which can be employed include MPL-TDM adjuvant (monophosphoryl Lipid A, synthetic trehalose dicorynomycolate).

The polyclonal antibody molecules directed against the immunogenic FGF-CX protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa. Vol. 14, No. 8 (Apr. 17, 2000), pp. 25–28).

2. Monoclonal Antibodies

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen binding site capable of immunoreacting with a particular epitope of the antigen characterized by a unique binding affinity for it.

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the FGF-CX protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, Monoclonal Antibodies: Principles and Practice, Academic Press. (1986) pp. 59–103]. Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor: J. Immunol. 133:3001 (1984); Brodeur et al.: Monoclonal Antibody Production Techniques and Applications. Marcel Dekker, Inc., New York, (1987) pp. 51–63).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem. 107:220 (1980). It is an objective, especially important in therapeutic applications of monoclonal antibodies, to identify antibodies having a high degree of specificity and a high binding affinity for the target antigen.

After the desired hybridoma cells are identified, the clones can be subcloned by limiting dilution procedures and grown by standard methods (Goding, 1986). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells. Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, Nature 368, 812–13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

3. Humanized Antibodies

The antibodies directed against the FGF-CX protein antigens of the invention can further comprise humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')2 or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., Nature, 321:522–525 (1986), Riechmann et al., Nature, 332:323–327 (1988); Verhoeyen et al., Science, 239:1534–1536 (1988)), by substituting rodent CDRs or CDR sequences for the corresponding sequences of a human antibody. (See also U.S. Pat. No. 5,225,539.) In some instances, Fv framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fe), typically that of a human immunoglobulin (Jones et al., 1986; Riechmann et al., 1988; and Presta, Curr. Op. Struct. Biol., 2:593–596 (1992)).

4. Human Antibodies

Fully human antibodies essentially relate to antibody molecules in which the entire sequence of both the light chain and the heavy chain, including the CDRs, arise from human genes. Such antibodies are termed "human antibodies", or "fully human antibodies" herein. Human monoclonal antibodies directed against a FGF-CX protein can be prepared by the trioma technique; the human B-cell hybridoma technique (see Kozbor, et al. 1983 Immunol Today 4: 72) and the EBV hybridoma technique to produce human monoclonal antibodies (see Cole, et al. 1985 In: Monoclonal Antibodies and Cancer Therapy, Alan R. Liss. Inc., pp. 77–96). Human monoclonal antibodies may be utilized in the practice of the present invention and may be produced by using human hybridomas (see Cote, et al., 1983. Proc Natl Acad Sci USA 80: 2026–2030) or by transforming human B-cells with Epstein Barr Virus in vitro (see Cole, et al., 1985 In: Monoclonal Antibodies and Cancer Therapy, Alan R. Liss, Inc., pp. 77–96).

In addition, human antibodies can also be produced using additional techniques, including phage display libraries (Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545, 806; 5,569,825; 5,625,126; 5,633,425; 5,661,016, and in Marks et al. (Bio/Technology 10, 779–783 (1992)); Lonberg et al. (Nature 368 856–859 (1994)); Morrison (Nature 368, 812–13 (1994)); Fishwild et al, (Nature Biotechnology 14, 845–51 (1996)); Neuberger (Nature Biotechnology 14, 826 (1996)); and Lonberg and Huszar (intern. Rev. Immunol. 13 65–93 (1995)).

Human antibodies that specifically bind a FGF-CX protein may additionally be produced using transgenic nonhuman animals which are modified so as to produce fully human antibodies rather than the animal's endogenous antibodies in response to challenge by an antigen. (See publication WO 94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with a FGF-CX immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

5. Fab Fragments and Single Chain Antibodies

According to the invention, techniques can be adapted for the production of single-chain antibodies specific to an antigenic FGF-CX protein of the invention (see e.g., U.S. Pat. No. 4,946,778). In addition, methods can be adapted for the construction of Fab expression libraries (see e.g., Huse, et al., 1989 Science 246: 1275–1281) to allow rapid and effective identification of monoclonal Fab fragments with the desired specificity for a protein or derivatives, fragments, analogs or homologs thereof. Antibody fragments that contain the idiotypes to a protein antigen may be produced by techniques known in the art including, but not limited to: (i) an F(ab')2 fragment produced by pepsin digestion of an antibody molecule; (ii) an Fab fragment generated by reducing the disulfide bridges of an F(ab')2 fragment; (iii) an Fab fragment generated by the treatment of the antibody molecule with papain and a reducing agent and (iv) Fv fragments.

6. Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello. Nature, 305:537–539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')2 bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from E. coli and chemically coupled to form bispecific antibodies. Shalaby et al., J. Exp. Med. 175:217–225 (1992) describe the production of a fully humanized bispecific antibody F(ab')2 molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al. J. Immunol. 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al. Proc. Natl. Acad. Sci. USA 90:6444–6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (Fc R), such as Fc RI (CD64), Fc RII (CD32) and Fc RIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

7. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

8. Effector Function Engineering

It can be desirable to modify the FGF-CX antibody of the invention with respect to effector function, so as to enhance, e.g., the effectiveness of the antibody in treating cancer. For example, cysteine residue(s) can be introduced into the Fe region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al., J. Exp Med., 176: 1191–1195 (1992) and Shopes, J. Immunol., 148: 2918–2922 (1992). Homodimeric antibodies with enhanced anti-tumor activity can also be prepared using heterobifunctional cross-linkers as described in Wolff et al. Cancer Research, 53: 2560–2565 (1993). Alternatively, an antibody can be engineered that has dual Fe regions and can thereby have enhanced complement lysis and ADCC capabilities. See Stevenson et al. Anti-Cancer Drug Design, 3: 219–230 (1989).

9. Immunoconjugates

The invention also pertains to immunoconjugates comprising a FGF-CX antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins. Phytolaca americana proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include 212Bi, 131I, 131In, 90Y, and 186Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaredehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody can be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is in turn conjugated to a cytotoxic agent.

10. Immunoliposomes

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl. Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286–288 (1982) via a disulfide-interchange reaction. A chemotherapeutic agent (such as Doxorubicin) is optionally contained within the liposome. See Gabizon et al., J. National Cancer Inst., 81(19): 1484 (1989).

11. Diagnostic Applications of Antibodies Directed Against the Proteins of the Invention Antibodies directed against a FGF-CX protein of the invention may be used in methods known within the art relating to the localization and/or quantitation of the protein (e.g., for use in measuring levels of the protein within appropriate physiological samples, for use in diagnostic methods, for use in imaging the protein, and the like). In a given embodiment, antibodies against the proteins, or derivatives, fragments, analogs or homologs thereof, that contain the antigen binding domain, are utilized as pharmacologically-active compounds (see below).

An antibody specific for a FGF-CX protein of the invention can be used to isolate the protein by standard techniques, such as immunoaffinity chromatography or immunoprecipitation. Such an antibody can facilitate the purification of the natural protein antigen from cells and of recombinantly produced antigen expressed in host cells. Moreover, such an antibody can be used to detect the antigenic protein (e.g., in a cellular lysate or cell supernatant) in order to evaluate the abundance and pattern of expression of the antigenic protein. Antibodies directed against the FGF-CX protein can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -g a lactosidase, or acetylcholinesterase; examples of suitable prosthetic group complexes include streptavidin/biotin and avidin/biotin: examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I. $^{35}$S or $^{3}$H.

12. Antibody Therapeutics

FGF-CX antibodies of the invention, including polyclonal, monoclonal, humanized and fully human antibodies, may used as therapeutic agents. Such agents will generally be employed to treat or prevent a disease or pathology in a subject. An antibody preparation, preferably one having high specificity and high affinity for its target antigen, is administered to the subject and will generally have an effect due to its binding with the target. Such an effect may be one of two kinds, depending on the specific nature of the interaction between the given antibody molecule and the target antigen in question. In the first instance, administration of the antibody may abrogate or inhibit the binding of the target with an endogenous ligand to which it naturally binds. In this case, the antibody binds to the target and masks a binding site of the naturally occurring ligand, wherein the ligand serves as an effector molecule. Thus the receptor mediates a signal transduction pathway for which ligand is responsible.

Alternatively, the effect may be one in which the antibody elicits a physiological result by virtue of binding to an effector binding site on the target molecule. In this case the target, a receptor having an endogenous ligand which may be absent or defective in the disease or pathology, binds the antibody as a surrogate effector ligand, initiating a receptor-based signal transduction event by the receptor.

A therapeutically effective amount of an antibody of the invention relates generally to the amount needed to achieve a therapeutic objective. As noted above, this may be a binding interaction between the antibody and its target antigen that, in certain cases, interferes with the functioning of the target, and in other cases, promotes a physiological response. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

13. Pharmaceutical Compositions of Antibodies

Antibodies specifically binding a FGF-CX protein of the invention, as well as other molecules identified by the screening assays disclosed herein, can be administered for the treatment of various disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro. et al., editors) Mack Pub. Co., Easton, Pa.: 1995; Drug Absorption Enhancement: Concepts, Possibilities, Limitations, And Trends, Harwood Academic Publishers, Langhorne. Pa., 1994, and Peptide And Protein Drug Delivery (Advances In Parenteral Sciences, Vol. 4), 1991, M. Dekker, New York.

If the antigenic protein is intracellular and whole antibodies are used as inhibitors, internalizing antibodies are preferred. However, liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. Sec, e.g., Marasco et al., Proc. Natl. Acad. Sci. USA, 90: 7889–7893 (1993). The formulation herein can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

FGF-CX Recombinant Expression Vectors and Host Cells

Another aspect of the invention pertains to vectors, preferably expression vectors, containing a nucleic acid encoding FGF-CX protein, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; GENE EXPRESSION TECHNOLOGY: METHODS IN ENZYMOLOGY 185. Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., FGF-CX proteins, mutant forms of FGF-CX, fusion proteins, etc.).

The recombinant expression vectors of the invention can be designed for expression of FGF-CX in prokaryotic or eukaryotic cells. For example, FGF-CX can be expressed in bacterial cells such as E. coli, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31–40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion E. coli expression vectors include pTrc (Amrann et al. (1988) Gene 69:301–315) and pET 11d (Studier et al. GENE EXPRESSION TECHNOLOGY: METHODS IN ENZYNIOLOGY 185, Academic Press. San Diego, Calif. (1990) 60–89).

One strategy to maximize recombinant protein expression in E. coli is to express the protein in a host bacteria with an impaired capacity to proteolytically cleave the recombinant protein. See, Gottesman, GENE EXPRESSION TECHNOLOGY: METHODS IN ENZYMOLOGY 185, Academic Press. San Diego. Calif. (1990) 119–128. Another strategy is to alter the nucleic acid sequence of the nucleic acid to be inserted into an expression vector so that the individual codons for each amino acid are those preferentially utilized in E. coli (Wada et al., (1992) Nucleic Acids Res. 20:2111–2118). Such alteration of nucleic acid sequences of the invention can be carried out by standard DNA synthesis techniques.

In another embodiment, the FGF-CX expression vector is a yeast expression vector. Examples of vectors for expression in yeast S. cerivisae include pYepSec1 (Baldari, et al., (1987) EMBO J 6:229–234), pMFa (Kurjan and Herskowitz, (1982) Cell 30:933–943), pJRY88 (Schultz et al. (1987) Gene 54:113–123). pYES2 (Invitrogen Corporation, San Diego. Calif.), and picZ (InVitrogen Corp, San Diego, Calif.).

Alternatively, FGF-CX can be expressed in insect cells using baculovirus expression vectors. Baculovirus vectors available for expression of proteins in cultured insect cells (e.g., SF9 cells) include the pAc series (Smith et al. (1983) Mol Cell Biol 3:2156–2165) and the pVL series (Lucklow and Summers (1989) Virology 170:31–39).

In yet another embodiment, a nucleic acid of the invention is expressed in mammalian cells using a mammalian expression vector. Examples of mammalian expression vectors include pCDM8 (Seed (1987) Nature 329:840) and pMT2PC (Kaufman et al. (1987) EMBO J 6: 187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells. See, e.g., Chapters 16 and 17 of Sambrook et al. MOLECULAR CLONING: A LABORATORY MANUAL. 2nd ed., Cold Spring Harbor Laboratory, Cold Spring Harbor Laboratory Press, Cold Spring Harbor. N.Y. 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev 1:268–277), lymphoid-specific promoters (Calame and Eaton (1988) Adv Immunol 43:235–275), in particular promoters of T cell receptors (Winoto and Baltimore (1989) EMBO J 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) PNAS 86:5473–5477), pancreas-specific promoters (Edlund et al. (1985) Science 230:912–916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss (1990) Science 249:374–379) and the α-fetoprotein promoter (Campes and Tilghman (1989) Genes Dev 3:537–546).

The invention further provides a recombinant expression vector comprising a DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to FGF-CX mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., "Antisense RNA as a molecular tool for genetic analysis," Reviews—Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example. FGF-CX protein can be expressed in bacterial cells such as E. coli, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding FGF-CX or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) FGF-CX protein. Accordingly, the invention further provides methods for producing FGF-CX protein using the host cells of the invention. In one embodiment, the method comprises culturing the host cell of invention (into which a recombinant expression vector encoding FGF-CX has been introduced) in a suitable medium such that FGF-CX protein is produced. In another embodiment, the method further comprises isolating FGF-CX from the medium or the host cell.

Transgenic Animals

The host cells of the invention can also be used to produce nonhuman transgenic animals. For example, in one embodiment, a host cell of the invention is a fertilized oocyte or an embryonic stem cell into which FGF-CX-coding sequences have been introduced. Such host cells can then be used to create non-human transgenic animals in which exogenous FGF-CX sequences have been introduced into their genome or homologous recombinant animals in which endogenous FGF-CX sequences have been altered. Such animals are useful for studying the function and/or activity of FGF-CX and for identifying and/or evaluating modulators of FGF-CX activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous FGF-CX gene has been altered by homologous recombination between the endogenous gene and an exogenous DNA molecule introduced into a cell of the animal, e.g., an embryonic cell of the animal, prior to development of the animal.

A transgenic animal of the invention can be created by introducing FGF-CX-encoding nucleic acid into the male pronuclei of a fertilized oocyte, e.g., by microinjection, retroviral infection, and allowing the oocyte to develop in a pseudopregnant female foster animal. The human FGF-CX DNA sequence of SEQ ID NO:1 can be introduced as a transgene into the genome of a non-human animal. Alternatively, a nonhuman homologue of the human FGF-CX gene, such as a mouse FGF-CX gene, can be isolated based on hybridization to the human FGF-CX cDNA (described further above) and used as a transgene. Intronic sequences and polyadenylation signals can also be included in the transgene to increase the efficiency of expression of the transgene. A tissue-specific regulatory sequence(s) can be operably linked to the FGF-CX transgene to direct expression of FGF-CX protein to particular cells. Methods for generating transgenic animals via embryo manipulation and microinjection, particularly animals such as mice, have become conventional in the art and are described, for example, in U.S. Pat. Nos. 4,736,866: 4,870,009, and 4,873, 191; and Hogan 1986, In: MANIPULATING THE MOUSE EMBRYO, Cold Spring Harbor Laboratory Press, Cold Spring Harbor, N.Y. Similar methods are used for production of other transgenic animals. A transgenic founder animal can be identified based upon the presence of the FGF-CX transgene in its genome and/or expression of FGF-CX mRNA in tissues or cells of the animals. A transgenic founder animal can then be used to breed additional animals carrying the transgene. Moreover, transgenic animals carrying a transgene encoding FGF-CX can further be bred to other transgenic animals carrying other transgenes.

To create a homologous recombinant animal, a vector is prepared which contains at least a portion of a FGF-CX gene into which a deletion, addition or substitution has been introduced to thereby alter, e.g., functionally disrupt, the FGF-CX gene. The FGF-CX gene can be a human gene (e.g. SEQ ID NO:1), but more preferably, is a non-human homologue of a human FGF-CX gene. For example, a mouse homologue of human FGF-CX gene of SEQ ID NO:1 can be used to construct a homologous recombination vector suitable for altering an endogenous FGF-CX gene in the mouse genome. In one embodiment, the vector is designed such that, upon homologous recombination, the endogenous FGF-CX gene is functionally disrupted (i.e., no longer encodes a functional protein; also referred to as a "knock out" vector).

Alternatively, the vector can be designed such that, upon homologous recombination, the endogenous FGF-CX gene is mutated or otherwise altered but still encodes functional protein (e.g., the upstream regulatory region can be altered to thereby alter the expression of the endogenous FGF-CX protein). In the homologous recombination vector, the altered portion of the FGF-CX gene is flanked at its 5' and 3' ends by additional nucleic acid of the FGF-CX gene to allow for homologous recombination to occur between the exogenous FGF-CX gene carried by the vector and an endogenous FGF-CX gene in an embryonic stem cell. The additional flanking FGF-CX nucleic acid is of sufficient length for successful homologous recombination with the endogenous gene. Typically, several kilobases of flanking DNA (both at the 5' and 3' ends) are included in the vector. See e.g., Thomas et al. (1987) *Cell* 51:503 for a description of homologous recombination vectors. The vector is introduced into an embryonic stem cell line (e.g. by electroporation) and cells in which the introduced FGF-CX gene has homologously recombined with the endogenous FGF-CX gene are selected (see e.g., Li et al. (1992) *Cell* 69:915).

The selected cells are then injected into a blastocyst of an animal (e.g., a mouse) to form aggregation chimeras. See e.g., Bradley 1987, In: TERATOCARCINOMAS AND EMBRYONIC STEM CELLS: A PRACTICAL APPROACH, Robertson, ed. IRL, Oxford, pp. 113–152. A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Curr Opin Biotechnol* 2:823–829; PCT International Publication Nos.: WO 90/11354; WO 91/01140; WO 92/0968; and WO 93/04169.

In another embodiment, transgenic non-humans animals can be produced that contain selected systems that allow for regulated expression of the transgene. One example of such a system is the cre/loxP recombinase system of bacteriophage P1. For a description of the cre/loxP recombinase system, see, e.g. Lakso et al. (1992) *PNAS* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813. In brief, a cell, e.g. a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

Pharmaceutical Compositions

The FGF-CX nucleic acid molecules, FGF-CX proteins, and anti-FGF-CX antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens, antioxidants such as ascorbic acid or sodium bisulfite, chelating agents such as ethylenediaminetetraacetic acid, buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a FGF-CX protein or anti-FGF-CX antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant. e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

The nucleic acid molecules of the invention can be inserted into vectors and used as gene therapy vectors. Gene therapy vectors can be delivered to a subject by any of a number of routes. e.g., as described in U.S. Pat. No. 5,703,055. Delivery can thus also include, e.g., intravenous injection, local administration (see U.S. Pat. No. 5,328,470) or stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

Uses and Methods of the Invention

The nucleic acid molecules, proteins, protein homologues, and antibodies described herein can be used in one or more of the following methods: (a) screening assays; (b) detection assays (e.g., chromosomal mapping, tissue typing, forensic biology), (c) predictive medicine (e.g., diagnostic assays, prognostic assays, monitoring clinical trials, and pharmacogenomics); and (d) methods of treatment (e.g., therapeutic and prophylactic). As described herein, in one embodiment, a FGF-CX protein of the invention has the ability to bind ATP.

The isolated nucleic acid molecules of the invention can be used to express FGF-CX protein (e.g. via a recombinant expression vector in a host cell in gene therapy applications), to detect FGF-CX mRNA (e.g., in a biological sample) or a genetic lesion in a FGF-CX gene, and to modulate FGF-CX activity, as described further below. In addition, the FGF-CX proteins can be used to screen drugs or compounds that modulate the FGF-CX activity or expression as well as to treat disorders characterized by insufficient or excessive production of FGF-CX protein, for example proliferative or differentiative disorders, or production of FGF-CX protein forms that have decreased or aberrant activity compared to FGF-CX wild type protein. In addition, the anti-FGF-CX antibodies of the invention can be used to detect and isolate FGF-CX proteins and modulate FGF-CX activity.

This invention further pertains to novel agents identified by the above described screening assays and uses thereof for treatments as described herein.

Screening Assays

The invention provides a method (also referred to herein as a "screening assay") for identifying modulators, i.e., candidate or test compounds or agents (e.g., peptides, peptidomimetics, small molecules or other drugs) that bind to FGF-CX proteins or have a stimulatory or inhibitory effect on, for example, FGF-CX expression or FGF-CX activity.

In one embodiment, the invention provides assays for screening candidate or test compounds which bind to or modulate the activity of a FGF-CX protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) *Anticancer Drug Des* 12:145).

Examples of methods for the synthesis of molecular libraries can be found in the art, for example in: DeWitt et al. (1993) *Proc Natl Acad Sci U.S.A.* 90:6909; Erb et al. (1994) *Proc Natl Acad Sci U.S.A.* 91:11422; Zuckermann et al. (1994) *J Med Chem* 37:2678; Cho et al. (1993) *Science* 261:1303; Carrell et al. (1994) *Angew Chem Int Ed Engl* 33:2059; Carell et al. (1994) *Angew Chem Int Ed Engl* 33:2061; and Gallop et al. (1994) *J Med Chem* 37:1233.

Libraries of compounds may be presented in solution (e.g., Houghten (1992) *Biotechniques* 13:412–421), or on beads (Lam (1991) *Nature* 354:82–84), on chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390; Devlin (1990) *Science* 249:404–406; Cwirla et al. (1990) *Proc Natl Acad Sci U.S.A.* 87:6378–6382; Felici (1991) *J Mol Biol* 222:301–310; Ladner above.).

In one embodiment, an assay is a cell-based assay in which a cell which expresses a membrane-bound form of FGF-CX protein, or a biologically active portion thereof, on the cell surface is contacted with a test compound and the ability of the test compound to bind to a FGF-CX protein determined. The cell, for example, can of mammalian origin or a yeast cell. Determining the ability of the test compound to bind to the FGF-CX protein can be accomplished, for example, by coupling the test compound with a radioisotope or enzymatic label such that binding of the test compound to the FGF-CX protein or biologically active portion thereof can be determined by detecting the labeled compound in a complex. For example, test compounds can be labeled with $^{125}$I, $^{35}$S, $^{14}$C, or $^{3}$H, either directly or indirectly, and the radioisotope detected by direct counting of radioemission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In one embodiment, the assay comprises contacting a cell which expresses a membrane-bound form of FGF-CX protein, or a biologically active portion thereof, on the cell surface with a known compound which binds FGF-CX to form an assay mixture, contacting the assay mixture with a test compound, and determining the ability of the test compound to interact with a FGF-CX protein, wherein determining the ability of the test compound to interact with a FGF-CX protein comprises determining the ability of the test compound to preferentially bind to FGF-CX or a biologically active portion thereof as compared to the known compound.

In another embodiment, an assay is a cell-based assay comprising contacting a cell expressing a membrane-bound form of FGF-CX protein, or a biologically active portion thereof, on the cell surface with a test compound and determining the ability of the test compound to modulate (e.g., stimulate or inhibit) the activity of the FGF-CX protein or biologically active portion thereof. Determining the ability of the test compound to modulate the activity of FGF-CX or a biologically active portion thereof can be accomplished, for example, by determining the ability of the FGF-CX protein to bind to or interact with a FGF-CX target molecule. As used herein, a "target molecule" is a molecule with which a FGF-CX protein binds or interacts in nature, for example, a molecule on the surface of a cell which expresses a FGF-CX interacting protein, a molecule on the surface of a second cell, a molecule in the extracellular milieu, a molecule associated with the internal surface of a cell membrane or a cytoplasmic molecule. A FGF-CX target molecule can be a non-FGF-CX molecule or a FGF-CX protein or polypeptide of the present invention. In one embodiment, a FGF-CX target molecule is a component of a signal transduction pathway that facilitates transduction of an extracellular signal (e.g. a signal generated by binding of a compound to a membrane-bound FGF-CX molecule) through the cell membrane and into the cell. The target, for example, can be a second intercellular protein that has catalytic activity or a protein that facilitates the association of downstream signaling molecules with FGF-CX.

Determining the ability of the FGF-CX protein to bind to or interact with a FGF-CX target molecule can be accomplished by one of the methods described above for determining direct binding. In one embodiment, determining the ability of the FGF-CX protein to bind to or interact with a FGF-CX target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising a FGF-CX-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the present invention is a cell-free assay comprising contacting a FGF-CX protein or biologically active portion thereof with a test compound and determining the ability of the test compound to bind to the FGF-CX protein or biologically active portion thereof. Binding of the test compound to the FGF-CX protein can be determined either directly or indirectly as described above. In one embodiment, the assay comprises contacting the FGF-CX protein or biologically active portion thereof with a known compound which binds FGF-CX to form an assay mixture, contacting the assay mixture with a test compound, and determining the ability of the test compound to interact with a FGF-CX protein, wherein determining the ability of the test compound to interact with a FGF-CX protein comprises determining the ability of the test compound to preferentially bind to FGF-CX or biologically active portion thereof as compared to the known compound.

In another embodiment, an assay is a cell-free assay comprising contacting FGF-CX protein or biologically active portion thereof with a test compound and determining the ability of the test compound to modulate (e.g., stimulate or inhibit) the activity of the FGF-CX protein or biologically active portion thereof. Determining the ability of the test compound to modulate the activity of FGF-CX can be accomplished, for example, by determining the ability of the FGF-CX protein to bind to a FGF-CX target molecule by one of the methods described above for determining direct binding. In an alternative embodiment, determining the ability of the test compound to modulate the activity of FGF-CX can be accomplished by determining the ability of the FGF-CX protein further modulate a FGF-CX target molecule. For example, the catalytic/enzymatic activity of the target molecule on an appropriate substrate can be determined as previously described.

In yet another embodiment, the cell-free assay comprises contacting the FGF-CX protein or biologically active portion thereof with a known compound which binds FGF-CX to form an assay mixture, contacting the assay mixture with a test compound, and determining the ability of the test compound to interact with a FGF-CX protein, wherein determining the ability of the test compound to interact with a FGF-CX protein comprises determining the ability of the FGF-CX protein to preferentially bind to or modulate the activity of a FGF-CX target molecule.

The cell-free assays of the present invention are amenable to use of both the soluble form or the membrane-bound form of FGF-CX. In the case of cell-free assays comprising the membrane-bound form of FGF-CX, it may be desirable to utilize a solubilizing agent such that the membrane-bound form of FGF-CX is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide. Triton® X-100, Triton® X-114. Thesit®, Isotridecypoly(ethylene glycol ether)$_n$, N-dodecyl—N,N-dimethyl-3-ammonio-1-propane sulfonate, 3-(3-cholamidopropyl) dimethylamminiol- 1-propane sulfonate (CHAPS), or 3-(3-cholamidopropyl)dimethylamminiol-2-hydroxy-1-propane sulfonate (CHAPSO).

In more than one embodiment of the above assay methods of the present invention, it may be desirable to immobilize either FGF-CX or its target molecule to facilitate separation of complexed from uncomplexed forms of one or both of the proteins, as well as to accommodate automation of the assay. Binding of a test compound to FGF-CX, or interaction of FGF-CX with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, GST-FGF-CX fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or FGF-CX protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of FGF-CX binding or activity determined using standard techniques.

Other techniques for immobilizing proteins on matrices can also be used in the screening assays of the invention. For example, either FGF-CX or its target molecule can be immobilized utilizing conjugation of biotin and streptavidin. Biotinylated FGF-CX or target molecules can be prepared from biotin-NHS (N-hydroxy-succinimide) using techniques well known in the art (e.g., biotinylation kit. Pierce Chemicals. Rockford, Ill.), and immobilized in the wells of streptavidin-coated 96 well plates (Pierce Chemical). Alternatively, antibodies reactive with FGF-CX or target molecules, but which do not interfere with binding of the FGF-CX protein to its target molecule, can be derivatized to the wells of the plate, and unbound target or FGF-CX trapped in the wells by antibody conjugation. Methods for detecting such complexes, in addition to those described above for the GST-immobilized complexes, include immunodetection of complexes using antibodies reactive with the FGF-CX or target molecule, as well as enzyme-linked assays that rely on detecting an enzymatic activity associated with the FGF-CX or target molecule.

In another embodiment, modulators of FGF-CX expression are identified in a method wherein a cell is contacted with a candidate compound and the expression of FGF-CX mRNA or protein in the cell is determined. The level of expression of FGF-CX mRNA or protein in the presence of the candidate compound is compared to the level of expression of FGF-CX mRNA or protein in the absence of the candidate compound. The candidate compound can then be identified as a modulator of FGF-CX expression based on this comparison. For example, when expression of FGF-CX mRNA or protein is greater (statistically significantly greater) in the presence of the candidate compound than in its absence, the candidate compound is identified as a stimulator of FGF-CX mRNA or protein expression. Alternatively, when expression of FGF-CX mRNA or protein is less (statistically significantly less) in the presence of the candidate compound than in its absence, the candidate compound is identified as an inhibitor of FGF-CX mRNA or protein expression. The level of FGF-CX mRNA or protein expression in the cells can be determined by methods described herein for detecting FGF-CX mRNA or protein.

In yet another aspect of the invention, the FGF-CX proteins can be used as "bait proteins" in a two-hybrid assay or three hybrid assay (see, e.g., U.S. Pat. No. 5,283,317; Zervos et al. (1993) Cell 72:223–232; Madura et al. (1993) J Biol Chem 268:12046–12054; Bartel et al. (1993) Biotechniques 14:920–924; Iwabuchi et al. (1993) Oncogene 8:1693–1696; and Brent WO94/10300), to identify other proteins that bind to or interact with FGF-CX ("FGF-CX-binding proteins" or "FGF-CX-bp") and modulate FGF-CX activity. Such FGF-CX-binding proteins are also likely to be involved in the propagation of signals by the FGF-CX proteins as, for example, upstream or downstream elements of the FGF-CX pathway.

The two-hybrid system is based on the modular nature of most transcription factors, which consist of separable DNA-binding and activation domains. Briefly, the assay utilizes two different DNA constructs. In one construct, the gene that codes for FGF-CX is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a FGF-CX-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with FGF-CX.

This invention further pertains to novel agents identified by the above-described screening assays and uses thereof for treatments as described herein.

Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample.

The FGF-CX sequences of the present invention can also be used to identify individuals from minute biological samples. In this technique, an individual's genomic DNA is digested with one or more restriction enzymes, and probed on a Southern blot to yield unique bands for identification. The sequences of the present invention are useful as additional DNA markers for RFLP ("restriction fragment length polymorphisms," described in U.S. Pat. No. 5,272,057).

Furthermore, the sequences of the present invention can be used to provide an alternative technique that determines the actual base-by-base DNA sequence of selected portions of an individual's genome. Thus, the FGF-CX sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The FGF-CX sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Much of the allelic variation is due to single nucleotide polymorphisms (SNPs), which include restriction fragment length polymorphisms (RFLPs).

Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, as described above, can comfortably provide positive individual identification with a panel of perhaps 10 to 1,000 primers that each yield a noncoding amplified sequence of 100 bases. If predicted coding sequences are used, a more appropriate number of primers for positive individual identification would be 500–2,000.

Predictive Medicine

The present invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining FGF-CX protein and/or nucleic acid expression as well as FGF-CX activity, in the context of a biological sample (e.g., blood, serum, cells, tissue) to thereby determine whether an individual is afflicted with a disease or disorder, or is at risk of developing a disorder, associated with aberrant FGF-CX expression or activity. The invention also provides for prognostic (or predictive) assays for determining whether an individual is at risk of developing a disorder associated with FGF-CX protein, nucleic acid expression or activity. For example, mutations in a FGF-CX gene can be assayed in a biological sample. Such assays can be used for prognostic or predictive purpose to thereby prophylactically treat an individual prior to the onset of a disorder characterized by or associated with FGF-CX protein, nucleic acid expression or activity.

Another aspect of the invention provides methods for determining FGF-CX protein, nucleic acid expression or FGF-CX activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs, compounds) on the expression or activity of FGF-CX in clinical trials.

These and other agents are described in further detail in the following sections.

Diagnostic Assays

Fibroblast growth factors FGF-1 through FGF-9 generally promote cell proliferation in cells carrying the particular growth factor receptor. Examples of FGF growth promotion include epithelial cells, such as fibroblasts and keratinocytes, in the anterior eye after surgery. Other conditions in which proliferation of cells plays a role include tumors, restenosis, psoriasis, Dupuytren's contracture, diabetic complications, Kaposi's sarcoma and rheumatoid arthritis.

FGF-CX may be used in the method of the invention for detecting its corresponding fibroblast growth factor receptor CX (FGFRCX) in a sample or tissue. The method comprises contacting the sample or tissue with FGF-CX, allowing formation of receptor-ligand pairs, and detecting any FGFRCX: FGF-CX pairs. Compositions containing FGF-CX can be used to increase FGFRCX activity, for example to stimulate cartilage or bone repair. Compositions containing FGF-CX antagonists or FGF-CX binding agents (e.g. anti-FGF-CX antibodies) can be used to treat diseases caused by an excess of FGF-CX or overactivity of FGFRCX, especially multiple or solitary hereditary exostosis, hallux valgus deformity, achondroplasia, synovial chondromatosis and endochondromas.

Glia activating factor (GAF) and the DNA encoding GAF act to specifically promote growth of glial cells. Some examples of glia-associated disorders in which GAF may be utilized to modulate glial cell activities are cerebral lesions, cerebral edema, senile dementia. Alzheimer's disease, diabetic neuropathies, etc. Similarly, FGF-CX may be used in diagnosis or treating glial cell related disorders. The glial-cell modulating activity of FGF-CX may be as a neuroprotective-like activity, and FGF-CX may be used as a neuroprotective agent. Due to the close homology of FGF-CX to FGF-9, which was identified originally as a glia activating factor, it can be presumed that the FGF-CX sequence is also a glia activating factor. FGF-CX can therefor be used to stimulate the growth of glia cells and can be used to accelerate healing of cerebral lesions or to treat cerebral edema, senile dementia. Alzheimer's disease, or diabetic neuropathy.

FGF-CX can also be used to stimulates fibroblasts (for accelerating healing of burns, wounds, ulcers, etc), megakaryocytes (to increase the number of platelets), hematopoictic cells, immune system cells, and vascular smooth muscle cells. FGF-CX is also expected to have osteogenesis-promoting activity, and can be used for treating bone fractures and osteoporosis. Assay of FGF-CX polypeptide or nucleic acid moieties may be useful in diagnosis of cerebral tumors, and antibodies against could be used to treat such tumors. It can also be used as a reagent for stimulating growth of cultured cells. An anticipated dosage is 1 ng–0.1 mg/kg/day, though treatment may vary depending on the type or severity of the disorder being treated. FGF-CX polypeptides may be used as platelet increasing agents, osteogenesis promoting agents or for treating cerebral nervous diseases or hepatopathy such as hepatic cirrhosis. They can also be used to treat cancer when used alongside an anticancer agent. Antibodies directed against the FGF-CX polypeptide, or fragments, derivatives, or analogs thereof, can be used for detecting or determining a biological activity of a FGF-CX polypeptide or for purifying a FGF-CX polypeptide. Those antibodies that also neutralize the cell growth activity of FGF-CX can be used as anticancer agents.

Many, if not all, homologous proteins are known in the art to have closely related or identical functions. See, e.g., Lewin. "Chapter 21: Structural Genes Belong to Families" In: GENES II, 1985. John Wiley and Sons, Inc., New York. The FGF-CX polypeptide closely resembles the *Xenopus* XFGF-CX protein, which was shown previously to be specifically expressed in highly proliferative tissues (see, e.g., Koga et al., above). Therefore, it is presumed that FGF-CX would also modulate cellular activity in highly proliferative tissues. FGF-CX may thus be particularly useful in diagnosing proliferative disorders and in stimulating the growth of cells and tissues in order to overcome pathological states in which such growth has been suppressed or inhibited. Oligonucleotides corresponding to any one portion of the FGF-CX nucleic acids of SEQ ID NO:1 may be used to detect the expression of a FGF-CX-like gene. The proteins of the invention may be used to stimulate production of antibodies specifically binding the proteins. Such antibodies may be used in immunodiagnostic procedures to detect the occurrence of the protein in a sample. The proteins of the invention may be used to stimulate cell growth and cell proliferation in conditions in which such growth would be favorable. An example would be to counteract toxic side effects of chemotherapeutic agents on, for example, hematopoiesis and platelet formation, linings of the gastrointestinal tract, and hair follicles. They may also be used to stimulate new cell growth in neurological disorders including, for example, Alzheimer's disease. Alternatively, antagonistic treatments may be administered in which an antibody specifically binding the FGF-CX-like proteins of the invention would abrogate the specific growth-inducing effects of the proteins. Such antibodies may be useful, for example, in the treatment of proliferative disorders including various tumors and benign hyperplasias.

An exemplary method for detecting the presence or absence of FGF-CX in a biological sample involves obtaining a biological sample from a test subject and contacting the biological sample with a compound or an agent capable of detecting FGF-CX protein or nucleic acid (e.g., mRNA, genomic DNA) that encodes FGF-CX protein such that the presence of FGF-CX is detected in the biological sample. An agent for detecting FGF-CX mRNA or genomic DNA is a labeled nucleic acid probe capable of hybridizing to FGF-CX mRNA or genomic DNA. The nucleic acid probe can be, for example, a full-length FGF-CX nucleic acid, such as the nucleic acid of SEQ ID NO:1, or a portion thereof, such as an oligonucleotide of at least 15, 30, 50, 100, 250 or 500 nucleotides in length and sufficient to specifically hybridize under stringent conditions to FGF-CX mRNA or genomic DNA, as described above. Other suitable probes for use in the diagnostic assays of the invention are described herein.

An agent for detecting FGF-CX protein is an antibody capable of binding to FGF-CX protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect FGF-CX mRNA, protein, or genomic DNA in a biological sample in vitro as well as in vivo. For example, in vitro techniques for detection of FGF-CX mRNA include Northern hybridizations and in situ hybridizations. In vitro techniques for detection of FGF-CX protein include enzyme linked immunosorbent assays (ELISAs), Western blots, immunoprecipitations and immunofluorescence. In vitro techniques for detection of FGF-CX genomic DNA include Southern hybridizations. Furthermore, in vivo techniques for detection of FGF-CX protein include introducing into a subject a labeled anti-FGF-CX antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting FGF-CX protein, mRNA, or genomic DNA, such that the presence of FGF-CX protein, mRNA or genomic DNA is detected in the biological sample, and comparing the presence of FGF-CX protein, mRNA or genomic DNA in the control sample with the presence of FGF-CX protein, mRNA or genomic DNA in the test sample.

The invention also encompasses kits for detecting the presence of FGF-CX in a biological sample. For example, the kit can comprise: a labeled compound or agent capable of detecting FGF-CX protein or mRNA in a biological sample; means for determining the amount of FGF-CX in the sample; and means for comparing the amount of FGF-CX in the sample with a standard. The compound or agent can be packaged in a suitable container. The kit can further comprise instructions for using the kit to detect FGF-CX protein or nucleic acid.

Prognostic Assays

The diagnostic methods described herein can furthermore be utilized to identify subjects having or at risk of developing a disease or disorder associated with aberrant FGF-CX expression or activity. For example, the assays described herein, such as the preceding diagnostic assays or the following assays, can be utilized to identify a subject having or at risk of developing a disorder associated with FGF-CX protein, nucleic acid expression or activity in, e.g., proliferative or differentiative disorders such as hyperplasias, tumors, restenosis, psoriasis, Dupuytren's contracture, diabetic complications, or rheumatoid arthritis, etc.; and glia-associated disorders such as cerebral lesions, diabetic neuropathies, cerebral edema, senile dementia, Alzheimer's disease, etc. Alternatively, the prognostic assays can be utilized to identify a subject having or at risk for developing a disease or disorder. Thus, the present invention provides a method for identifying a disease or disorder associated with aberrant FGF-CX expression or activity in which a test sample is obtained from a subject and FGF-CX protein or nucleic acid (e.g. mRNA, genomic DNA) is detected, wherein the presence of FGF-CX protein or nucleic acid is diagnostic for a subject having or at risk of developing a disease or disorder associated with aberrant FGF-CX expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant FGF-CX expression or activity. For example, such methods can be used to determine whether a subject can be effectively treated with an agent for a disorder, such as a proliferative disorder, differentiative disorder, glia-associated disorders, etc. Thus, the present invention provides methods for determining whether a subject can be effectively treated with an agent for a disorder associated with aberrant FGF-CX expression or activity in which a test sample is obtained and FGF-CX protein or nucleic acid is detected (e.g., wherein the presence of FGF-CX protein or nucleic acid is diagnostic for a subject that can be administered the agent to treat a disorder associated with aberrant FGF-CX expression or activity.)

The methods of the invention can also be used to detect genetic lesions in a FGF-CX gene, thereby determining if a subject with the lesioned gene is at risk for, or suffers from, a proliferative disorder, differentiative disorder, glia-associated disorder, etc. In various embodiments, the methods include detecting, in a sample of cells from the subject, the presence or absence of a genetic lesion characterized by at least one of an alteration affecting the integrity of a gene encoding a FGF-CX-protein, or the mis-expression of the FGF-CX gene. For example, such genetic lesions can be detected by ascertaining the existence of at least one of (1) a deletion of one or more nucleotides from a FGF-CX gene; (2) an addition of one or more nucleotides to a FGF-CX gene; (3) a substitution of one or more nucleotides of a FGF-CX gene, (4) a chromosomal rearrangement of a FGF-CX gene; (5) an alteration in the level of a messenger RNA transcript of a FGF-CX gene, (6) aberrant modification of a FGF-CX gene, such as of the methylation pattern of the genomic DNA, (7) the presence of a non-wild type splicing pattern of a messenger RNA transcript of a FGF-CX gene, (8) a non-wild type level of a FGF-CX-protein, (9) allelic loss of a FGF-CX gene, and (10) inappropriate post-translational modification of a FGF-CX-protein. As described herein, there are a large number of assay techniques known in the art which can be used for detecting lesions in a FGF-CX gene. A preferred biological sample is a peripheral blood leukocyte sample isolated by conventional means from a subject. However, any biological sample containing nucleated cells may be used, including, for example, buccal mucosal cells.

In certain embodiments, detection of the lesion involves the use of a probe/primer in a polymerase chain reaction (PCR) (see, e.g., U.S. Pat. Nos. 4,683,195 and 4.683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the FGF-CX-gene (see Abravaya et al. (1995) *Nucl Acids Res* 23:675–682). This method can include the steps of collecting a sample of cells from a patient, isolating nucleic acid (e.g., genomic, mRNA or both) from the cells of the sample, contacting the nucleic acid sample with one or more primers that specifically hybridize to a FGF-CX gene under conditions such that hybridization and amplification of the FGF-CX gene (it present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al., 1990, *Proc Natl Acad Sci USA* 87:1874–1878), transcriptional amplification system (Kwoh, et al., 1989, *Proc Natl Acad Sci USA* 86:1173–1177), Q-Beta Replicase (Lizardi et al. 1988, *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a FGF-CX gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,493,531) can be used to score for the presence of specific mutations by development or loss of a ribozyme cleavage site.

In other embodiments, genetic mutations in FGF-CX can be identified by hybridizing a sample and control nucleic acids, e.g., DNA or RNA, to high density arrays containing hundreds or thousands of oligonucleotides probes (Cronin et al. (1996) *Human Mutation* 7: 244–255, Kozal et al. (1996) *Nature Medicine* 2: 753–759). For example, genetic mutations in FGF-CX can be identified in two dimensional arrays containing light-generated DNA probes as described in Cronin et al. above. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the FGF-CX gene and detect mutations by comparing the sequence of the sample FGF-CX with the corresponding wild-type (control) sequence. Examples of sequencing reactions include those based on techniques developed by Maxim and Gilbert (1977) *PNAS* 74:560 or Sanger (1977) *PNAS* 74:5463. It is also contemplated that any of a variety of automated sequencing procedures can be utilized when performing the diagnostic assays (Naeve et al., (1995) *Biotechniques* 19:448), including sequencing by mass spectrometry (see, e.g., PCT International Publ. No. WO 94/16101; Cohen et al. (1996) *Adv Chromatogr* 3 6:127–162; and Griffin et al. (1993) *Appl Biochem Biotechnol* 38:147–159).

Other methods for detecting mutations in the FGF-CX gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type FGF-CX sequence with potentially mutant RNA or DNA obtained from a tissue sample. The double-stranded duplexes are treated with an agent that cleaves single-stranded regions of the duplex such as which will exist due to basepair mismatches between the control and sample strands. For instance. RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc Natl Acad Sci USA* 85:4397, Saleeba et al (1992) *Methods Enzymol* 217:286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in FGF-CX cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a FGF-CX sequence, e.g., a wild-type FGF-CX sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in FGF-CX genes. For example, single strand conformation polymorphism (SSCP) may be used to detect differences in electrophoretic mobility between mutant and wild type nucleic acids (Orita et al. (1989) *Proc Natl Acad Sci USA:* 86:2766, see also Cotton (1993) *Mutat Res* 285:125–144, Hayashi (1992) *Genet Anal Tech Appl* 9:73–79). Single-stranded DNA fragments of sample and control FGF-CX nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA, rather than DNA, in which the secondary structure is more sensitive to a change in sequence. In one embodiment, the subject method utilizes heteroduplex analysis to separate double stranded heteroduplex molecules on the basis of changes in electrophoretic mobility. See, e.g., Keen et al. (1991) *Trends Genet* 7:5.

In yet another embodiment the movement of mutant or wild-type fragments in polyacrylamide gels containing a gradient of denaturant is assayed using denaturing gradient gel electrophoresis (DGGE). See, e.g., Myers et al (1985) *Nature* 313:495. When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA. See, e.g., Rosenbaum and Reissner (1987) *Biophys Chem* 265:12753.

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found. See, e.g. Saiki et al. (1986) *Nature* 324:163); Saiki et al. (1989) *Proc Natl Acad. Sci USA* 86:6230. Such allele specific oligonucleotides are hybridized to PCR amplified target DNA or a number of different mutations when the oligonucleotides are attached to the hybridizing membrane and hybridized with labeled target DNA.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection. See, e.g., Gasparini et al (1992) *Mol Cell Probes* 6:1. It is anticipated that in certain embodiments amplification may also be performed using Taq ligase for amplification. See, e.g., Barany (1991) *Proc Natl Acad Sci USA* 88:189. In such cases, ligation will occur only if there is a perfect match at the 3' end of the 5' sequence, making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a FGF-CX gene.

Furthermore, any cell type or tissue, preferably peripheral blood leukocytes, in which FGF-CX is expressed may be utilized in the prognostic assays described herein. However, any biological sample containing nucleated cells may be used, including, for example, buccal mucosal cells.

Pharmacogenomics

Agents, or modulators that have a stimulatory or inhibitory effect on FGF-CX activity (e.g., FGF-CX gene expression), as identified by a screening assay described herein can be administered to individuals to treat (prophylactically or therapeutically) disorders (e.g., neurological, cancer-related or gestational disorders) associated with aberrant FGF-CX activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of FGF-CX protein, expression of FGF-CX nucleic acid, or mutation content of FGF-CX genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See e.g., Eichelbaum, 1996, *Clin Exp Pharmacol Physiol.* 23:983–985 and Linder, 1997, *Clin Chem.* 43:254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase (G6PD) deficiency is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of FGF-CX protein, expression of FGF-CX nucleic acid, or mutation content of FGF-CX genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a FGF-CX modulator, such as a modulator identified by one of the exemplary screening assays described herein.

Monitoring Clinical Efficacy

Monitoring the influence of agents (e.g., drugs, compounds) on the expression or activity of FGF-CX (e.g., the ability to modulate aberrant cell proliferation and/or differentiation) can be applied in basic drug screening and in clinical trials. For example, the effectiveness of an agent determined by a screening assay as described herein to increase FGF-CX gene expression, protein levels, or upregulate FGF-CX activity, can be monitored in clinical trials of subjects exhibiting decreased FGF-CX gene expression, protein levels, or downregulated FGF-CX activity. Alternatively, the effectiveness of an agent determined by a screening assay to decrease FGF-CX gene expression, protein levels, or downregulate FGF-CX activity, can be monitored in clinical trials of subjects exhibiting increased FGF-CX gene expression, protein levels, or upregulated FGF-CX activity. In such clinical trials, the expression or activity of FGF-CX and, preferably, other genes that have been implicated in, for example, a proliferative or neurological disorder, can be used as a "read out" or marker of the responsiveness of a particular cell.

For example, genes, including FGF-CX, that are modulated in cells by treatment with an agent (e.g. compound, drug or small molecule) that modulates FGF-CX activity (e.g., identified in a screening assay as described herein) can be identified. Thus, to study the effect of agents on cellular proliferation disorders, for example, in a clinical trial, cells can be isolated and RNA prepared and analyzed for the levels of expression of FGF-CX and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of FGF-CX or other genes. In this way, the gene expression pattern can serve as a marker, indicative of the physiological response of the cells to the agent. Accordingly, this response state may be determined before, and at various points during, treatment of the individual with the agent.

In one embodiment, the invention provides a method for monitoring the effectiveness of treatment of a subject with an agent (e.g., an agonist, antagonist, protein, peptide, nucleic acid, peptidomimetic, small molecule, or other drug candidate identified by the screening assays described herein) comprising the steps of (i) obtaining a pre-administration sample from a subject prior to administration of the agent; (ii) detecting the level of expression of a FGF-CX protein, mRNA, or genomic DNA in the preadministration sample; (iii) obtaining one or more post-administration samples from the subject; (iv) detecting the level of expression or activity of the FGF-CX protein, mRNA, or genomic DNA in the post-administration samples, (v) comparing the level of expression or activity of the FGF-CX protein, mRNA, or genomic DNA in the pre-administration sample with the FGF-CX protein, mRNA, or genomic DNA in the post administration sample or samples; and (vi) altering the administration of the agent to the subject accordingly. For example, increased administration of the agent may be desirable to increase the expression or activity of FGF-CX to higher levels than detected, i.e., to increase the effectiveness of the agent. Alternatively, decreased administration of the agent may be desirable to decrease expression or activity of FGF-CX to lower levels than detected, i.e., to decrease the effectiveness of the agent.

Methods of Treatment

The present invention provides for both prophylactic and therapeutic methods of treating a subject at risk of (or susceptible to) a disorder or having a disorder associated with aberrant FGF-CX expression or activity.

Diseases and disorders that are characterized by increased (relative to a subject not suffering from the disease or disorder) levels or biological activity may be treated with Therapeutics that antagonize (i.e., reduce or inhibit) activity. Therapeutics that antagonize activity may be administered in a therapeutic or prophylactic manner. Therapeutics that may be utilized include, but are not limited to, (i) a FGF-CX polypeptide, or analogs, derivatives, fragments or homologs thereof, (ii) antibodies to a FGF-CX peptide; (iii) nucleic acids encoding a FGF-CX peptide; (iv) administration of antisense nucleic acid and nucleic acids that are "dysfunctional" (i.e., due to a heterologous insertion within the coding sequences of coding sequences to a FGF-CX peptide) that are utilized to "knockout" endogenous function of a FGF-CX peptide by homologous recombination (see, e.g., Capecchi, 1989. *Science* 244: 1288–1292); or (v) modulators (i.e., inhibitors, agonists and antagonists, including additional peptide mimetic of the invention or antibodies specific to a peptide of the invention) that alter the interaction between a FGF-CX peptide and its binding partner.

Diseases and disorders that are characterized by decreased (relative to a subject not suffering from the disease or disorder) levels or biological activity may be treated with Therapeutics that increase (i.e., are agonists to) activity. Therapeutics that upregulate activity may be administered in a therapeutic or prophylactic manner. Therapeutics that may be utilized include, but are not limited to, a FGF-CX peptide, or analogs, derivatives, fragments or homologs thereof; or an agonist that increases bioavailability.

Increased or decreased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of a FGF-CX peptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, etc.).

In one aspect, the invention provides a method for preventing, in a subject, a disease or condition associated with an aberrant FGF-CX expression or activity, by administering to the subject an agent that modulates FGF-CX expression or at least one FGF-CX activity. Subjects at risk for a disease that is caused or contributed to by aberrant FGF-CX expression or activity can be identified by, for example, any or a combination of diagnostic or prognostic assays as described herein. Administration of a prophylactic agent can occur prior to the manifestation of symptoms characteristic of the FGF-CX aberrancy, such that a disease or disorder is prevented or, alternatively, delayed in its progression. Depending on the type of FGF-CX aberrancy, for example, a FGF-CX agonist or FGF-CX antagonist agent can be used for treating the subject. The appropriate agent can be determined based on screening assays described herein.

Another aspect of the invention pertains to methods of modulating FGF-CX expression or activity for therapeutic purposes. The modulatory method of the invention involves contacting a cell with an agent that modulates one or more of the activities of FGF-CX protein activity associated with the cell. An agent that modulates FGF-CX protein activity can be an agent as described herein, such as a nucleic acid or a protein, a naturally-occurring cognate ligand of a FGF-CX protein, a peptide, a FGF-CX peptidomimetic, or other small molecule. In one embodiment, the agent stimulates one or more FGF-CX protein activity. Examples of such stimulatory agents include active FGF-CX protein and a nucleic acid molecule encoding FGF-CX that has been introduced into the cell. In another embodiment, the agent inhibits one or more FGF-CX protein activity. Examples of such inhibitory agents include antisense FGF-CX nucleic acid molecules and anti-FGF-CX antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a FGF-CX protein or nucleic acid molecule. In one embodiment, the method involves administering an agent (e.g., an agent identified by a screening assay described herein), or combination of agents that modulates (e.g., upregulates or downregulates) FGF-CX expression or activity. In another embodiment, the method involves administering a FGF-CX protein or nucleic acid molecule as therapy to compensate for reduced or aberrant FGF-CX expression or activity.

The invention will be further illustrated in the following non-limiting examples.

EXAMPLES

Example 1

Identification of the FGF-CX Gene

The FGF-CX gene was identified following a TBLASTN (Altschul, S. F., Gish. W., Miller. W., Myers, E. W. & Lipman, D. J. (1990)*J. Mol. Biol.* 215, 403–410) search of Genbanlk human genomic DNA sequences with *Xenopus* FGF-CX (Koga, C., Adati, N., Nakata, K., Mikoshiba, K., Furuhata, Y., Sata, S., Tei. H. Sakati. Y. Kurokawa. T. Shiokawa, K. & Yokoyama, K. K. (1999) *Biochem. Biophys. Res. Comm.* 261, 756–765; Accession No. AB012615) as query. This search identified a locus (Accession No. AB020858) of high homology on chromosome 8. Intron/exon boundaries were deduced using standard consensus splicing parameters (Mount, S. M. (1996) *Science* 271, 1690–1692), together with homologies derived from known FGFs. The FGF-CX initiation codon localizes to bp 16214 of the sequence of AB020858, and the remaining 3' portion of this exon continues to bp 15930. The 5' UTR of FGF-CX was extended upstream of the initiation codon by an additional 606 bp using public ESTs (Accession Nos. AA232729, AA236522, AI272876 and AI272878). The remaining structure of the FGF-CX gene as it relates to locus AB020858 is as follows: intron 1 (bp 15929–9942); exon 2 (bp 9941–9838); intron 2 (bp 9837–7500); exon 3 (begins at bp 7499 and continues as shown in FIG. 13; the structure of the 3' untranslated region has not yet been determined).

The gene discovered by the procedure in the preceding paragraph includes 3 exons and 2 introns (FIG. 13). The DNA sequence predicts an ORF of 211 amino acid residues, with an in-frame stop codon 117 bp upstream of the initiator methionine. The DNA segment from which the gene was mined maps to chromosome 8p21.3–p22, a location that was confirmed by radiation hybrid analysis (see Example 2).

An FGF signature motif, G-X-[LI]-X-[STAGP]-X(6,7)-[DE]-C-X-[FLM]-X-E-X(6)-Y, identified by a PROSITE search (Bucher, P. & Bairoch, A. (1994) *Ismh.* 2, 53–61) located between amino acid residues 125–148 is double-underlined, and intron/exon boundaries are depicted with arrows. Introns 1 and 2 are 5988 bp and 2338 bp long, respectively. The 5' UTR sequence was derived from public ESTs, and is not shown in its entirety.

Example 2

Radiation Hybrid Mapping of FGF-CX

Radiation hybrid mapping using human chromosome markers was carried out for FGF-CX. The procedure used is analogous to that described in Steen, R G et al. (A High-Density Integrated Genetic Linkage and Radiation Hybrid Map of the Laboratory Rat, Genome Research 1999 (Published Online on May 21, 1999)Vol. 9, AP1–AP8, 1999). A panel of 93 cell clones containing the randomized radiation-induced human chromosomal fragments was screened in 96 well plates using PCR primers designed to identify the sought clones in a unique fashion. The DNA segment from which the nucleotide sequence encoding FGF-CX was identified was annotated as mapping to chromosome 8p21.3–p22. This result was refined by the present analysis by finding that FGF-CX maps to chromosome 8 at a locus which overlaps marker AFM177XB10, and which is 1.6 cR from marker WI-5104 and 3.2 cR from marker WI-9262.

Example 3

Molecular Cloning of the Sequence Encoding a FGF-CX Protein

Oligonucleotide primers were designed for the amplification by PCR of a DNA segment, representing an open reading frame, coding for the full length FGF-CX. The forward primer includes a BglII restriction site (AGATCT) and a consensus Kozak sequence (CCACC). The reverse primer contains an in-frame XhoI restriction site for further subcloning purposes. Both the forward and the reverse primers contain a 5' clamp sequence (CTCGTC). The sequences of the primers are the following:

```
FGF-CX-Forward:  5'-CTCGTC AGATCT CCACC ATG GCT CCC TTA GCC GAA GTC-3'   (SEQ ID NO:3)

FGF-CX-Reverse:  5'-CTCGTC CTCGAG AGT GTA CAT CAG TAG GTC CTT G-3'       (SEQ ID NO:4)
```

PCR reactions were performed using a total of 5 ng human prostate cDNA template, 1 µM of each of the FGF-CX-Forward and FGF-CX-Reverse primers, 5 micromoles dNTP (Clontech Laboratories, Palo Alto Calif.) and 1 microliter of 50× Advantage-HF 2 polymerase (Clontech Laboratories) in 50 microliter volume. The following PCR reaction conditions were used:

| a) | 96° C. | 3 minutes |
|---|---|---|
| b) | 96° C. | 30 seconds denaturation |
| c) | 70° C. | 30 seconds, primer annealing. This temperature was gradually decreased by 1° C./cycle. |
| d) | 72° C. | 1 minute extension. Repeat steps (b)–(d) ten times |
| e) | 96° C. | 30 seconds denaturation |
| f) | 60° C. | 30 seconds annealing |
| g) | 72° C. | 1 minute extension Repeat steps (e)–(g) 25 times |
| h) | 72° C. | 5 minutes final extension |

A single PCR product, with the expected size of approximately 640 bp, was isolated after electrophoresis on agarose gel and ligated into a pCR2.1 vector (Invitrogen, Carlsbad, Calif.). The cloned insert was sequenced using vector specific M13 Forward(–40) and M3 Reverse primers, which verified that the nucleotide sequence was 100% identical to the sequence in FIG. 1 (SEQ ID NO:1) inserted directly between the upstream BglII cloning site and the downstream XhoI cloning site. The cloned sequence constitutes an open reading frame coding for the predicted FGF-CX full length protein. The clone is called TA-AB02085-S274-F19.

Example 4

Preparation of Mammalian Expression Vector pCEP4/Sec

The oligonucleotide primers pSec-V5-His Forward (CTCGT CCTCG AGGGT AAGCC TATCC CTAAC (SEQ ID NO:14)) and pSec-V5-His Reverse (CTCGT CGGGC CCCTG ATCAG CGGGT TTAAA C (SEQ ID NO:15)), were designed to amplify a fragment from the pcDNA3.1-V5His (Invitrogen, Carlsbad, Calif.) expression vector that includes V5 and His6. The PCR product was digested with XhoI and ApaI and ligated into the XhoI/ApaI digested pSecTag2 B vector harboring an Ig kappa leader sequence (Invitrogen, Carlsbad Calif.). The correct structure of the resulting vector, pSecV5His, including an in-frame Ig-kappa leader and V5-His6 was verified by DNA sequence analysis. The vector pSecV5His was digested with PmeI and NheI to provide a fragment retaining the above elements in the correct frame. The PmeI-NheI fragment was ligated into the BamHI/Klenow and NheI treated vector pCEP4 (Invitrogen, Carlsbad, Calif.). The resulting vector was named pCEP4/Sec and includes an in-frame Ig kappa leader, a site for insertion of a clone of interest, and the V5 epitope and 6×His under control of the PCMV and/or the PT7 promoter. pCEP4/Sec is an expression vector that allows heterologous protein expression and secretion by fusing any protein into a multiple cloning site following the Ig kappa chain signal peptide. Detection and purification of the expressed protein are aided by the presence of the V5 epitope tag and 6×His tag at the C-terminus (Invitrogen, Carlsbad, Calif.).

Example 5

Expression of FGF-CX in Human Embryonic Kidney (KEK) 293 Cells

The BglII-XhoI fragment containing the FGF-CX sequence was isolated from TA-AB02085-S274-F19 (Example 3) and subcloned into the BamHI-XhoI digested pCEP4/Sec to generate the expression vector pCEP4/Sec-FGF-CX. The pCEP4/Sec-FGF-CX vector was transfected into 293 cells using the LipofectaminePlus reagent following the manufacturer's instructions (Gibco/BRL/Life Technologies, Rockville, Md.). The cell pellet and supernatant were harvested 72 hours after transfection and examined for FGF-CX expression by Western blotting (reducing conditions) with an anti-V5 antibody. FIG. 12 shows that FGF-CX is expressed as a polypeptide having an apparent molecular weight (Mr) of approximately 34 kDa proteins secreted by 293 cells. In addition a minor band is observed at about 31 kDa.

Example 6

Expression of FGF-CX in E. coli.

Figure 14:
FIG. 14 shows a Western analysis of FGF-CX protein expressed in *E. coli* cells.

The vector pRSETA (InVitrogen Inc., Carlsbad, Calif.) was digested with XhoI and NcoI restriction enzymes. Oligonucleotide linkers of the sequence 5' CATGGTCAGC-CTAC 3' (SEQ ID NO:16) and 5' TCGAGTAGGCTGAC 3' (SEQ ID NO:17) were annealed at 37 degree Celsius and ligated into the XhoI-NcoI treated pRSETA. The resulting vector was confirmed by restriction analysis and sequencing and was named pETMY. The BglII-XhoI fragment of the sequence encoding FGF-CX (see Example 3) was ligated into vector pETMY that was digested with BamHI and XhoI restriction enzymes. The expression vector is named pETMY-FGF-CX. In this vector, hFGF-CX was fused to the 6×His tag and T7 epitope at its N-terminus. The plasmid pETMY-FGF-CX was then transfected into the *E. coli* expression host BL21(DE3, pLys) (Novagen, Madison, Wis.) and expression of protein FGF-CX was induced according to the manufacturer's instructions. After induction, total cells were harvested, and proteins were analyzed by Western blotting using anti-HisGly antibody (Invitrogen, Carlsbad, Calif.). FIG. 14 shows that FGF-CX was expressed as a protein of Mr approximately 32 kDa.

Example 7

Comparison of Expression of Recombinant FGF-CX Protein With and Without a Cloned Signal Peptide a) Expression Without a Signal Peptide As noted in the Detailed Description of the Invention, FGF-CX apparently lacks a classical amino-terminal signal sequence. To determine whether FGF-CX is secreted from mammalian cells, cDNA obtained as the BglII-XhoI fragment, encoding the full length FGF-CX protein, was subcloned from TA-AB02085-S274-F19 (Example 3) into BamHI/XhoI-digested pcDNA3.1 (Invitrogen). This provided a mammalian expression vector designated pFGF-CX. This construct incorporates the V5 epitope tag and a polyhistidine tag into the carboxy-terminus of the protein to aid in its identification and purification, respectively, and should generate a polypeptide of about 27 kDa. Following transient transfection into 293 human embryonic kidney cells, conditioned media was harvested 48 hr post transfection.

In addition to secretion of FGF-CX into conditioned media, it also found to be associated with the cell pellet/ECM (data not shown). Since FGFs are known to bind to heparin sulfate proteoglycan (HSPG) present on the surface of cells and in the extracellular matrix (ECM), the inventors investigated the possibility that FGF-CX was sequestered in this manner. To this end, FGF-CX-transfected cells were extracted by treatment with 0.5 ml DMEM containing 100 M suramin, a compound known to disrupt low affinity interactions between growth factors and HSPGs (La Rocca, R. V., Stein, C. A. & Myers, C. E. (1990) *Cancer Cells* 2, 106–115), for 30 min at 4° C. The suramin-extracted conditioned media was then harvested and clarified by centrifigation (5 min, 2000×g).

The conditioned media and the suramin extract were then mixed with equal volumes of 2× gel-loading buffer. Samples were boiled for 10 min, resolved by SDS-PAGE on 4–20% gradient polyacrylamide gels (Novex, Dan Diego, Calif.) under reducing conditions, and transferred to nitrocelluose filters (Novex). Western analysis was performed according to standard procedures using HRP-conjugated anti-V5 antibody (Invitrogen) and the ECL detection system (Amersham Pharmacia Biotech, Piscataway, N.J.).

One band having the expected Mr was identified in conditioned media from 293 cells transfected with pFGF-CX (FIG. 11A, lane 1). Conditioned media from cells transfected with control vector did not react with the antibody (FIG. 11A, lane 5). After suramin treatment, it was found that a significant quantity of FGF-CX could in fact be released from the cell surface/ECM, indicating that HSPGs are likely to play a role in sequestering this protein (FIG. 11A, lane 2). These results indicate that FGF-CX can be secreted without a classical signal peptide.

Recombinant FGF-CX protein stimulates DNA synthesis and cell proliferation, effects that are likely to be mediated via high affinity binding of FGF-CX to a cell surface receptor, and modulated via low affinity interactions with HSPGs. The suramin extraction data suggests that FGF-CX binds to HSPGs present on the cell surface and/or the ECM.

b) Expression With a Signal Peptide

With the goal of enhancing protein secretion, a construct (pCEP4/Sec-FGF-CX) was generated in which the FGF-CX cDNA was fused in frame with a cleavable amino-terminal secretory signal sequence derived from the Igκ gene. The resulting protein also contained carboxy-terminal V5 and polyhistidine tags as described above for pFGF-CX. Following transfection into 293 cells, a protein product having the expected Mr of about 31 kDa was obtained, and suramin was again found to release a significant quantity of sequestered FGF-CX protein (FIG. 11A; lanes 3 and 4). As expected, pCEP4/Sec-FGF-CX generated more soluble FGF-CX protein than did pFGF-CX.

Results similar to those described above for 293 cells were also obtained with NIH 3T3 cells (FIG. 11B).

Example 8

Real Time Quantitative Expression Analysis Of FGF-CX Nucleic Acids By PCR

The quantitative expression of various clones was assessed in 41 normal and 55 tumor samples (in most cases, the samples presented in FIG. 15, Panels A and B are those identified in Table 3) by real time quantitative PCR (TAQ-MAN® analysis) performed on a Perkin-Elmer Biosystems ABI PRISM® 7700 Sequence Detection System. In Table 3, the following abbreviations are used:

ca.=carcinoma,
*=established from metastasis,
met=metastasis,
s cell var=small cell variant,
non-s=non-sm=non-small,
squam=squamous,
pl.eff=pl effusion=pleural effusion,
glio=glioma,
astro=astrocytoma, and
neuro=neuroblastoma.

First, 96 RNA samples were normalized to β-actin and glyceraldehyde-3-phosphate dehydrogenase (GAPDH). RNA (~50 ng total or ~1 ng polyA+) was converted to cDNA using the TAQMAN® Reverse Transcription Reagents Kit (PE Biosystems, Foster City, Calif.; cat # N808-0234) and random hexamers according to the manufacturer's protocol. Reactions were performed in 20 ul and incubated for 30 min. at 48° C. cDNA (5 ul) was then transferred to a separate plate for the TAQMAN® reaction using β-actin and GAPDH TAQMAN® Assay Reagents (PE Biosystems; cat. no.'s 4310881E and 4310884E, respectively) and TAQMAN® universal PCR Master Mix (PE Biosystems; cat # 4304447) according to the manufacturer's protocol. Reactions were performed in 25 ul using the following parameters: 2 min. at 50° C.; 10 min. at 95° C.; 15 sec. at 95° C./1 min. at 60° C. (40 cycles). Results were recorded as CT values (cycle at which a given sample crosses a threshold level of fluorescence) using a log scale, with the difference in RNA concentration between a given sample and the sample with the lowest CT value being represented as 2 to the power of delta CT. The percent relative expression is then obtained by taking the reciprocal of this RNA difference and multiplying by 100. The average CT values obtained for β-actin and GAPDH were used to normalize RNA samples. The RNA sample generating the highest CT value required no further diluting, while all other samples were diluted relative to this sample according to their β-actin/GAPDH average CT values.

Normalized RNA (5 ul) was converted to cDNA and analyzed via TAQMAN® using One Step RT-PCR Master Mix Reagents (PE Biosystems; cat. # 4309169) and gene-specific primers according to the manufacturer's instructions. Probes and primers were designed for each assay according to Perkin Elmer Biosystem's *Primer Express* Software package (version I for Apple Computer's Macintosh Power PC) using the sequence of clone 10326230.0.38 as input. Default settings were used for reaction conditions and the following parameters were set before selecting primers: primer concentration=250 nM, primer melting temperature ($T_m$) range=58°–60° C., primer optimal $T_m$=59° C., maximum primer difference=2° C., probe does not have 5' G, probe $T_m$ must be 10° C. greater than primer $T_m$, amplicon size 75 bp to 100 bp. The probes and primers selected (see below) were synthesized by Synthegen (Houston, Tx., USA). Probes were double purified by HPLC to remove uncoupled dye and evaluated by mass spectroscopy to verify coupling of reporter and quencher dyes to the 5' and 3' ends of the probe, respectively. Their final concentrations were: forward and reverse primers, 900 nM each, and probe, 200 nM.

For PCR, normalized RNA from each tissue and each cell line was spotted in each well of a 96 well PCR plate (Perkin Elmer Biosystems). PCR cocktails including two probes (one specific for FGF-CX and a second gene-specific probe to serve as an internal standard) were set up using 1× TaqMan™ PCR Master Mix for the PE Biosystems 7700, with 5 mM MgCl2, dNTPs (dA, G. C, U at 1:1:1:2 ratios), 0.25 U/ml AmpliTaq Gold™ (PE Biosystems), and 0.4 U/µl RNase inhibitor, and 0.25 U/l reverse transcriptase. Reverse transcription was performed at 48° C. for 30 minutes followed by amplification/PCR cycles as follows: 95° C. 10 min. then 40 cycles of 95° C. for 15 seconds, 60° C. for 1 minute.

TABLE 3

Tissue Samples used in TaqMan Expression Analysis.

| No. | Tissue Sample | No | Tissue Sample |
|---|---|---|---|
| 1 | Endothelial cells | 49 | Renal ca. 786-0 |
| 2 | Endothelial cells (treated) | 50 | Renal ca. A498 |
| 3 | Pancreas | 51 | Renal ca. RXF 393 |
| 4 | Pancreatic ca. CAPAN 2 | 52 | Renal ca. ACHN |
| 5 | Adipose | 53 | Renal ca. UO-31 |
| 6 | Adrenal gland | 54 | Renal ca. TK-10 |
| 7 | Thyroid | 55 | Liver |
| 8 | Salivary gland | 56 | Liver (fetal) |
| 9 | Pituitary gland | 57 | Liver ca. (hepatoblast) HepG2 |
| 10 | Brain (fetal) | 58 | Lung |
| 11 | Brain (whole) | 59 | Lung (fetal) |
| 12 | Brain (amygdala) | 60 | Lung ca. (small cell) LX-1 |
| 13 | Brain (cerebellum) | 61 | Lung ca. (small cell) NCI-H69 |
| 14 | Brain (hippocampus) | 62 | Lung ca. (s.cell var.) SHP-77 |
| 15 | Brain (hypothalamus) | 63 | Lung ca. (large cell)NCI-H460 |
| 16 | Brain (substantia nigra) | 64 | Lung ca. (non-sm. cell) A549 |
| 17 | Brain (thalamus) | 65 | Lung ca. (non-s.cell) NCI-H23 |
| 18 | Spinal cord | 66 | Lung ca (non-s.cell) HOP-62 |
| 19 | CNS ca. (glio/astro) U87-MG | 67 | Lung ca. (non-s.cl) NCI-H522 |
| 20 | CNS ca. (glio/astro) U-118-MG | 68 | Lung ca. (squam.) SW 900 |
| 21 | CNS ca. (astro) SW1783 | 69 | Lung ca. (squam.) NCI-H596 |
| 22 | CNS ca.* (neuro; met) SK-N-AS | 70 | Mammary gland |
| 23 | CNS ca. (astro) SF-539 | 71 | Breast ca.* (pl. effusion) MCF-7 |
| 24 | CNS ca. (astro) SNB-75 | 72 | Breast ca.* (pl.ef) MDA-MB-231 |
| 25 | CNS ca. (glio) SNB-19 | 73 | Breast ca.* (pl. effusion) T47D |
| 26 | CNS ca. (glio) U251 | 74 | Breast ca. BT-549 |
| 27 | CNS ca. (glio) SF-295 | 75 | Breast ca. MDA-N |
| 28 | Heart | 76 | Ovary |
| 29 | Skeletal muscle | 77 | Ovarian ca. OVCAR-3 |
| 30 | Bone marrow | 78 | Ovarian ca. OVCAR-4 |
| 31 | Thymus | 79 | Ovarian ca. OVCAR-5 |
| 32 | Spleen | 80 | Ovarian ca. OVCAR-8 |
| 33 | Lymph node | 81 | Ovarian ca. IGROV-1 |
| 34 | Colon (ascending) | 82 | Ovarian ca.* (ascites) SK-OV-3 |
| 35 | Stomach | 83 | Myometrium |
| 36 | Small intestine | 84 | Uterus |
| 37 | Colon ca. SW480 | 85 | Placenta |
| 38 | Colon ca.* (SW480 met)SW620 | 86 | Prostate |
| 39 | Colon ca. HT29 | 87 | Prostate ca.* (bone met)PC-3 |
| 40 | Colon ca. HCT-116 | 88 | Testis |
| 41 | Colon ca. CaCo-2 | 89 | Melanoma Hs688(A).T |
| 42 | Colon ca. HCT-15 | 90 | Melanoma* (met) Hs688(B).T |
| 43 | Colon ca. HCC-2998 | 91 | Melanoma UACC-62 |
| 44 | Gastric ca.* (liver met) NCI-N87 | 92 | Melanoma M14 |
| 45 | Bladder | 93 | Melanoma LOX IMVI |
| 46 | Trachea | 94 | Melanoma* (met) SK-MEL-5 |
| 47 | Kidney | 95 | Melanoma SK-MEL-28 |
| 48 | Kidney (fetal) | 96 | Melanoma UACC-257 |

The following primers and probe were designed. Each possesses a minimum of three mismatches for corresponding regions of the highly homologous human FGF-9 and FGF-16 genes so as to be specific for FGF-CX. Set Ag81b covers the region from base 270 to base 343 of FIG. 1 (SEQ ID NO:1). It should not detect other known FGF family members. The primers and probe utilized were:

```
Ag81b (F):  5'-GGACCACAGCCTCTTCGGTA-3'                        (SEQ ID NO:18);

Ag81b (R):  5'-TGTCCACACCTCTAATACTGACCAG-3'                   (SEQ ID NO:19); and Ag81b (P):  5'-FAM-CCCACTGCCACACTGATGAATTCCAA-TAMRA-3'        (SEQ ID NO:20).
```

The results from a representative experiment are shown in FIG. 15. Panels A and B. Expression is plotted as a percentage of the sample exhibiting the highest level of expression. Four replicate runs were made, presented in variously shaded bars. In 39 normal human tissues examined, FGF-CX was found to be most highly expressed in the brain, particularly the cerebellum (FIG. 15. Panels A and B). Other tissues of the central nervous system expressed much lower levels of FGF-CX. Of the 54 human tumor cell lines examined, FGF-CX was found to be most highly expressed in a lung carcinoma cell line (LX-1), a colon carcinoma cell line (SW-480) a colon cancer cell line and metastasis (SW480) and a gastric carcinoma cell line (NCI-N87; see FIG. 15, Panels A and B).

Additional real time expression analysis was done on an extensive panel of tumor tissues obtained during surgery. These tissues include portions obtained from the actual tumors themselves, as well as the portions termed "normal adjacent tissue (NAT)", which typically are already inflamed and show histological evidence of dysplasia. A primer-probe set (Ag81) selected to be specific for FGF-CX was employed in a TaqMan experiment with such surgical tissue samples, in which two replicate runs were performed:

```
Ag81 (F):  5'-AGGCAGAAGCGGGAGATAGAT-3'                       (SEQ ID NO:21);

Ag81 (R):  5'-AGCAGCTTTACCTCATTCACAATG-3'                    (SEQ ID NO:22); and Ag81 (P):  TET-5'-CCATCTACATCCACCACCAGTTGCAGAA-3'-TAMRA      (SEQ ID NO:23).
```

Set Ag81 covers the region from base 477 to base 554 of FIG. 1 (SEQ ID NO:1). The replicates are shown as bars of grey and black shading in FIG. 15. Panels C and D. The results show dramatically that for many matched pairs of tumors and their dysplastic NAT samples, FGF-CX is highly expressed in the NAT but not in the tumor itself, more specifically, in the parenchymal cells adjacent to the tumor. Examples in which this matched pattern arises include ovarian cancer, bladder cancer, uterine cancer, lung cancer, prostate cancer and liver cancer.

Without being limited by theory, it is believed from the results in FIG. 15, Panels C and D that FGF-CX may contribute to tumor progression by paracrine stimulation of the tumor epithelium and/or other components in the host tissue (endothelial cells, stromal fibroblasts, infiltrating lymphocytes, and similar cell types). Likewise, FGF-CX may function to stimulate the components in the host tissue that synthesize or secrete FGF-CX in an autocrine manner. These host component cells may subsequently act on the tumor compartment.

The elevated expression profile of FGF-CX relative to unmatched normal tissue suggests that it plays a prospective or promoting role in tumor progression. Therefore, therapeutic targeting of FGF-CX using any of a number of targeting approaches (including, by way of nonlimiting example, monoclonal antibodies, ribozymes, antisense oligonucleotides, peptides that neutralize the interaction of FGF-CX with cognate receptor(s), and small drugs that modulate the unidentified receptor for FGF-CX) is anticipated to have a positive therapeutic impact on disease progression. Likewise, the use of such agents to modulate the bioactivity of FGF-CX in tumor progression is anticipated to synergize or enhance conventional chemotherapy and radiotherapy. Specific disease indications where therapeutic targeting of FGF-CX might be applied include adenocarcinomas of the colon, prostate, lung, kidney, uterus, breast, bladder, ovary.

Example 9

Stimulation of Bromodeoxyuridine Incorporation by Recombinant FGF-CX

293-EBNA cells (Invitrogen) were transfected using Lipofectamine 2000 according to the manufacturer's protocol (Life Technologies, Gaithersburg, Md.). Cells were supplemented with 10% fetal bovine serum (FBS; Life Technologies) 5 hr post-transfection. To generate protein for BrdU and growth assays (Example 10), cells were washed and fed with Dulbecco's modified Eagle medium (DMFM; Life Technologies) 18 hr post-transfection. After 48 hr, the media was discarded and the cell monolayer was incubated with 100 µM suramin (Sigma. St. Louis, Mo.) in 0.5 ml DMEM for 30 min at 4° C. The suramin-extracted conditioned media was then removed, clarified by centrifugation (5 min; 2000×g), and subjected to TALON metal affinity chromatography according to the manufacturer's instructions (Clontech. Palo Alto, Calif.) taking advantage of the carboxy-terminal polyhistidine tag. Retained fusion protein was released by washing the column with imidazole.

FGF-CX protein concentrations were estimated by Western analysis using a standard curve generated with a V5-tagged protein of known concentration. For Western analysis, conditioned media was harvested 48 hr post transfection, and the cell monolayer was then incubated with 0.5 ml DMEM containing 100 µM suramin for 30 min at 4° C. The suramin-containing conditioned media was then harvested.

To generate control protein, 293-EBNA cells were transfected with pCEP4 plasmid (Invitrogen) and subjected to the purification procedure outlined above.

Recombinant FGF-CX was tested for its ability to induce DNA synthesis in a bromodeoxyuridine (BrdU) incorporation assay. NIH 3T3 cells (ATCC number CRL-1658. American Type Culture Collection, Manassas. Va.). CCD-1070Sk cells (ATCC Number CRL-2091) or MG-63 cells (ATCC Number CRL-1427) were cultured in 96-well plates to ~100% confluence, washed with DMEM, and serum-starved in DMEM for 24 hr (NIH 3T3) or 48 hr (CCD-1070Sk and MG-63). Recombinant FGF-CX or control protein was then added to the cells for 18 hr. The BrdJ assay was performed according to the manufacturer's specifications (Roche Molecular Biochemicals, Indianapolis, Ind.) using a 5 hr BrdU incorporation time.

Figure 16:
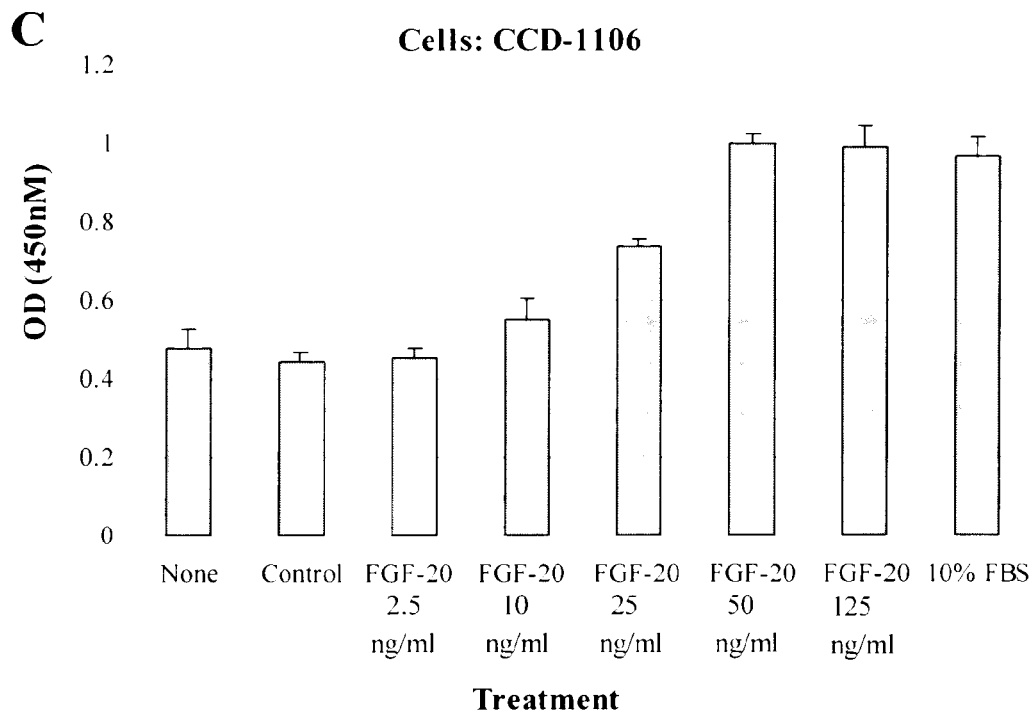
FIG. 16 displays the biological activity of recombinant FGF-CX as represented by its effects on DNA synthesis. Cells were serum-starved, incubated with the indicated factor for 18 hr, and analyzed by a BruU incorporation assay. Samples were performed in triplicate. Panel A, NIH 3T3 mouse fibroblasts. Panel B, CCD-1070 human fibroblasts. Panel C, CCD-1106 human keratinocytes FIG. 17 displays the biological activity of recombinant FGF-CX as represented by its effects on cell growth. NIH 3T3 cells were incubated with serum-free media supplemented with the indicated factor and counted after 48 hr. Samples were performed in duplicate.

It was found that FGF-CX induced DNA synthesis in NIH 3T3 mouse fibroblasts at a half maximal concentration of ~5 ng/ml (FIG. 16 Panel A). In contrast, protein purified from cells transfected with control vector did not induce DNA synthesis. It was also found that FGF-CX induces DNA synthesis, as determined by BrdU incorporation, at comparable dosing levels in a variety of human cell lines including CCD-1070Sk normal human skin fibroblasts (FIG. 16, Panel B). CCD-1106 keratinocytes (FIG. 16, Panel C), MG-63 osteosarcoma cells (data not shown), and breast epithelial cells.

Example 10

Induction of Cell Proliferation by Recombinant FGF-CX

Figure 17:
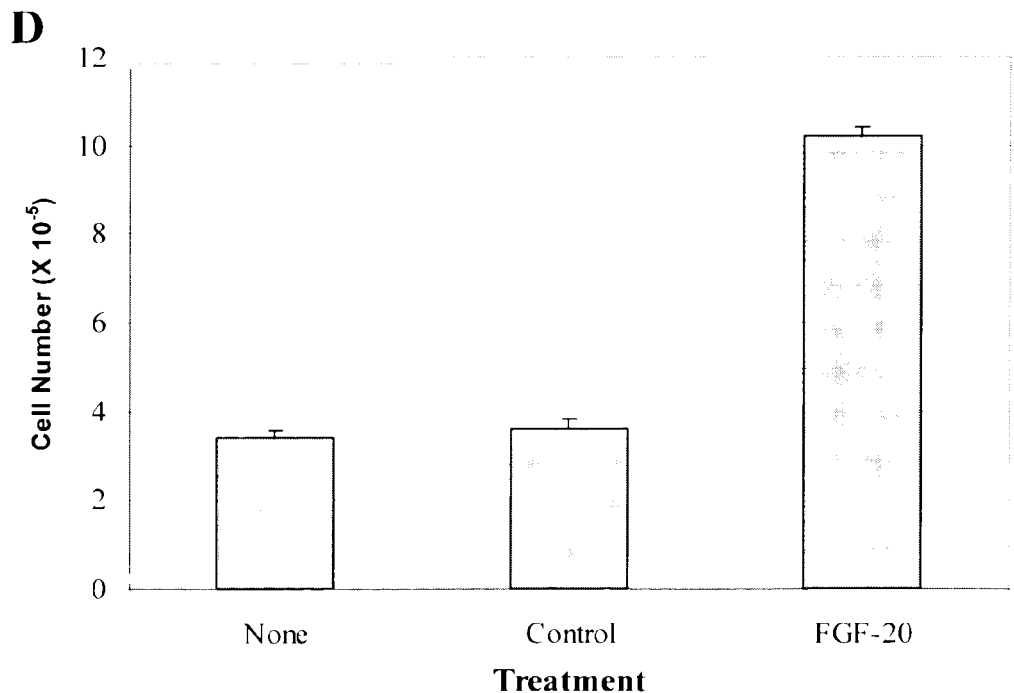

To determine if recombinant FGF-CX induces cell proliferation, NIH 3T3 cells were cultured in 6-well plates to ~50% confluence, washed with DMEM, and fed with DMEM containing recombinant FGF-CX or control protein for 48 hr. and then counted. Cell numbers were determined by trypsinizing the cells and counting them with a Beckman Coulter Z1 series counter (Beckman Coulter, Fullerton, Calif.). It was found that FGF-CX induces about a 3-fold increase in cell number relative to control protein in this assay (FIG. 17).

To document morphological changes incident upon proliferation, NIH 3T3 cells were treated for 48 hr with recombinant FGF-CX or control protein in DMEM/2% calf serum and photographed with a Zeiss Axiovert 100 microscope (Carl Zeiss. Inc., Thornwood, N.Y.).

Figure 18:
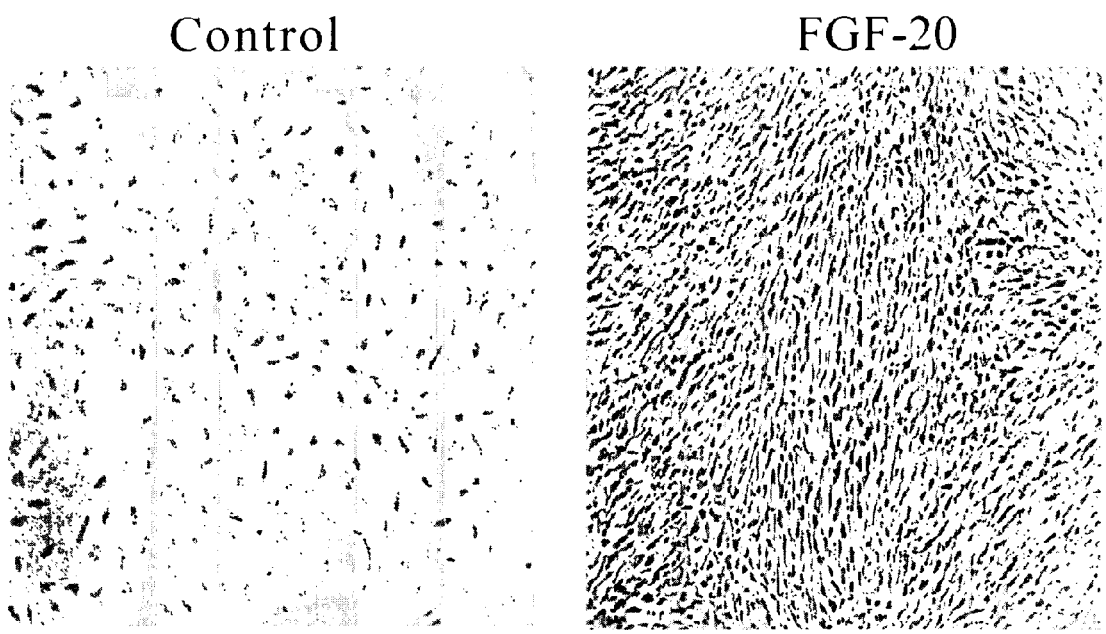
FIG. 18 presents the biological activity of recombinant FGF-CX as represented by its effects on cell morphology. NIH 3T3 cells were incubated with FGF-CX or control protein for 48 hr and photographed at a magnification of X 25.

In addition to reaching a higher cell density (FIG. 17), NIH 3T3 cells cultured in the presence of FGF-CX prepared as described in Example 9 exhibited a disorganized pattern of growth, indicating a loss of contact inhibition (FIG. 18). Furthermore, individual cells were found to be spindly and refractile. These results show that FGF-CX acts as a growth factor and suggest that recombinant FGF-CX mediates the morphological transformation of NIH 3T3 cells.

Example 11

Tumor Formation by Ectopic FGF-CX-Transfected NIH 3T3 Cells in Nude Mice

NIH 3T3 cells were transfected with pCFP4/Sec-FGF-CX or control vector using Lipofectamine Plus according to the manufacturer's protocol (Life Technologies). Cells were supplemented with 10% calf serum (CS; Life Technologies) 5 hr post-transfection. It was found that pCEP4/Sec-FGF-CX-transfected cells were morphologically transformed by 48 hr after transfection, and remained so after 2 weeks of selection in hygromycin-containing growth media. In contrast, cells transfected with control vector retained their normal morphology (data not shown). Thus the transfected cells behave as expected based, for example, on the experiments reported in Example 10.

In order to study the induction of ectopic tumors, NIH 3T3 cells were transfected with various experimental and control vectors. Two days after transfection, cells were placed into either DMEM/5% CS (for pFGF-CX-transfected cells) or DMEM/10% CS supplemented with 500 µg/ml hygromycin B (for pCEP4/Sec-FGF-CX-transfected cells). After 2 weeks of culture, subconfluent cells were trypsinized, neutralized with DMEM/10% CS, washed with PBS and counted. One million cells in PBS were injected into the lateral subcutis of female athymic nude mice (Jackson Laboratories, Bar Harbor, Me.).

NIH 3T3 cells were transfected with FGF-CX expression plasmids (pFGF-CX and pIgκ-FGF-CX) or their appropriate control vectors. We found that cells transfected with either of the FGF-CX expression vectors were morphologically transformed by 48 hr after transfection (data not shown), and possessed a phenotype similar to that generated following exposure of NIH 3T3 cells to recombinant FGF-CX (FIG. 17). In contrast, cells transfected with control vector retained their normal morphology (data not shown).

To determine if ectopic expression of FGF-CX in vivo induces the tumorigenicity of NIH 3T3 cells, stable transfectants were generated and injected subcutaneously into nude mice. By 11 days, all of the animals injected with either pFGF-CX or pIgκ-FGF-CX-transfected cells possessed rapidly growing tumors increasing in size by 14 days, whereas none of the animals injected with control cells developed tumors by 2 weeks (FIG. 19). These results show that cells transformed by transfection with vectors harboring the FGF-CX gene promote the development and growth of tumors in vivo.

Equivalents

From the foregoing detailed description of the specific embodiments of the invention, it should be apparent that particular novel compositions and methods involving nucleic acids, polypeptides, antibodies, detection and treatment have been described. Although these particular embodiments have been disclosed herein in detail, this has been done by way of example for purposes of illustration only, and is not intended to be limiting with respect to the scope of the appended claims that follow. In particular, it is contemplated by the inventors that various substitutions, alterations, and modifications may be made as a matter of routine for a person of ordinary skill in the art to the invention without departing from the spirit and scope of the invention as defined by the claims. Indeed, various modifications of the invention in addition to those described herein will become apparent to those skilled in the art from the foregoing description and accompanying figures. Such modifications are intended to fall within the scope of the appended claims.

What is claimed is:

1. An isolated polypeptide comprising an amino acid sequence shown in SEQ ID NO:2.

2. The polypeptide of claim 1, said polypeptide further comprising at least one conservative amino acid substitution, wherein said polypeptide is a full length polypeptide that retains functional growth factor-like properties of SEQ ID NO: 2, retains the conserved amino acids of the FGF family motif located at residues 125, 127, 129, 136, 137, 139, 141 and 148, and retains the hydrophobic transport domain between residues 92–120, wherein the residues are numbered with respect to SEQ ID NO:2.

3. A composition comprising the polypeptide of claim 1 and a pharmaceutically acceptable carrier.

4. A kit comprising in one or more containers a composition comprising the polypeptide of claim 1 and a pharmaceutically acceptable carrier.

5. The polypeptide of claim 1, the polypeptide further comprising a post-translational modification other than a proteolytic cleavage.

6. The polypeptide of claim 5, wherein the post-translational modification is at least one modification chosen from the group consisting of phosphorylation and N-myristoylation.

* * * * *

UNITED STATES PATENT AND TRADEMARK OFFICE
CERTIFICATE OF CORRECTION

| | | |
|---|---|---|
| PATENT NO. | : 7,056,885 B1 | Page 1 of 1 |
| APPLICATION NO. | : 09/609543 | |
| DATED | : June 6, 2006 | |
| INVENTOR(S) | : Jeffers et al. | |

It is certified that error appears in the above-identified patent and that said Letters Patent is hereby corrected as shown below:

On page 1, line 75, "Henri Lichenstein, Madison, CT (US)" should read
-- Henri Lichenstein, Guilford, CT (US) --

Signed and Sealed this

Fifteenth Day of August, 2006

JON W. DUDAS
*Director of the United States Patent and Trademark Office*